United States Patent [19]

Strupczewski

[11] Patent Number: 4,806,649

[45] Date of Patent: Feb. 21, 1989

[54] 3-(PIPERIDINYL)- AND 3-(PYRROLIDINYL)-1H-INDAZOLES

[75] Inventor: Joseph T. Strupczewski, Flemington, N.J.

[73] Assignee: Hoechst-Roussel Pharmaceuticals, Inc., Somerville, N.J.

[21] Appl. No.: 228,201

[22] Filed: Aug. 4, 1988

Related U.S. Application Data

[60] Division of Ser. No. 181,960, Apr. 15, 1988, Pat. No. 4,775,761, which is a division of Ser. No. 102,684, Sep. 30, 1987, Pat. No. 4,758,668, which is a division of Ser. No. 37,194, Mar. 19, 1987, Pat. No. 4,710,573, which is a division of Ser. No. 811,090, Dec. 19, 1985, Pat. No. 4,670,447, which is a continuation-in-part of Ser. No. 694,198, Jan. 23, 1985, abandoned, which is a continuation-in-part of Ser. No. 679,662, Dec. 7, 1984, abandoned, which is a continuation-in-part of Ser. No. 525,088, Aug. 22, 1983, abandoned.

[51] Int. Cl.$^4$ .......................................... C07D 401/14
[52] U.S. Cl. ...................... 546/193; 544/243; 544/331; 546/22; 546/194; 546/199; 546/271; 548/112; 548/241
[58] Field of Search ............... 546/193, 194, 271, 22, 546/199; 548/241, 112; 544/243, 331

[56] References Cited

U.S. PATENT DOCUMENTS 4,556,660 12/1985 Janssens et al. ............... 546/193 X Primary Examiner—Richard A. Schwartz
Attorney, Agent, or Firm—Tatsuya Ikeda

[57] ABSTRACT

Novel 3-(piperidinyl)- and 3-(pyrrolidinyl)-1H-indazoles, intermediates and processes for the preparation thereof, and methods for treating psychoses, treating depression, alleviating pain, treating convulsions and treating hypertension utilizing compounds or compositions thereof are disclosed.

7 Claims, No Drawings

3-(PIPERIDINYL)- AND 3-(PYRROLIDINYL)-1H-INDAZOLES

This is a division, of application Ser. No. 181,960 filed Apr. 15, 1988, now U.S. Pat. No. 4,775,761, which is a division of application Ser. No. 102,684, filed Sept. 30, 1987, now U.S. Pat. No. 4,758,668, which is a division of application Ser. No. 037,194, filed Mar. 19, 1987 now U.S. Pat. No. 4,710,573, which is a division of application Ser. No. 811,090 filed Dec. 19, 1985, now U.S. Pat. No. 4,670,447, which is a CIP of application Ser. No. 694,198 filed Jan. 23, 1985 now abandoned, which is a CIP of application Ser. No. 679,662 filed Dec. 7, 1984 now abandoned, which in turn is a CIP of application Ser. No. 525,088, filed Aug. 22, 1983 now abandoned.

The present invention relates to novel 3-(piperidinyl)- and 3-(pyrrolidinyl)-1H-indazoles. More particularly, the present invention relates to 3-(piperidinyl)-and 3-pyrrolidinyl)-1H-indazoles of formula 1

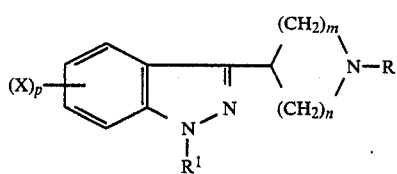

wherein R is hydrogen, loweralkyl, loweralkenyl, lowercycloalkylloweralkyl,

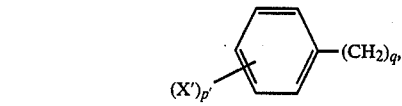

cyano, cyanomethyl, formyl, loweralkanoyl, diloweralkylphosphinylmethyl,

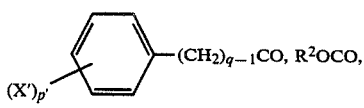

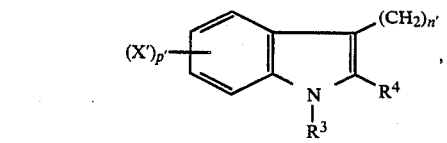

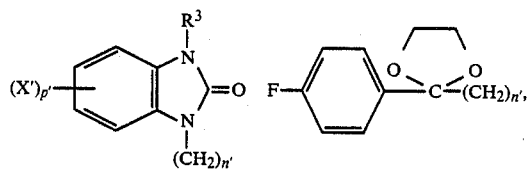

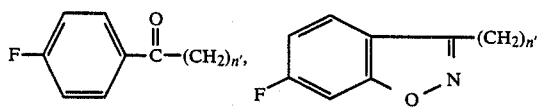

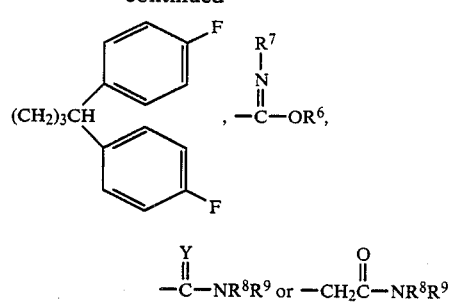

$R^1$ is hydrogen, loweralkyl, loweralkenyl, lowercycloalkylloweralkyl,

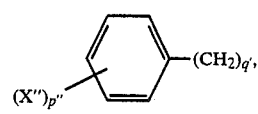

diloweralklaminoloweralkyl, cyano, cyanomethyl, formyl, loweralkanoyl, hydroxymethyl, hydroxyloweralkyl, lowercycloalkylloweralkanoyl, loweralkoxycarbonylloweralkyl,

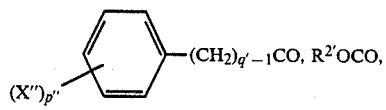

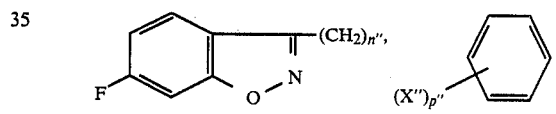

$R^5CO$, 2- or 4- pyridinyl or 2-pyrimidinyl; $R^2$ and $R^{2'}$ are independently loweralkyl, 2,2,2-trichloroethyl or phenyl; $R^3$ and $R^4$ are independently hydrogen or lower alkyl; $R^5$ is a member selected from the group furyl, thienyl, pyridinyl, thiazolyl, isothiazolyl, oxazolyl or isoxazolyl, X, X' and X'' are independently hydrogen, halogen, loweralkyl, loweralkoxy, loweralkanoyl loweralkylthio, cyano, carbamoyl, hydroxy, nitro, amino or trifluoromethyl; Y is oxygen or sulfur; m is 2 or 3; n is 1 or 2; and the sum of m and n is 3 or 4; n' and n'' are independently 2 or 3; p, p' and p'' are independently 1 or 2, except where X'' is halogen p'' is 1 through 5; q and q' are independently 1, 2, 3 or 4; $R^6$ is lower alkyl, aryl, aralkyl, cycloalkylloweralkyl, a loweralkyl substituted with an amino, e.g. -alkylene-NH$_2$, loweralkylamino, e.g. alkyl-NH-, diloweralkylamino, e.g.

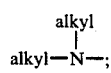

$R^7$, $R^8$ and $R^9$ are independently hydrogen, loweralkyl or aryl; the optical antipode thereof, or the pharmaceutically acceptable acid addition salt thereof, which are useful for treating psychoses, treating depression, treating and alleviating pain, treating hypertension and treating convulsions, alone or in combination with inert adjuvants.

Preferred 3-(piperidinyl)- and 3-(pyrrolidinyl)-1H-indazoles of the present invention are those wherein R is hydrogen, loweralkyl,

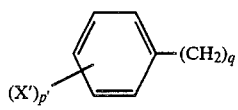

wherein X', p' and q are as above,

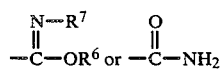

and $R^1$ is hydrogen, loweralkyl, lowercycloalkylloweralkyl, loweralkanoyl, hydroxymethyl, hydroxyloweralkyl,

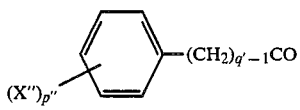

wherein X" and p" are as above and q' is 1 or $R^{2'}OCO$ wherein $R^{2'}$ is as above or

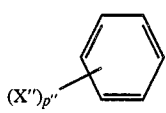

wherein X" and p" are as above. Most preferred are these wherein R is hydrogen, loweralkyl

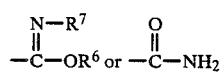

and $R^1$ is

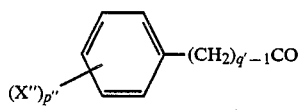

wherein X", p" and q' are as above, hydrogen, lower alkyl, or

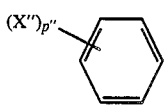

Subgeneric to the 3-(piperidinyl)- and 3-(pyrrolidinyl)-1H-indazoles of the present invention are compounds wherein:
(a) R is hydrogen, loweralkyl, loweralkenyl, lowercycloalkylloweralkyl or

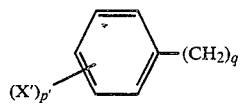

wherein X', p' and q are as above;
(b) R is cyano or cyanomethyl;
(c) R is formyl, loweralknoyl,

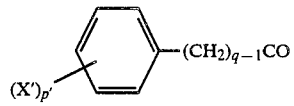

wherein X', p' and q are as above or $R^2OCO$ wherein $R^2$ is as above, and wherein R is as above and q is 1;
(d) R is

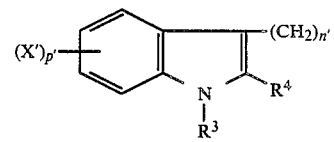

wherein $R^3$, $R^4$, X', n' and p' are as above;
(e) R is

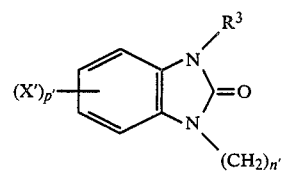

wherein $R^3$, X', n' and p' are as above;
(f) R is

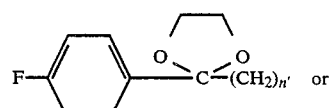

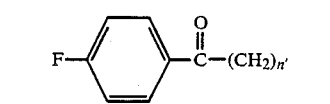

wherein n' is as above;
(g) R is

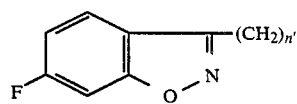

wherein n' is as above;
(h) R is (i) R is

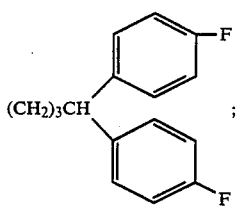

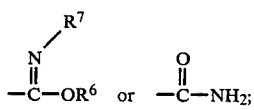

(j) $R^1$ is hydrogen, loweralkyl, loweralkenyl, lowercycloalkylloweralkyl

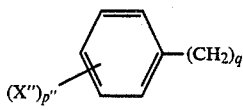

wherein X″, p″ and q′ are as above;
(k) $R^1$ is

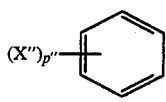

wherein X″ and p″ are as above;
(l) $R^1$ is diloweralkylaminoloweralkyl;
(m) $R^1$ is cyano or cyanomethyl;
(n) $R^1$ is formyl, loweralkanoyl, lowercycloalkyloweralkanoyl,

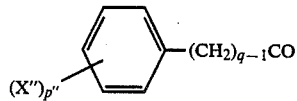

wherein X″, p″ and q′ are as above, or $R^{2'}$ OCO wherein $R^{2'}$ is as above;
(o) $R^1$ is

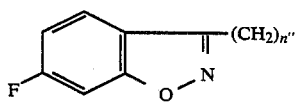

wherein n″ is as above;
(p) $R^1$ is

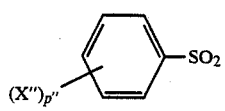

wherein X″ and p″ are as above;
(q) $R^1$ is 2- or 4-pyridinyl or 2-pyrimidinyl;
(r) $R^1$ is $R^5CO$ wherein $R^5$ is as above; and
(s) $R^1$ is hydroxymethyl or hydroxyloweralkyl.

As used through the specification and appended claims, the term "alkyl" refers to a straight or branched chain hydrocarbon radical containing no unsaturation and having 1 to 10 carbon atoms such as methyl, ethyl, 1-propyl, 2-propyl, 1-butyl, 1-pentyl, 2-pentyl, 3-hexyl, 4-heptyl, 2-octyl, 3-nonyl, 4-decyl and the like; the term "alkenyl" refers to a straight or branched chain hydrocarbon radical having one olefinic bond and containing 3 to 10 carbon atoms such as 2-propenyl, 2-butenyl, 3-pentenyl, 3-hexenyl, 3-heptenyl, 4-octenyl, 4-nonenyl, 5-decenyl and the like; the term "cycloalkyl" refers to a saturated hydrocarbon group possessing at least one carbocyclic ring, the ring containing from 3 to 10 carbon atoms such as cyclopropyl, cyclobutyl, cyclopentyl, cyclohexyl, cycloheptyl, cyclodecyl and the like; the term "alkanol" refers to a compound formed by a combination of an alkyl group and a hydroxy radical. Examples of alkanols are methanol, ethanol, 1- and 2-propanol, 1,2-dimethylethanol, hexanol, octanol, decanol and the like. The term "alkoxy" refers to a radical formed by removal of the hydrogen atom from the hydroxy function of an alkanol. Examples of alkoxy are methoxy, ethoxy, 1- and 2-propoxy, 1,2-dimethylethoxy, hexoxy, octoxy, decoxy, and the like. The term "alkanoic acid" refers to a compound formed by combination of carboxyl group with a hydrogen atom or alkyl group. Examples of alkanoic acids are formic acid, acetic acid, propanoic acid, 2,2-dimethylacetic acid, hexanoic acid, octanoic acid, decanoic acid and the like; the term "halogen" refers to a member of the family consisting of fluorine, chlorine, bromime or iodine. The term "alkanoyl" refers to the radical formed by removal of the hydroxyl function from an alkanoic acid. Examples of alkanoyl groups are formyl, acetyl, propionyl, 2,2-dimethylacetyl, hexanoyl, octanoyl, decanoyl and the like. The term "lower" as applied to any of the aforementioned groups refers to a group having a carbon skeleton containing up to and including 7 carbon atoms. The term "alkylene" refers to a bivalent radical of the lower branched or unbranched group it is derived from having valence bonds from two terminal carbons thereof, e.g. ethylene ($-CH_2CH_2-$), propylene ($-CH_2CH_2CH_2-$), isopropylene

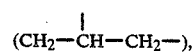

etc. The term "aryl" refers to radical of the formula

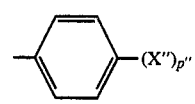

wherein X″ and p″ are as defined above. The term "aralkyl" refers to an aryl-loweralkyl radical wherein "aryl" and "loweralkyl" are as defined above.

The compounds of the present invention which lack an element of symmetry exist as optical antipodes and as the racemic forms thereof. The optical antipode may be prepared from the corresponding racemic forms by standard optical resolution techniques, involving, for example, the separation of diasteromeric salts of those instant compounds characterized by the presence of a basic amino group and an optically active acid, or by the synthesis from optically active precursors.

The present invention comprehends all optical isomers and racemic forms thereof of the compounds disclosed and claimed herein. The formulas of the compounds shown herein are intended to encompass all optical isomers of the compounds so depicted.

The novel 3-(piperidinyl) and 3-(pyrrolidinyl)-1H-indazoles of the present invention are synthesized by processes illustrated in Reaction Schemes A to C.

To prepare the 3-(piperidinyl)- or 3-(pyrrolidinyl)-1H-indazle system of formula 1 wherein R is alkyl, a 1-alkylchloropiperidine 3 or a 1-alkylchloropyrrolidine 3 is condensed with a 2-fluorobenznitrile 4 to a 1-alkyl-(2-fluorobenzoyl)piperidine 5 or a 1-alkyl-(2-fluorobenzoyl)pyrrolidine 5 which is cyclized to a 3-(1-alkyl-piperidinyl)- or a 3-(1-alkylpyrrolidinyl)-1H-indazole 8. See Reaction Scheme A.

The condensation of a 1-alkylchloropiperidine 3 or a 1-alkylchloropyrrolidine 3 with a 2-fluorobenzonitrile 4 is effected by conventional Grignard techniques. Typically, the benzonitrile 4, dissolved in an ethereal solvent, such as tetrahydrofuran, is treated with a Grignard reagent, prepared from the chloropiperidine 3 or chloropyrrolidine 3 and magnesium turnings in an ethereal solvent, such as tetrahydrofuran, followed by hydrolysis under acidic conditions. An initiator such as ethyl bromide may be employed to facilitate formation of the Grignard reagent. The cyclization of a 1-alkyl-(2-fluorobenzoyl)piperidine 5 or a 1-alkyl-(2-fluorobenzoyl)pyrrolidine 5 to a 3-(1:alkylpiperidinyl)-1H-indazole 8 or a 3-(1-alkylpyrrolidinyl)-1H-indazole 8 is performed by treating the benzoylpiperidine 5 or benzoylpyrrolidine 5 with hydrazine, generally as the hydrate, at an elevated temperature and pressure within the range of about 100° to about 200° C., and about 200 to about 300 psi, respectively. A cyclization temperature of about 150° C. is preferred. A cyclization pressure of about 250 psi is also preferred.

To synthesize the 3-(piperidinyl)- or 3-(pyrrolidinyl)-1H-indazole system of formula 1 wherein R is alkenyl, cycloalkylalkyl,

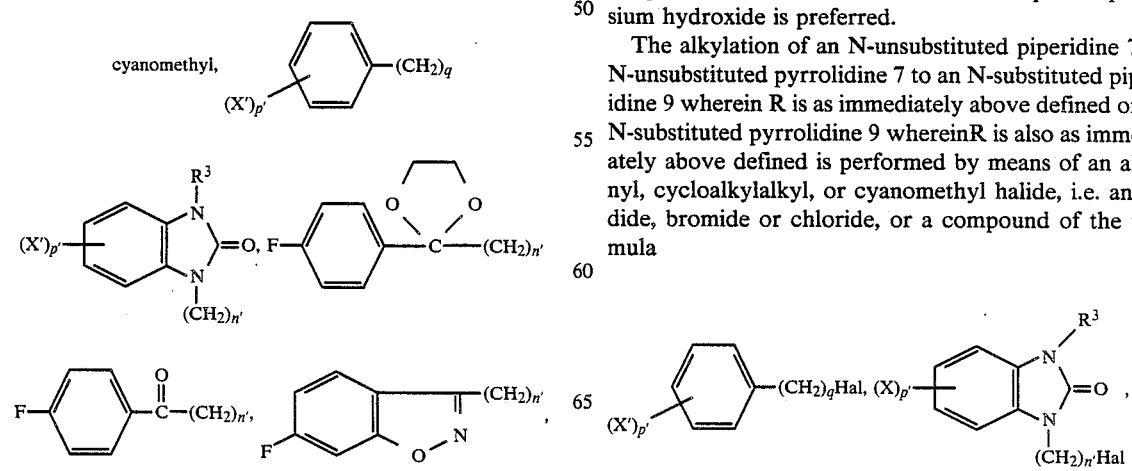

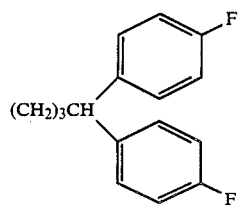

wherein R³, X', n', p' and q are as above, a 1-alkyl-(2-fluorobenzoyl)piperidine 5 or 1-alkyl-(2-fluorobenzoyl)pyrrolidine 5 is converted to a 1-phenoxycarbonyl-(2-fluorobenzoyl)piperidine 6 or 1-phenoxycarbonyl-(2-fluorobenzoyl)pyrrolidine 6 followed by hydrolysis of the 1-phenoxycarbonylpiperidine 6 or 1-phenoxycarbonylpyrrolidine 6 to a (2-fluorobenzoyl)piperidine 7 or (2-fluorobenzoyl)pyrrolidine 7, alkylation of the benzoylpiperidine 7 or benzoylpyrrolidine 7 to an N-substituted benzoylpiperidine 9 or N-substituted benzoylpyrrolidine 9 and cyclization to the indazole 10 wherein R is as immediately above. See Reaction Schemes A and B.

The conversion of the 1-alkylpiperidine 5 or 1-alkylpyrrolidine 5 to the phenoxycarbonylpiperidine 6 or phenoxycarbonylpyrrolidine 6 is accomplished by treating a tertiary amine 5 with phenylchloroformate in an aromatic solvent in the presence of an acid scavenger. Included among aromatic solvents are benzene, toluene, xylene and the like. Toluene is the preferred aromatic solvent. Included among acid scavengers are sodium carbonate, potassium carbonate and the like. Potassium carbonate is preferred. While the reaction temperature is not narrowly critical, it is preferred to conduct the conversion at the reflux temperature of the reaction mixture to assure a reasonable rate of formation of the carbamate 6.

The hydrolysis of the phenoxycarbonylpiperidine 6 or phenoxycarbonylpyrrolidine 6 to the 1-unsubstituted piperidine 7 or 1-unsubstituted pyrrolidine 7 is performed by methods well-known in the art, involving, for example, treatment of the carbamate 6 with an aqueous solution of an alkali metal hydroxide such as sodium hydroxide or potassium hydroxide at or about the reflux temperature of the reaction mixture. Aqueous potassium hydroxide is preferred.

The alkylation of an N-unsubstituted piperidine 7 or N-unsubstituted pyrrolidine 7 to an N-substituted piperidine 9 wherein R is as immediately above defined or an N-substituted pyrrolidine 9 whereinR is also as immediately above defined is performed by means of an alkenyl, cycloalkylalkyl, or cyanomethyl halide, i.e. an iodide, bromide or chloride, or a compound of the formula

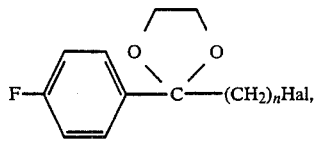

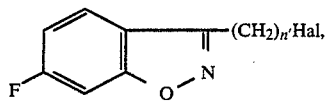

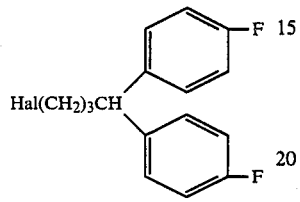

wherein $R^3$, $X'$, $n'$, $p'$ and $q$ are as above and Hal is iodo, bromo or chloro, in the presence of a base suspended or dissolved in a polar aprotic solvent. Suitable bases include alkali metal carbonates and bicarbonates such as, for example, sodium and potassium carbonate and sodium and potassium bicarbonate. Suitable polar aprotic solvents include dimethylformamide, dimethylacetamide and hexamethylphosphoramide. Potassium carbonate and dimethylformamide are the preferred base and solvent. A reaction promoter such as potassium iodide and an elevated reaction temperature within the range of about 70° to about 120° C. may be employed to facilitate the alkylation. A reaction temperature of about 90°C. is preferred.

To furnish the 3-(piperidinyl)- or 3-(pyrrolidinyl)-1H-indazole of formula 1 wherein R is

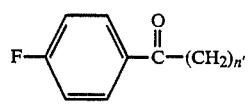

wherein $n'$ is as above the corresponding ethylene glycol cyclic ketal thereof, i.e., a compound of formula 1 wherein R is

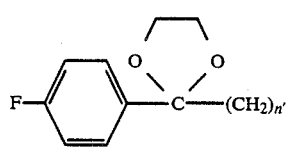

is hydrolyzed. The hydrolysis is conveniently accomplished by conventional methods involving, for example, the interaction of a mineral acid, such as hydrochloric acid, in an alkanol, such as methanol, at ambient temperature, or an elevated temperature such as the reflux temperature of the reaction system.

To introduce the indol-3-ylalkyl function, i.e., to fabricate an N-substituted piperidine or N-substituted pyrrolidine of formula 1 wherein R is a group of the formula

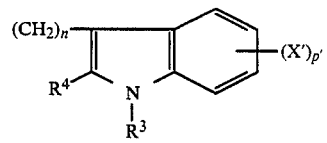

wherein $R^3$, $R^4$, $X'$, $n'$ and $p'$ are as above, one treats an N-unsubstituted piperidine 7 or N-unsubstituted pyrrolidine 7 with a 3-(phenylsulfonylalkyl)indole or 3-(alkylphenylsulfonylalkyl)indole of the formula

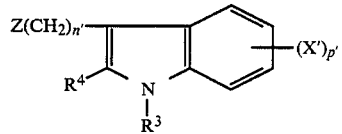

wherein Z is a group of the formula

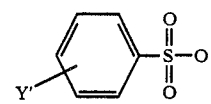

wherein $Y'$ is hydrogen or alkyl and $R^3$, $R^4$, $X'$, $n'$ and $p'$ are as above.

The reaction involving the displacement of the phenylsulfonyl group of the indole is accomplished by treating an N-unsubstituted piperidine 7 or N-unsubstituted pyrrolidine 7 with the phenylsulfonylindole in an aprotic polar solvent, such as dimethylformamide, dimethylacetamide and hexamethylphosphoramide, or an alkanone such as acetone, 2-butanone, 3-pentanone and the like, dimethylformamide and 2-butanone being preferred, in the presence of an acid scavenger such as an alkali metal carbonate (sodium or potassium carbonate) or alkali metal bicarbonate (sodium or potassium bicarbonate), potassium carbonate and sodium bicarbonate being preferred, at a temperature of about 70° to 110° C., preferably a temperature of 90° C., when an aprotic polar solvent is used, and at about the reflux temperature of the reaction system when an alkanone is employed as the solvent.

The cyclization of the N-substituted benzoylpiperidine 9 or N-substituted benzoylpyrrolidine 9 to the 1H-indazole 10 is readily achieved by procedures substantially similar to those utilized for the cyclization of benzoylpiperidine 5 or benzoylpyrrolidine 5 to 1H-indazole 8.

To prepare 1H-indazoles substituted at the 1-position, i.e., compounds of formula 11 wherein $R^1$ is alkyl, alkenyl, cycloalkylalkyl, dialkylaminoalkyl, loweralkoxycarbonylloweralkyl, cyano, cyanomethyl,

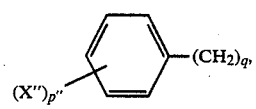

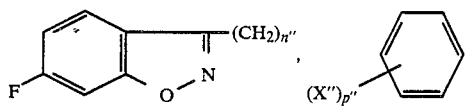

2- or 4-pyridinyl or 2-pyrimidinyl, R is as hereinabovedefined, with the proviso that R is not hydrogen, and X, m, n and p are as hereinbeforedefined, a 1-unsubstituted 1H-indazole 8 wherein R is as hereinbefore defined, with the proviso that R is not hydrogen, and X, m, n and p are as hereinbeforedefined, is treated, respectively, with an alkyl, alkenyl, cycloalkylalkyl, dialkylaminoalkyl, loweralkylcarbonyl halide, cyanogen, cyanomethyl, 2- or 4-pyridinyl or 2-pyrimidinyl halide, i.e., an iodide, bromide or chloride, or a compound of the formula

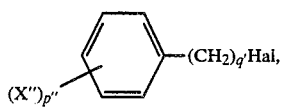

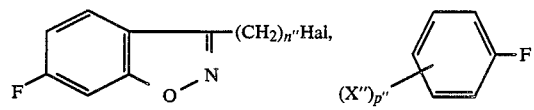

wherein X″, n″, q′ and p″ are as defined above and Hal is iodo, bromo or chloro, in the presence of an alkali metal hydride suspended in a polar aprotic solvent. Among alkali metal hydrides, there may be mentioned lithium hydride, potassium hydride and sodium hydride. Sodium hydride is preferred. Among polar aprotic solvents, there may be mentioned dimethylformamide, dimethylacetamide and hexamethylphosphoramide. Dimethylformamide is preferred. While the alkylation normally proceeds readily at ambient temperature, the reaction may be conducted at an elevated temperature of about 50° to about 100° C. to facilitate the conversion. See Reaction Scheme C.

Alternatively, 1H-indazoles substituted at the 1-position by a group of the formula

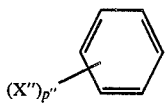

i.e., compounds of the formula 11 wherein $R^1$ is

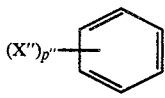

wherein X″ is hydrogen, halogen, alkyl, alkoxy, hydroxy or amino and p″ is 1 or 2, may be prepared from the corresponding compounds wherein X″ is nitro by conventional methods involving, for example, reduction of nitro group to an amino function, diazotization and subsequent displacement or reduction of the diazonium moiety.

To provide a 1-hydroxymethyl-3-(piperidinyl)-1H-indazole 13 or 1-hydroxymethyl-3-(pyrrolidinyl)-1H-indazole 13, a 1-unsubstituted 3-(piperidinyl)-1H-indazole 8 or 1-unsubstituted 3-(pyrrolidinyl)-1H-indazole 8 wherein R is as hereinbeforedefined, with the exception that R is not hydrogen, is treated with formaldehyde in the form of paraformaldehyde or trioxane in an alkanol such as methanol, ethanol, 2-propanol and the like, preferably ethanol, in the presence of an alkali metal hydroxide such as lithium hydroxide, sodium hydroxide, or potassium hydroxide, sodium hydroxide being preferred, at an elevated temperature of about the reflux temperature of the reaction mixture.

To prepare the hydroxymethyl-1H-indazole 13 wherein R is hydrogen, one conducts the condensation on, for example, an N-phenoxycarbonyl-1H-indazole of formula 10 and then removes the carbamoyl group under conventional mild hydrolysis conditions.

To fabricate the 3-(piperidinyl)- or 3-(pyrrolidinyl)-1H-indazole system of formula 1 wherein R is

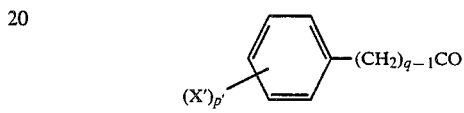

alkanoyl, formyl, $R^2OCO$, 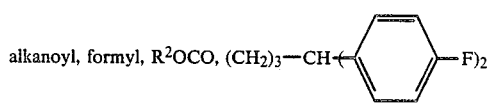

or diloweralkylphosphinylmethyl, wherein $R^2$, X′, p′ and q are as defined above, a 3-(piperidinyl)- or 3-(pyrrolidinyl)-1H-indazole of formula 18, i.e., a compound wherein the nitrogen atom of the 3-(piperidinyl) or 3-(pyrrolidinyl) groups and the nitrogn atom occupying the 1-position of the indazole system are unsubstituted, is treated with an alkanoyl or formyl halide, i.e., an alkanoyl or formyl iodide, bromide or chloride, or halide of the formulas

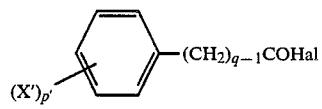

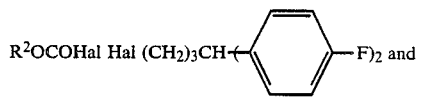

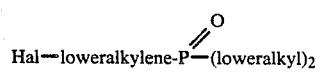

wherein $R^2$, X′, p′ and q are as above and Hal is iodo, bromo or chloro, in a halocarbon such as dichloromethane or trichloromethane, or a polar aprotic solvent, such as dimethylformamide, dimethylacetamide or hexamethylphosporamide, in the presence of an acid scavenger, such as sodium or potassium carbonate or sodium or potassium bicarbonate, to provide a 3-(piperidinyl)- or 3-(pyrrolidinyl)-1H-indazole of formula 19 wherein R, X, m, n and p are as above. Trichloromethane and dimethylformamide are the preferred solvents, and potassium bicarbonate is the preferred scavenger.

To minimize formation of disubstituted products, i.e., compounds of formula 20 wherein R, X, m, n and p are as above, one generally performs the acylation reaction, i.e., the conversion of 18 to 19, at about ambient temperature, at which temperature only minor amounts of the N,N'-disubstituted product 20 are usually formed. The N-substituted and N,N'-disubstituted products 19 and 20 may be separated by conventional techniques such as recrystallization. In the event substantial amounts of the N,N'-disubstituted product are formed, or the separation proves to be difficult, one may transform the N,N'-disubstituted compound 20 to the monosubstituted product 19 by alcoholysis. The alcoholysis is conveniently accomplished by means of an alkali metal alkoxide in an alkanol. Suitable alkali metal alkoxides include lithium, sodium or potassium methoxide, ethoxide, 1-propoxide and the like. Suitable alkanols include methanol, ethanol, 1-propanol and the like. Sodium methoxide in methanol is preferred.

To provide the 1H-indazole 10 wherein R is hydrogen and X, m, n and p are as defined above an N-unsubstituted benzoylpiperidine 7 or N-unsubstituted benzoylpyrrolidine 7 is cyclized with hydrazine hydrate by the hereinbeforedescribed process.

Alternatively, to provide the 1H indazole 10 wherein R is hydrogen and X, m, n and p are as defined above, compound 19 where R is loweralkanoyl or lower alkoxycarbonyl is subjected to hydrolysis at 50° to 150° C. for 3 to 16 hours in the presence of aqueous alkanol e.g. $C_2H_5OH$, $HO(CH_2)_2OH$, etc.

3-(Piperidinyl)- or 3-(pyrrolidinyl)-1H-indazol systems of formula 1 wherein R is cyano are also prepared by treating a 1-substituted 1H-indazole of formula 11 wherein R is alkyl and $R^1$ is formyl, alkanoyl or

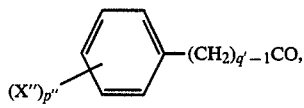

wherein X", p" and q' are as above with cyanogen bromide or chloride as hereinafterdescribed. For example, treatment of a solution of 1-benzoyl-3-(1-methyl-4-piperidinyl)-1H-indazole (11 wherein R is methyl, $R_1$ is benzoyl, X is hydrogen, m and n are 2 and p is 1) and chloroform with cyanogen bromide in the presence of potassium carbonate provides 4-(1-benzoyl-1H-indazol-3-yl)piperidine-1-carbonitrile (1 wherein R is cyano, $R^1$ is benzoyl, X is hydrogen, m and n are 2 and p is 1).

To prepare 1-substituted 1H-indazoles of formula 1 wherein $R^1$ is formyl, alkanoyl, cycloalkylalkanoyl

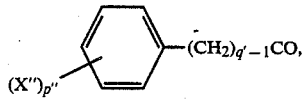

$R^{2'}OCO$ or $R^5CO$ wherein $R^{2'}$, $R^5$, X", p" and q' are as above, a 1-unsubstituted 1H-indazole 8 wherein R is as above, with the proviso that R is not hydrogen, and X, m, n and p are as before, is treated, respectively, with a formyl, alkanoyl or cycloalkylalkanoyl chloride, bromide or iodide, a compound of the formula

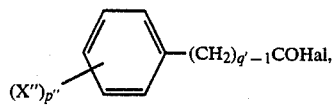

$R^{2'}OCOHal$ or $R^5COHal$ wherein $R^{2'}$, $R^5$, X", p" and q' are as above and Hal is iodo, bromo or chloro, or the corresponding acid anhydrides thereof, at an elevated temperature of about the reflux temperature of the reaction medium. For example, treatment of a 1H-indazole 8 wherein R is methyl with acetic anhydride at the reflux temperature of the reaction mixture affords a 1-acetyl-1H-indazole 14 wherein $R^2$ is methyl, and treatment of a 1H-indazole 8 wherein R is methyl with benzoyl chloride at a reaction temperature of about 100° C. yields a 1-benzoyl-1H-indazole 14 wherein $R^2$ is phenyl.

Alternatively, the synthesis of 1-substituted 1H-indazoles of formula 1 wherein $R^1$ is formyl, alkanoyl, cycloalkylalkanoyl,

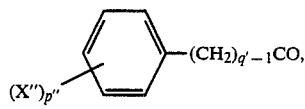

$R^2OCO$ or $R^5CO$, wherein $R^2$, $R^5$, X', p' and q are as above, is accomplished by contacting a formyl, cycloalkylalkanoyl or alkanoyl halide or compound of the formula

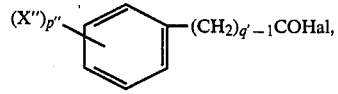

$R^{2'}OCOHal$ or $R^5COHal$ wherein $R^{2'}$, $R_5$, X", p" and q' are as above, with a 1-unsubstituted-1H-indazole 8 in a halocarbon such as dichloromethane or trichloromethane, preferably trichloromethane, in the presence of an acid scavenger such as sodium or potassium carbonate, or sodium or potassium bicarbonate, preferably potassium carbonate. The reaction proceeds readily at moderate temperatures. To promote the conversion however, elevated temperatures, i.e., the reflux temperature of the reaction medium, are generally employed.

To provide 1-substituted 1H-indazoles 11, wherein $R^1$ is

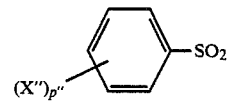

wherein X" and p" are as described hereinbefore, a 1-unsubstituted 1H-indazole 8 is treated with a benzenesulfonyl halide of the formula

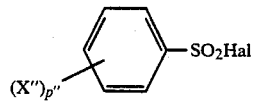

wherein X" and p" are as described hereinbefore and Hal is chloride or bromide at an elevated temperature within the range of about 80° to about 150° C., a reaction temperature of about 100° C. being preferred.

1H-Indazoles of formula 11 wherein $R^1$, X, m, n and p are as above and R is hydrogen are prepared from 1H-indazoles of formula 11 wherein $R^1$, X, m, n and p are as above and R is alkyl by the conversion of a 3-(1-alkylpiperidinyl)- or 3-(1-alkylpyrrolidinyl)-1H-indazole 11 wherein R is alkyl and $R^1$, X, m, n and p are as above to a 3-(1-cyanopiperidinyl)- or 3-(1-cyanopyrrolidinyl)-1H-indazole 11, wherein R is cyano and R¹, X, m and p are as above, followed by removal of the cyano group to a 1H-indazole of formula 11 wherein R is hydrogen and R¹, X, m, n and p are as above. The conversion of a 1-alkylpiperidine 11 or 1-alkylpyrrolidine 11 wherein R is alkyl to the corresponding 1-cyano compound 11 wherein R is cyano is accomplished by treating the alkylpiperidine 11 or alkylpyrrolidine 11 with a cyanogen halide such as cyanogen bromide or chloride in the presence of a acid acceptor such as sodium or potassium carbonate or sodium or potassium bicarbonate in a suitable solvent. Suitable solvents include halocarbons such as dichloromethane, trichloromethane, 1,2-dichloroethane and the like, and dipolar aprotic solvents such as dimethylformamide, dimethylacetamide, hexamethylphosphoramide, and dimethylsulfoxide. Cyanogen bromide is the preferred halide and dimethylsulfoxide containing potassium carbonate is the preferred reaction medium. The conversion temperature is not critical. To avoid side-reactions, however, it is preferred to perform the reaction at reduced temperatures between about 0° and about 30° C. A temperature of about 25° C. is preferred.

The removal of the cyano group of compounds of formula 11 wherein R is cyano may be effected directly under conventional hydrolytic conditions, utilizing for example, aqueous organic acids such as aqueous acetic acid, or mineral acids such as dilute hydrochloric acid or sulfuric acid.

1H-Indazoles of the formula 11 wherein R¹, X, m, n and p are as above, with the proviso that R₁ is not hydrogen, and R is formyl are prepared from 1H-indazoles of formula 11 wherein R¹, X, m, n and p are as above, with the proviso that R¹ is not hydrogen, by reaction thereof with formic acid in the presence of a mixture of formic acid and acetic anhydride at a temperature of 50° to 100° C. for 1 to 16 hours in the presence of the ethereal solvent. The presence of the ethereal solvent is not necessary, however.

N-Unsubstituted 1H-indazoles, i.e., 1H-indazoles of formula 18 wherein both the indazole and piperidine (or pyrrolidine) nitrogen atoms are unsubstituted, are prepared by an alternative synthesis involving the condensation of an appropriately substituted fluorobenzene of formula 15 wherein X and p are selected from the groups described above with an N-formyl- or N-alkanoyl-(piperidinyl)- or (pyrrolidinyl)carbonyl halide of formula 16 wherein R is formyl or alkanoyl and Hal is chloro or bromo, followed by cyclization of the resulting (2-fluorobenzoyl)piperidine 17 or (2-fluorobenzoyl)pyrrolidine 17 to the 1H-indazole 18.

To provide a N-loweralkyl-N'-hydroxyloweralkyl-3-(piperidinyl)-1H-indazole 11 or a N-loweralkyl-N'-hydroxyloweralkyl-3-(pyrrolidinyl)-1H-indazole 11, i.e., a compound of formula 11 wherein R is loweralkyl and R¹ is hydroxyloweralkyl, a N-loweralkyl-N'-loweralkoxycarbonylloweralkyl-3-(piperidinyl)-1H-indazole 11 or a N-loweralkyl-N'-loweralkoxycarbonylloweralkyl-3-(pyrrolidinyl)-1H-indazole 11, i.e., a compound of formula 11 wherein R is loweralkyl and R¹ is loweralkoxycarbonylloweralkyl, is reduced with an alkali metal aluminum hydride such as, for example, lithium aluminum hydride, in an ethereal solvent such as for example, tetrahydrofuran, at the reflux temperature of the reaction mixture.

To provide a N'-hydroxyloweralkyl-3-(piperidinyl)-1H-indazole 11 or a N'-hydroxyloweralkyl-3-(pyrrolidinyl)-1H-indazole 11, i.e., a compound wherein R¹ is hydroxyloweralkyl and R is a group as hereinbeforedefined other than loweralkyl, a N-loweralkyl-N'-hydroxyloweralkyl-3-(piperidinyl)-1H-indazole 11 or a N-loweralkyl-N'-hydroxyloweralkyl-3-(pyrrolidinyl)-1H-indazole 11, i.e., a compound wherein R is other than loweralkyl and R¹ is hydroxyloweralkyl is transformed by the processes as hereinbeforedescribed, involving the removal of the loweralkyl group and, for example, alkylation or acylation of the N-unsubstituted compound, so obtained.

The condensation of fluorobenzene 15 with a carbonyl halide 16 is accomplished under Friedel-Crafts conditions as described in U.S. Pat. No. 4,355,037, granted Oct. 19, 1982.

The cyclization of a (2-fluorobenzoyl)piperidine 17 or (2-fluorobenzoyl)pyrrolidine 17 to a 1H-indazole 18 is performed with hydrazine hydrate in an alkanol at an elevated temperature, conditions under which the N-formyl or n-alkanoyl group of the piperidine or pyrrolidine ring is removed. Suitable alkanols include ethanol, 2-propanol, 1-butanol, 3-pentanol and the like. 1-Butanol is preferred. A cyclization temperature of the boiling point of the reaction medium is also preferred.

To preserve the N-acyl group of the piperidine or pyrrolidine ring, one may cyclize the hydrazone of a (2-fluorobenzoyl)piperidine 17 or (2-fluorobenzoyl)pyrrolidine 17, prepared by methods well-known in the art, by means of an alkali metal hydride, for example, sodium hydride, in a dipolar aprotic solvent, for example, diemthylformamide, at an elevated temperature of about 80°–120° C.

1H-Indazoles substituted at the 1-position by a loweralkyl group, i.e., compounds of formula 1 wherein R¹ is loweralkyl, are also prepared by reducing a 1-loweralkanoyl- or 1-loweralkoxy-carbonyl-3-(piperidinyl)- or 3-(pyrrolidinyl)-1H-indazole of formula 19, the synthesis of which is hereinbeforedescribed, by an alkali metal aluminum hydride such as for example, lithium aluminum hydride, in an ethereal solvent such as tetrahydrofuran, at the reflux temperature of the reaction medium.

1H-Indazoles of formula 11 wherein R¹, X, m, n, and p are as above and R is

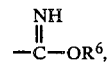

where R⁶ is as previously defined, are prepared from 1H-indazoles of formula 11 wherein R¹, X, m, n and p are as above and R is cyano, of from 1-substituted 1H-indazoles of formula 14 where R², m, n, and p are as above and R is cyano, by reaction with an alcohol of the formula R⁶OH, typically in the presence of an alkali metal cyanide such as potassium cyanide. Ordinarily the reaction is conducted in the presence of alkali metal cyanide such as potassium cyanide and an excess amount of the alcohol R⁶OH, which also works as a reaction medium. A typical reaction condition is refluxing the reaction mixture for several hours and then further continuing the reaction at ambient temperature for 10–20 hours. In an alternative procedure, the 1H-indazole, above, where R is cyano, is reacted with an alcohol of the formula R⁶OH in the presence of (usually only catalytic amount) of an alkali metal alkoxide of formula MOR⁶ where M is an alkali metal, preferably sodium. Usually sodium metal is added to an excess amount of an alcohol of formula R⁶OH to form the sodium alkoxide of formula NaOR$^6$. Thereafter the cyano substituted 1H-indazole 11 is added to the mixture and if necessary the mixture is heated slightly until a uniform solution is formed.

1H-Indazoles of formula 11 wherein R$^1$, X, m, n, and p are as above and R is

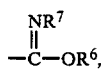

where R$^7$ is other than hydrogen, are prepared from 1H-indazoles of formula 11 wherein R$^1$, X, m, n, and p are as above and R is hydrogen or from compounds 14 above, R, m, n, and p are as above and R is hydrogen by reaction with an isocyanate or isothiocyanate of the formula R$^7$—N=C=Y (Y is oxygen or sulfur) to afford a urea derivative

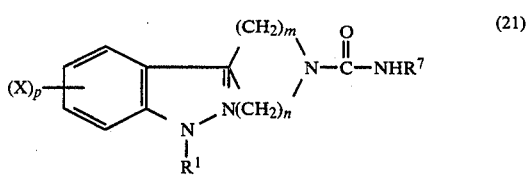 (21)

This reaction is typically conducted in a suitable medium such as benzene or toluene at a temperature between room temperature and the reflux temperature, for example by refluxing the reaction mixture for 1-24 hours. Suitable reagents are, for example, methylisothiocyanate, methylisocyanate, phenylisocyanate and other isothiocyanates or isocyanates. Compound 21 is then halogenated, e.g. chlorinated by the use of an inorganic halide, e.g. SOCl$_2$, PCl$_3$, etc. to form compound 22

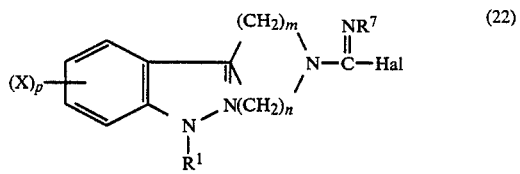 (22)

This reaction, e.g., chlorination, is typically conducted by refluxing a mixture comprising compound 21, the inorganic halide, e.g. PCl$_5$, and a suitable medium such as chlorobenzene until the evolution of the hydrogen halide, e.g. hydrogen chloride, ceases. Finally compound 22 is reacted with an equivalent amount of an alkali metal alkoxide of an alcohol R$^6$OH to afford compound 11 where R is

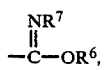

where R$^7$ is as defined above and is other than hydrogen. This reaction is typically conducted in either the alcohol R$^6$OH as a solvent or in an inert solvent such as toluene or dimethylformamide (DMF) at reflux temperature (in the case of R$^6$OH or toluene, for instance) or an elevated temperature (in the case of DMF, for instance), for a suitable length of time such as for example 0.5 to 24 hours.

1H-Indazoles of formula 11 wherein R$^1$, X, m, n and p are as above and R is

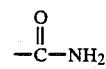

are prepared from 1H-indazoles of formula 11 wherein R$^1$, X, m, n and p are as above and R is cyano, by hydrolysis thereof. This is a conventional hydrolysis of a nitrile group and is typically conducted in the presence of base, e.g. NaOH, or acid e.g. H$_2$SO$_4$ (dilute). The compounds are also available from 1H-indazoles of the formula 11 wherein R', X, m, n, and p are as defined above and R is hydrogen by reacting them with nitrourea preferably in a polar solvent as, for example, ethanol or acetone, preferably at a temperature between room temperature and the refluxing temperature of the reaction mixture.

1H-Indazoles of the formula 11 wherein R', X, m, n and p are as defined above and R is

(Y, R$^8$ and R$^9$ are as defined above, however, R$^8$=R$^9$=hydrogen) are prepared from 1H-indazoles, of the formula 11 wherein R', X, m, n and p are as defined above and R is hydrogen by reacting them with a halogenide of the formula

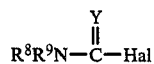

wherein R$^8$, R$^9$ and Y are as defined above and Hal denotes halogen, preferably chlorine. This reaction is typically conducted in a suitable medium such as benzene or toluene at a temperature between room temperature and refluxing temperature preferably in the presence of a base such as a trialkylamine.

In an alternative procedure, referring to Reaction Schemes A and B, C & D, the 1-alkyl-(2-fluorobenzoyl)piperidine 5, or -pyrrolidine 5, the 1-phenoxycarbonyl-(2-fluorobenzoyl)piperidine or -pyrrolidine 6, the (2-fluorobenzoyl)-piperidine or -pyrrolidine 7, the N-substituted benzoyl piperidine or -pyrrolidine 9, or the (2-fluorobenzoyl)piperidine or -pyrrolidine 17 are reacted with a substituted hydrazine of the formula H$_2$N-NHR$^1$ to form a compound of the formula

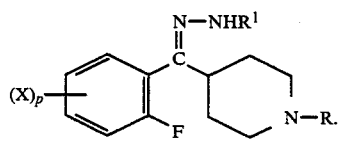 (21a)

The reaction is typically carried out at 40° to 110° C. for 2 to 16 hours in the presence of an alkanoic solvent, e.g. ethanol, isopropanol, etc. The resultant compound 21a is then cyclized by treatment with a strong base, such as NaH, KO-t-C$_4$H$_9$, NaNH$_2$, etc. at a temperature of 25° to 120° C. for 3 to 16 hours in the presence of an aprotic solvent, e.g. DMF, THF, etc. to form compound of the formula

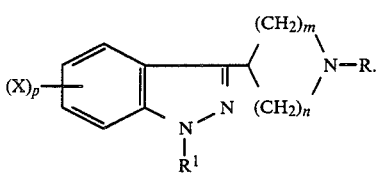

(22a)

1H-Indazoles of the formula 11 wherein $R^1$, X, m, n and p are as defined above and R is

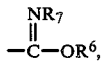

$$-\overset{NR_7}{\underset{\|}{C}}-OR^6,$$

where $R^6$ is as defined above, and $R^7$ is hydrogen, are prepared from 1H-indazoles of the formula 11, wherein R is cyano, by reacting them with an alcoholate of the formula $MOR^6$, where M is a metal, e.g. $NaOR^6$. This reaction is typically conducted at a temperature of 25° to 100° C., for 1 to 16 hours, in an alkanoic ($R^6OH$) solvent, e.g. methanol, ethanol, etc. In addition, the resultant compounds, where R is $-C-OR^6$ can be converted to compounds 11 where R is

$$\overset{O}{\underset{\|}{C}}-NHR^7$$

by reaction thereof with an acid, e.g. HBr, at 50° to 90° C. for 13 to 16 hours.

1H-Indazoles of the formula 11 wherein $R^1$, X, m, n and p are as above and R is

$$\overset{Y}{\underset{\|}{C}}-NHR^9,$$

where $R^9$ is as previously defined, are prepared from 1H-indazoles of the formula 11 wherein $R^1$, X, m, n and p are as above and R is hydrogen, by reaction thereof with an isocyanate or isothiocyanate of the formula $R^9-N=C=Y$ where R9 and Y are as previously defined. The reaction is typically carried out at a temperature of 25° to 110° C. for 1 to 16 hours in a hydrocarbon solvent, e.g. benzene, toluene, etc.

1H-Indazoles of the formula 11 wherein R', X, m, n and p are as above and R is

$$\overset{O}{\underset{\|}{C}}-NH_2$$

are prepared from 1H-Indazoles of formula 11 wherein R', X, m, n and p are as above and R is hydrogen by reaction thereof with nitrourea at a temperature of 25° to 100° C. for 1 to 16 hours in a polar solvent e.g. ethanol, DMF, etc.

The synthesis of 3-(3-haloalkyl)-6-fluoro-1,2-benzisoxazoles, 4,4-bis(4-fluorophenyl)butyl halides, 3-(phenylsulfonylalkyl)indoles and 3-(alkylphenylsulfonylalkyl)indoles, 1-(3-haloalkyl)1,2-dihydro-2H-benzimidazol-2-ones; and 4-fluorobenzoylalkyl halides ethylene glycol ketals requisite precursors for the preparation of 3-(4-piperidinyl)-1H-indazoles and 3-(3-pyrrolidinyl)-1H-indazoles of the present invention, substituted at the indazole and/or piperidine or pyrrolidine nitrogen atoms, are described in U.S. Pat. No. 4,352,811, granted Oct. 5, 1982.

The 3-(piperidinyl)- and 3-(pyrrolidinyl)-1H-indazoles of the present invention are useful for treating psychoses by virtue of their ability to elicit an antipsychotic response in mammals.

Antipsychotic activity is determined in the climbing mice assay by methods similar to those described by P. Protais, et al., Psychophramacol., 50, 1 (1976) and B. Costall, Eur. J. Pharmacol. 50, 39 (1978).

The subject CK-1 male mice (23-27grams) are group-housed under standard laboratory conditions. The mice are individually placed in wire mesh stick cages (4"×4" by 10") and are allowed one hour for adaptation and exploration of the new environment. Then apomorphine is injected subcutaneously at 1.5 mg/kg, a dose causing climbing in all subjects for 30 minutes. Compounds to be tested for antipsychotic activity are injected intraperitoneally (i.p.) 30 minutes prior to the apomorphine challenge at a screening dose of 10 mg/kg.

For evaluation of climbing, 3 readings are taken at 10, 20, and 30 minutes after apomorphine administration according to the following scale:

| Climbing Behavior | Score |
| --- | --- |
| Mice with: | |
| 4 paws on bottom (no climbing) | 0 |
| 2 paws on the wall (rearing) | 1 |
| 4 paws on the wall (full climb) | 2 |

Mice consistently climbing before the injection of apomorphine will be discarded.

With full-developed apomorphine climbing, the animals are hanging onto the cage walls, rather motionless, over longer periods of time. By contrast, climbs due to mere motor stimulation usually only last a few seconds.

The climbing scores are individually totaled (maximal score: 6 per mouse over 3 readings) and the total score of the control group (vehicle intraperitoneally-apomorphine subcutaneously) is set to 100%. $ED_{50}$ values with 95% confidence limits, calculated by a Linear Regression Analysis of some of the instant 3-(piperidinyl)-1H-indazoles and 3-(pyrrolidinyl)-1H-indazoles as well as standard antipsychotics, are presented in Table 1.

TABLE 1

| COMPOUND | ANTIPSYCHOTIC ACTIVITY ($ED_{50}$ mg/kg, i.p.) |
| --- | --- |
| 3-(1-methyl-4-piperidinyl)-1H—indazole | 4.5 |
| 3-(1-methyl-4-piperidinyl)-1-trichloroethoxycarbonyl-1H—indazole | 46% @ 10 mg/kg* |
| 1-ethyl-3-(1-methyl-4-piperidinyl)-1H—indazole | 41% @ 10 mg/kg* |
| 1-acetyl-3-(1-methyl-4-piperidinyl)-1H—indazole | 5.4 |
| 1-benzoyl-3-(1-methyl-4-piperidinyl)-1H—indazole | 6.5 |
| 1-benzoyl-6-fluoro-3-(1-methyl-4-piperidinyl)-1H—indazole | 1.8 |
| 3-(1-[4,4-bis(4-fluorophenyl)-butyl]-4-piperidinyl)-1H—indazole | 7.4 |
| 1-cyclopropylmethyl-3-(1-methyl-4-piperidinyl)-1H—indazole | 36% @ 10 mg/kg* |
| haloperidol (standard) | 0.11 |

TABLE 1-continued

| COMPOUND | ANTIPSYCHOTIC ACTIVITY (ED$_{50}$ mg/kg, i.p.) |
|---|---|
| sulpiride (standard) | 14.5 |

*% decrease in climbing score at indicated dose, i.p.

Antipsychotic response is achieved when the present 3-(piperidinyl)- and 3-(pyrrolidinyl)-1H-indazoles are administered to a subject requiring such treatment at an effective oral, parenteral or intravenous dose of from 0.01 to 50 mg/kg of body weight per day. A particularly preferred effective amount is about 25 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

The 3-(piperidinyl)- and 3-(pyrrolidinyl)-1H-indazoles of the present invention are useful as analgetics due to their ability to alleviate pain in mammals. The analgetic utility is demonstrated in the phenyl-p-quinone writhing assay in mice, a standard assay for analgesia [Proc. Soc. Exptl. Biol. Med., 95, 729 (1957)]. Thus, for instance, the subcutaneous (s.c.) dose effecting an approximately 50% inhibition of writhing (ED$_{50}$) in mice produced in this assay is as follows:

| COMPOUND | ED$_{50}$ mg/kg, s.c. |
|---|---|
| 3-(1-methyl-4-piperidinyl)-1H—indazole | 0.26 |
| 1-ethyl-3-(1-methyl-4-piperidinyl)-1H-indazole | 0.65 |
| 1-acetyl-3-(1-methyl-4-piperidinyl)-1H—indazole | 0.71 |
| 1-benzoyl-3-(1-methyl-4-piperidinyl)-1H—indazole | 0.85 |
| 1-phenylmethyl-3-(1-methyl-4-piperidinyl)-1H—indazole | 75% @ 20 mg/kg* |
| 3-[1-[4,4-bis(4-fluorophenyl)-1-butyl]-4-piperidinyl]-1H—indazole | 96% @ 20 mg/kg* |
| 1-cyclopropylmethyl-3-(1-methyl-4-piperidinyl)-1H—indazole | 31% @ 20 mg/kg* |
| | 1.1 |
| 1-[3-(dimethylamino)propyl]-3-(1-methyl-4-piperidinyl)-1H—indazole | 15% @ 20 mg/kg* |
| 1-[4-(trifluoromethyl)phenyl]-3-(1-methyl-4-piperidinyl)-1H—indazole | 9.8 |
| 1-benzoyl-6-fluoro-3-(1-methyl-4-piperidinyl)-1H—indazole | 0.17 |
| propoxyphene (standard) | 3.9 |
| pentazocine (standard) | 1.3 |

*inhibition of writhing at indicated dose, s.c.

Analgesia production is achieved when the present 3-(piperidinyl)- and 3-(pyrrolidinyl)-1H-indazoles are administered to a subject requiring such treatment as an effective oral, parenteral or intravenous dose of from 0.01 to 100 mg/kg of body weight per day. A particularly effective amount is about 5 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and that they do not, to any extent, limit the scope or practice of the invention.

The 3-(piperidinyl)- and 3-(pyrrolidinyl)-1H-indazoles of the present invention are also useful as antidepressants by virtue of their ability to elicit an antidepressant response in mammals. The antidepressant activity is demonstrated in the tetrabenazine induced ptosis assay in mice [International Journal of Neuropharmacology, 8, 72 (1969)], a standard assay for antidepressant activity. Thus, for example, the intraperitoneal (i.p.) dose effecting an estimated 50% inhibition of ptosis (ED$_{50}$) in mice produced in this assay is as follows:

| COMPOUND | ED$_{50}$ (mg/kg, i.p.) |
|---|---|
| 1-(2-chlorophenyl)-3-(1-methyl-4-piperidinyl)-1H—indazole | 5.3 |
| 1-(2-chlorophenyl)-3-(4-piperidinyl)-1H—indazole | 5.9 |
| 1-(2-aminophenyl)-3-(1-methyl-4-piperidinyl)-1H—indazole | 19.2 |
| 1-(2-fluorophenyl)-3-(1-methyl-4-piperidinyl)-1H—indazole | 1.7 |
| 1-(3-fluorophenyl)-3-(1-methyl-4-piperidinyl)-1H—indazole | 5.0 |
| 6-fluoro-1-(2-fluorophenyl)-3-(1-methyl-4-piperidinyl)-1H—indazole | 6.3 |
| imipramine (standard) | 1.3 |
| amitriptyline (standard) | 1.5 |

Antidepressant response is achieved when the present 3-(piperidinyl)- and 3-(pyrrolidinyl)-1H-indazoles are administered to a subject requiring such treatment as an effective oral, parenteral or intravenous dose of from 0.01 to 50 mg/kg of body weight per day. A particularly preferred effective amount is about 10 mg/kg of body weight per day. It is to be understood, however, that for any particular subject, specific dosage regimens should be adjusted according to the individual need and the professional judgment of the person administering or supervising the administration of the aforesaid compound. It is to be further understood that the dosages set forth herein are exemplary only and they do not, to any extent, limit the scope or practice of the invention.

Compounds of the present invention include:
(a) 3-(3-pyrrolidinyl)-1H-indazole
(b) 3-(1-propenyl-4-piperidinyl)-1H-indazole
(c) 3-(4-cyclopropylmethyl-3-piperidinyl)-6-methyl-1-(2-pyrimidinyl)-1H-indazole
(d) 3-[1-butyl-3-pyrrolidinyl]-4-methoxy-1-(2-pyridinyl)-1H-indazole
(e) 3-(1-cyanomethyl-3-piperidinyl)-7-trifluoromethyl-1H-indazole
(f) 1-(4-fluorobenzoyl)-3-(4-piperidinyl)-5-nitro-1H-indazole
(g) 3-(1-acetyl-4-piperidinyl)-4-amino-1-(4-fluorobenzoylethyl)-1H-indazole
(h) 3-[1-(1-methylindol-3-propyl)-3-piperidinyl]-1H-indazole
(i) 1-formyl-3-(1-formyl-4-piperidinyl)-1H-indazole
(j) 5,6-dichloro-3-[1-(4-fluorobenzoylpropyl)-4-piperidinyl]-1-(propen-1-yl)-1H-indazole (k) 1-cyano-3-[1-(4-fluorobenzoylpropyl)-3-pyrrolidinyl]-1H-indazole ethylene ketal (l) 1-cyanomethyl-3-[1-(6-fluoro-1,2-benzisoxazol-3-propyl)-3-piperidinyl]-1H-indazole (m) 3-(1-phenoxycarbonyl-4-piperidinyl)-1-(4-picolinoyl)-1H-indazole (n) 3-[1-[1,3-dihydro-3-methyl-2-oxo-2H-benzimidazol-1-ylpropyl]-4-piperidinyl]-1-(2-thiazolylcarbonyl)-1H-indazole (o) 3-[1-(3-phenylpropyl)-4-piperidinyl]-1H-indazole (p) 3-[1-(1-methylindol-3-propyl)-3-piperidinyl]-1H-indazole The compounds of the invention are also useful as antihypertensive agents due to their ability to depress blood pressure in mammals. Antihypertensive activity is measured in the spontaneous hypertensive rat by the indirect tail cuff method described in "Methods in Pharmacology," A. Schwartz, Ed., Vol. I, Appleton-Century Crofts, New York, 1971, p. 135. In this procedure a group of five animals are treated orally (p.o.) for three days with the test compound in relation to the control group of the same number. The drop in blood pressure is measured on the third day following administration. The antihypertensive activities of some of the compounds, expressed as mm decrease in mean arterial blood pressure are given below:

| Compound | Dose (mg/kg p.o. of body weight, parenteral) | Decrease in Blood Pressure (mm Hg) |
| --- | --- | --- |
| 4-(1H—indazol-3-yl)piperidine-1-carboximidic acid methyl ester | 3 | 47 |
| 4-(6-fluoro-1H—indazol-3-yl)-piperidine-1-carboximidic acid methyl ester | 30 | 88 |
| guanethidine | 50 | 20 |

Blood pressure reduction is achieved when the compounds of the invention are administered to a subject requiring such treatment at an effective oral, parenteral or intravenous doses of from 0.1 to 50 mg/kg of body weight per day. A preferred effective dose within this range is from about 0.1 to 5 mg/kg of body weight per day. A particularly preferred effective amount is about 10 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

The compounds of the invention are also useful as anticonvulsants due to their anticonvulsant activity in mammals. Anticonvulsant activity is measured in the male mouse using the supramaximal electroshock (SES) assay described in *Arch. Int. Pharmacodyn.* 92: 97–107, 1952. In this procedure groups of animals are used. Drugs are prepared using distilled water and, if insoluble, a surfactant is added. Control animals receive vehicle. Drugs are routinely administered intraperitoneally (i.p). The dosage volume is 10 ml/kg. A primary screen is given a 30 minute pretreat. The animal's eyes are placed across the output terminals of an A.C. shocker that delivers 206 volts rms for 300 msec. Electrode paste coats the animals eye at the point of contact with the terminals. A compound is considered to give protection if the mouse does not exhibit extensor tonus. Protection is expressed as normalized percent inhibition relative to vehicle control.

A time response is carried out using six animals/group. Animals are tested at 30, 60 and 120 minutes postdrug. Additional time periods are tested if indicated by previous tests. When the peak activity time has been determined, a dose response is initiated using 10 animals/group at that time period. The $ED_{50}$ and 95% confidence interval are calculated by computer probit analysis.

Anticonvulsant activity is also measured using the metrazol lethality (MTZ). In this procedure groups of male mice are utilized. Test drugs are prepared using distilled water and, if insoluble, a suitable surfactant is added. The route of administration is i.p., but all administrations are in volumes proportional to 10 cc/kg.

For a time response, 25 animals (5/group) are administered drug i.p. at 15, 30, 60 and 90 minutes prior to Metrazol treatment. Control animals (2/group) receive vehicle. Metrazol (pentylenetetrazol) is prepared at a concentration of 225 mg/10 ml in distilled water. Metrazol is administered s.c. at 225 mg/kg in distilled water. Those animals alive 15 minutes after Metrazol injection are considered protected. The time period with the greatest percent protected is said to be that of peak drug activity.

A dose range is run in the same manner as a time response except that 50 animals (10/group) are tested at the peak time of drug activity. One group receives vehicle. An $ED_{50}$ is calculated by means of linear regression.

The anticonvulsant activities of some of the compounds are given below:

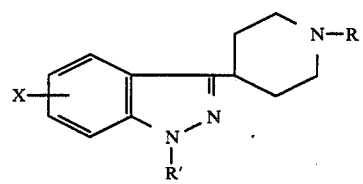
| Compound No. | X | R' | R | MTZ (ED$_{50}$ mg/kg i.p.) | SES |
|---|---|---|---|---|---|
| 1 | H | 2-fluorophenyl | CONHCH$_3$ | 49 | 37 |
| 2 | 6-fluoro | phenyl | CONHC$_6$H$_5$ | 20% @ 60 | 0% @ 60 |
| 3 | H | 4-CF$_3$-phenyl | CONH$_2$·HBr | 27.4 | 10.9 |
| 4 | 6-fluoro | phenyl | CONHCH$_3$ | 0% @ 60 | 64.9 |
| 5 | 6-fluoro | phenyl | CSNHC$_6$H$_5$ | 17% @ 60 | 0% @ 60 |
| 6 | H | 2-CF$_3$-phenyl | CONHCH$_3$ | 20% @ 60 | 44.9 |
| 7 | H | 4-CF$_3$-phenyl | COCH$_3$ | 60% @ 60 | 0% @ 60 |
| 8 | 6-Br | phenyl | COCH$_3$ | 0% @ 60 | 33% @ 60 |
| 9 | H | 4-F-phenyl | CONHCH$_3$ | 45.5 | 31.7 |
| 10 | H | 4-F-phenyl | COCH$_3$ | 45.5 | 35.3 |
| 11 | H | 4-F-phenyl | CONH$_2$ | 79.6 | 33.7 |

-continued

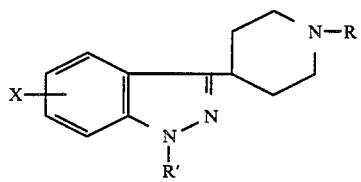

| Compound No. | X | R' | R | (ED$_{50}$ mg/kg i.p.) MTZ | SES |
|---|---|---|---|---|---|
| 12 | H | —⌬—CF$_3$ | CHO | 60.9 | 27.2 |
| 13 | H | —⌬—F | CHO | 40% @ 60 | 24.7 |
| 14 | 6-fluoro | —⌬ | CONH$_2$ | 39.9 | 34.9 |
| 15 | 6-chloro | —⌬ | CONH$_2$ | 31.2 | 48.1 |
| 16 | H | —⌬—CF$_3$ | CON(CH$_3$)$_2$ | 20% @ 60 | 20% @ 60 |

Anticonvulsant activity is achieved when the compounds of the invention, especially such compounds of the formula

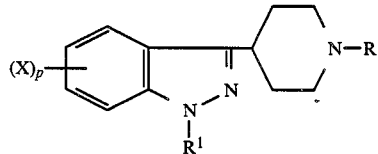

wherein R is formyl, loweralkanoyl, or $$-\overset{Y}{\underset{\|}{C}}-NR^8R^9;$$

R$^1$ is

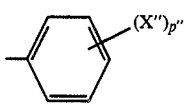

and p, p'', X, X'', Y, R$^8$ and R$^9$ are as defined above, are administered to a subject requiring such treatment at an effective oral, parenteral or intravenous dose of from 0.1 to 100 mg/kg of body weight per day. A preferred effective dose within this range is from about 5 to 50 mg/kg of body weight per day. A particularly preferred effective amount is about 20 mg/kg of body weight per day. It is to be understood, however, that for any particular subject, specific dosage regimens should be adjusted according to the individual need and the professional judgement of the person administering or supervising the administration of the compounds of the invention. It is to be further understood that the dosages set forth herein are examples only and that they do not, to any extent, limit the scope or practice of the invention.

Effective amounts of the present invention may be administered to a subject by any one of various methods, for example, orally as in capsules or tablets, parenterally in the form of sterile solutions or suspensions, and in some cases intravenously in the form of sterile solutions. The 3-(piperidinyl)- and 3-(pyrrolidinyl)-1H-indazoles of the present invention, while effective themselves, may be formulated and administered in the form of their pharmaceutically acceptable addition salts for purposes of stability, convenience or crystallization, increased solubility and the like.

Preferred pharmaceutically acceptable addition salts include salts of mineral acids, for example, hydrochloric acid, sulfuric acid, nitric acid and the like, salts of monobasic carboxylic acids such as, for example, acetic acid, propionic acid and the like, salts of dibasic carboxylic acids such as, for example, maleic acid, fumaric acid and the like, and salts of tribasic carboxylic acids such as, for example, carboxysuccinic acid, citric acid and the like.

Effective quantities of the compounds of the invention may be administered orally, for example, with an inert diluent or with an edible carrier. They may be enclosed in gelatin capsules or compressed into tablets. For the purpose of oral therapeutic administration, the aforesaid compounds may be incorporated with excipients and used in the form of tablets, troches, capsules, elixirs, suspensions, syrups, wafers, chewing gums and the like. These preparations should contain at least 0.5% of active compound, but may be varied depending upon the particular form and may conveniently be between 4% to about 70% of the weight of the unit. The amount of active compound in such composition is such that a suitable dosage will be obtained. Preferred compositions and preparations according to the present invention are prepared so that an oral dosage unit form contains between 1.0–300 milligrams of the active compound.

The tablets, pills, capsules, troches and the like may also contain the following ingredients: a binder such as microcrystalline cellulose, gum tragancanth or gelatin; an excipient such as starch or lactose, a distintegrating agent such as alginic acid, Primogel, corn starch and the like; a lubricant such as magnesium stearate or Sterotex; a glidant such as colloidal silicon dioxide; and a sweetening agent such as sucrose or saccharin or a flavoring agent such as peppermint, methyl salicylate, or orange flavoring may be added. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the active compounds, sucrose as a sweetening agent and certain preservatives, dyes and colorings and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 50% of the weight thereof. The amount of active compounds in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

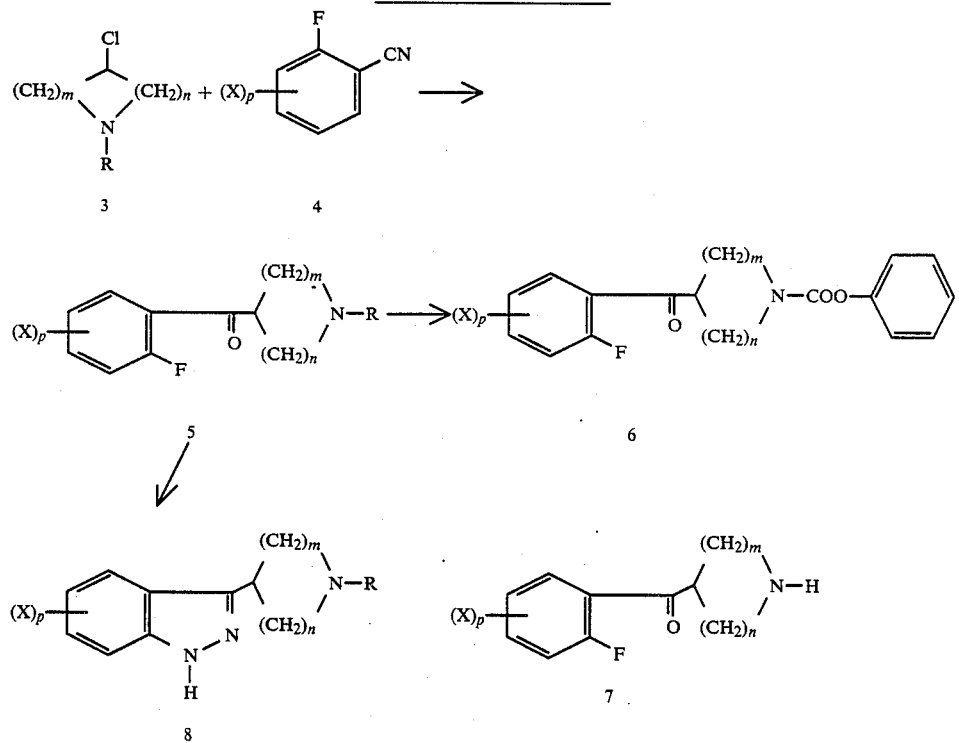

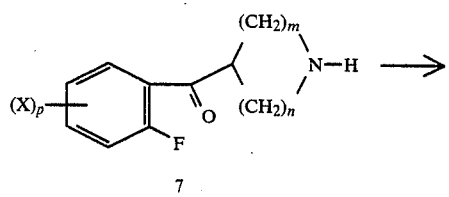

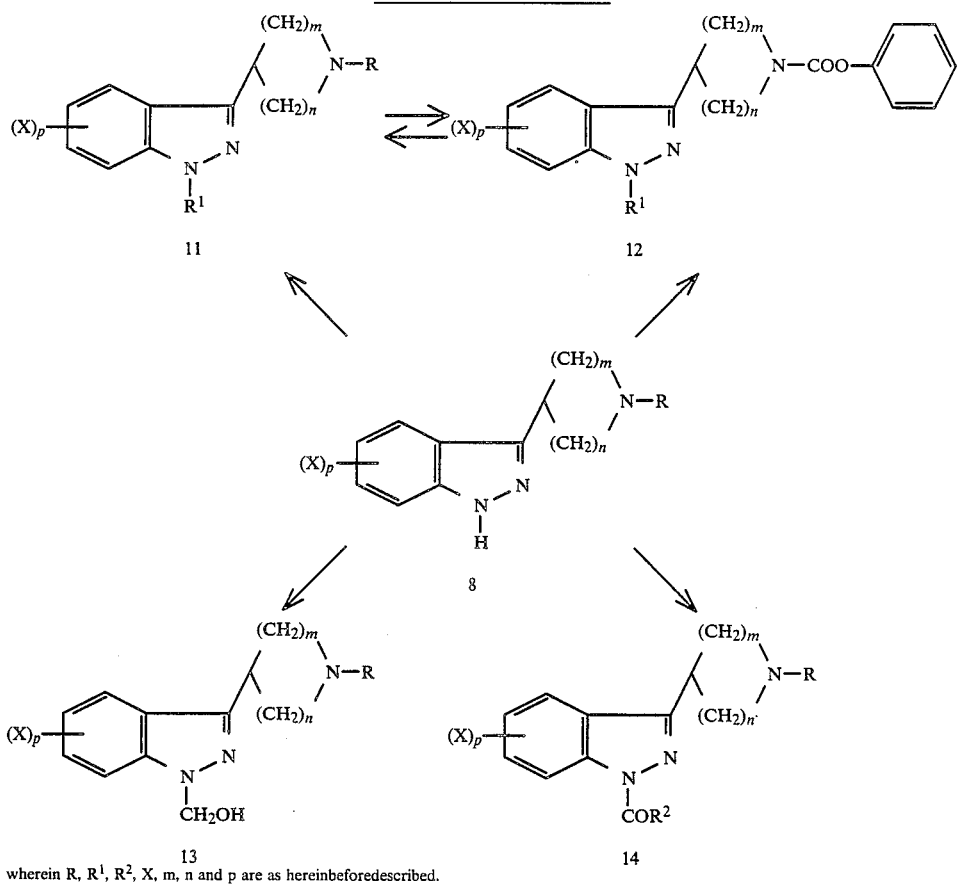
REACTION SCHEME C
wherein R, R¹, R², X, m, n and p are as hereinbefore described.
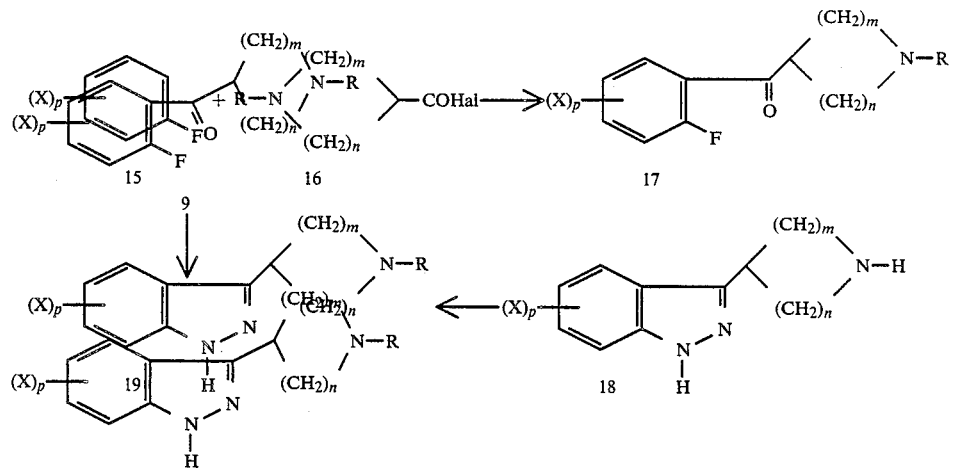
-continued
REACTION SCHEME M    REACTION SCHEME D
wherein R, X, m, n and p are as hereinbefore described.

-continued
REACTION SCHEME D

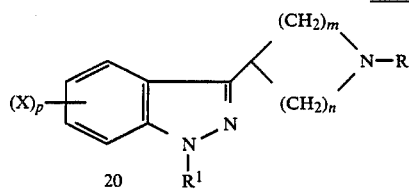

wherein R, $R^1$, X, Hal, m, n and p are as before.

The following examples are for illustrative purposes only and are not to be construed as limiting the invention. All temperatures are given in degrees centigrade (°C.).

EXAMPLE 1

4-(2-Fluorobenzoyl)-1-methylpiperidine hydrochloride

To a suspension of 7.6 g of magnesium turnings in 25 ml of tetrahydrofuran was added a few drops of ethyl bromide, with stirring under nitrogen. After the reaction began approximately 50.0 g of N-methyl-4-chloropiperidine in 125 ml of tetrahydrofuran was added dropwise at a rate such that moderate reflux was maintained. The reaction was heated under reflux for an additional hour. A solution of 37.2 g of o-fluorobenzonitrile in 30 ml of tetrahydrofuran was added dropwise. After completion of the addition the reaction mixture was heated under reflux for two hrs and stirred overnight at room temperature. The reaction mixture was poured into a solution of 85 g of ammonium chloride in 1200 ml of ice water and heated on a steam bath for 3 hrs. The mixture was cooled, extracted with benzene (3×, 250 ml) and dried over anhydrous sodium sulfate. Removal of the solvent under reduced pressure gave an oil. A 1.0 g-portion of the oil was dissolved in ether and a solution of ethereal hydrogen chloride was added. The precipitate was collected, dried and twice recrystallized from ethanol-ether to give 0.5 g (42%) of product, mp 167°-169° C.

ANALYSIS: Calculated for $C_{13}H_{17}ClFNO$: 60.58%C, 6.65%H, 5.43%N, 7.37%F. Found: 60.30%C, 6.78%H, 5.43%N, 7.59%F.

EXAMPLE 2

1-Phenoxycarbonyl-4-(2-fluorobenzoyl)piperidine

To a solution of 57.5 g of 4-(2-fluorobenzoyl)-1-methyl piperidine and 68.7 g of potassium carbonate in 750 ml of toluene was added with stirring 47 g of phenylchloroformate. The reaction mixture was heated under reflux for 5 hrs, cooled to room temperature, filtered, and the solvent removed under reduced pressure to give an oil. Trituration of the oil with hexane gave 48.6 g (46%) of product. Recrystallization of 1.0 g of product from ethanol-water (2×) and from ethanol gave the analytical sample, mp 95°-96° C.

ANALYSIS: Calculated for $C_{19}H_{18}FNO_3$: 69.71%C, 5.54%H, 4.28%N, 5.81%F. Found: 69.45%C, 5.67%H, 4.13%N, 6.10%F.

EXAMPLE 3

4-(2-Fluorobenzoyl)piperidine hydrochloride

A solutiion of 40.5 g of 1-phenoxycarbonyl-4-(2-fluorobenzoyl)piperidine, 500 ml of ethanol and 500 ml of 30% of potassium hydroxide solution was stirred at a temperature slightly below reflux overnight. The reaction mixture was cooled to room temperature, diluted with 250 ml of water, and the ethanol partially removed under reduced pressure. The aqueous suspension was extracted with ether (2×150 ml) and the ether fraction subsequently extracted with 1N hydrochloric acid (2×200 ml). The aqueous solution was basified with 25% sodium hydroxide solution, extracted with ether (2×150 ml) and dried over anhydrous sodium sulfate. The solvent was removed under reduced pressure to give an oil. The oil was dissolved in a minimum amount of ethanol and a solution of ethereal hydrogen chloride was added dropwise until a precipitate formed. The solid was collected and dried to give 9.7 g (40%) of product. Recrystallization twice from ethanol-ether gave the analytical sample, mp 185°-187° C.

ANALYSIS: Calculated for $C_{12}H_{15}ClFNO$: 59.14%C, 6.20%H, 5.74%N, 7.80%F. Found: 58.90%C, 6.36%H, 5.50%N, 7.56%F.

EXAMPLE 4

3-(1-Methyl-4-piperidinyl)-1N-indazole

An autoclave was charged with 10.0 g of 4-(2-fluorobenzoyl)-1-methylpiperidine and 14 ml of hydrazine hydrate. The reaction was heated at 150° for 20 hours, cooled, and poured into water. The resultant solid was collected. The solid was recrystallized twice from toluene to yield 2.4 g (23.7%) of product, mp 168°-170° C.

ANALYSIS: Calculated for $C_{13}H_{17}N_3$: 72.52%C, 7.96%H, 19.52%N. Found: 72.60%C, 8.04%H, 19.51%N.

EXAMPLE 5

3-[1-[4,4-bis(4-Fluorophenyl)butyl]-4-piperidinyl]-1H-indazole

A mixture of 10.0 g of 4-(2-fluorobenzoyl)piperidine, 16.9 g of potassium carbonate, 20.8 g of 4-chloro-1,1-bis(4-fluorophenyl)butane, 250 ml of dimethylformamide and a few crystals of potassium iodide was heated at 90° for 8 hrs with stirring. The reaction mixture was poured into water and extracted with ethyl acetate. The ethyl acetate extract was washed with water, dried over anhydrous magnesium sulfate and the solvent removed in vacuo to yield an oil. The oil was dissolved in ether, and oxalic acid was added. Recrystallization of the resultant solid from ethanol gave 10.6 g (34.6%) of 1-[4,4-bis(4-fluorophenyl)-1-butyl]-4-(2-fluorobenzoyl)-piperidine oxalate, mp 179°-181° C.

A solution of 8.0 g of 1-[4,4-bis(4-fluorophenyl)-1-butyl]-4-(2-fluorobenzoyl)piperidine and 110 ml of hydrazine hydrate was heated at 150° in an autoclave for 20 hrs, with stirring. The resultant solid was diluted with water, and the mixture extracted with dichloromethane. The dichloromethane was evaporated in vacuo to yield a solid. The solid was recrystallized from toluene to give 3.8 g (47.4%) of product, mp 154°–156° C.

ANALYSIS: Calculated for $C_{28}H_{29}F_2N_3$: 75.48%C, 6.56%H, 9.43%N. Found: 75.29%C, 6.59%H, 9.40%N.

EXAMPLE 6

1-Ethyl-3-(1-methyl-4-piperidinyl)-1H-indazole hydrobromide

To a stirred suspension of 0.86 g of sodium hydride (50% oil dispersion) in 50 ml of dimethylformamide was added, dropwise, 3.0 g of 3-(1-methyl-4-piperidinyl)-1H-indazole in 15 ml of hot dimethylformamide. The reaction mixture was stirred at ambient temperature and 1.34 ml of ethyl bromide in 10 ml of dimethylformamide was added, dropwise. The reaction was stirred overnight at ambient temperature and poured into water. The aqueous suspension was extracted with ethyl acetate (2×, 100 ml). The extracts were combined, washed with water, dried over anhydrous magnesium sulfate, and the solvent evaporated in vacuo to yield an oil. The oil was dissolved in a minimum amount of ethanol-ether, and a saturated solution of ether-hydrogen bromide was added. The salt was recrystallized from ethanol-ether to yield 2.4 g (52.8%) of product, mp 240°–242° C.

ANALYSIS: Calculated for $C_{15}H_{21}N_3HBr$: 55.56%C, 6.48%H, 12.96%N. Found: 55.39%C, 6.68%H, 12.59%N.

EXAMPLE 7

1-(4-Nitrophenyl)-3-(1-methyl-4-piperidinyl)-1H-indazole hydrochloride

To a stirred suspension, under nitrogen, of 0.86 g of sodium hydride (50% oil dispersion) was added, dropwise, 3.2 g of 3-(1-methyl-4-piperidinyl)-1H-indazole dissolved in 25 ml of hot dimethylformamide. After completion of the addition, the reaction mixture was stirred at ambient temperature for 1 hr and then 2.2 g of 1-fluoro-4-nitrobenzene was added, dropwise. The reaction mixture was stirred at ambient temperature for 16 hr and then poured into water. The resultant solid was collected and dried. The solid was dissolved in absolute ethanol and the solution was treated with saturated hydrogen chloride/ether solution to precipitate a salt. Recrystallization of the salt from methanol-ether (twice) gave 3.0 g (52%) of product, mp 272°–274° C.

ANALYSIS: Calculated for $C_{19}H_{20}N_4O_2.HCl$: 61.20%C, 5.68%H, 15.03%N. Found: 61.09%C, 5.70%H, 14.82%N.

EXAMPLE 8

1-[3-(Dimethylamino)propyl]-3-(1-methyl-4-piperidinyl)-1H-indazole difumarate

To a stirred suspension of 1.15 g of sodium hydride (50% oil dispersion) in 30 ml of dimethylformamide, under nitrogen, was added dropwise 4.3 g of 3-(1-methyl-4-piperidinyl)-1H-indazole dissolved in 30 ml of hot dimethylformamide. After stirring at ambient temperature for 1 hr, a solution of 3.3 g of dimethylaminopropylchloride in 30 ml of toluene was added dropwise. The reaction was then heated at 60° for 1 hr and then stirred at ambient temperature for 16 hrs. The reaction mixture was poured into water and the aqueous suspension was extracted with ethyl acetate (3×150 ml). The organic extracts were combined, washed with water, brine, dried over anhydrous magnesium sulfate, and the solvent evaporated in vacuo to yield an oil. The oil was dissolved in 25 ml of acetonitrile and 4.6 g of fumaric acid was added. The mixture was warmed on the steam bath (ca. 15 min), and then left at ambient temperature for 15 hrs. The resultant solid was filtered and recrystallized from dimethylformamide (thrice) with cooling (ca. 5°) to yield 1.4 g (18.7%) of product, mp 161°–163° C.

ANALYSIS: Calculated for $C_{18}H_{28}N_4.2C_4H_4O_4$: 58.61%C, 6.81%H, 10.52%N. Found: 58.82%C, 6.91%H, 11.51%N.

EXAMPLE 9

3-(1-Methyl-4-piperidinyl)-1-[4-(trifluoromethyl)-phenyl]-1H-indazole hydrochloride To a stirred suspension of 1.15 g of sodium hydride (50% oil dispersion) in 30 ml of dimethylformamide, under nitrogen, was added dropwise 4.3 g of 3-(1-methyl-4-piperidinyl)-1H-indazole dissolved in 30 ml of hot dimethylformamide. The reaction mixture was stirred at ambient temperature for 1 hr and then 3.9 g of 4-fluorobenzotrifluoride was added. The temperature was raised to 90° and held there for 16 hrs. The reaction mixture was poured into water and the aqueous suspension extracted with ethyl acetate (2×, 150 ml). The extracts were combined, washed with water, brine, dried over anhydrous magnesium sulfate and the solvent removed in vacuo to yield an oil. The oil was dissolved in ether and saturated ether-hydrogen chloride solution was added to precipitate a salt. Recrystallization (twice) from isopropanol-ether gave 3.3 g (41.7%) of product, mp 221°–223° C.

ANALYSIS: Calculated for $C_{20}H_{20}F_3N_3.HCl$: 60.68%C, 5.34%H, 10.62%N. Found: 60.86%C, 5.55%H, 10.62%N.

EXAMPLE 10

1-Hydroxymethyl-3-(1-methyl-4-piperidinyl)-1H-indazole

A solution of 0.52 g of paraformaldehyde, 3.0 g of 3-(1-methyl-4-piperidinyl)-1H-indazole, 15 ml of ethanol and 0.34 ml of 5% aqueous sodium hydroxide was refluxed for 3 hrs. The ethanol was removed in vacuo and the residue diluted with water. The aqueous suspension was extracted with dichloromethane (2×, 50 ml) and the combined extracts were washed with water and dried over anhydrous magnesium sulfate. The dichloromethane was evaporated in vacuo to yield an oil, which crystallized upon standing. The solid was recrystallized twice from ethyl acetate to yield 1.3 g (57.8%) of product, mp 128°–130° C.

ANALYSIS: Calculated for $C_{14}H_{19}N_2O$: 68.54%C, 7.81%H, 17.13%N. Found: 68.41%C, 7.81%H, 17.42%N.

EXAMPLE 11

1-(6-Fluoro-1,2-benzisoxazole-3-propyl)-3-(1-methyl-4-piperidinyl)-1H-indazole maleate To a stirred suspension under nitrogen of 0.8 g of sodium hydride (50% oil dispersion) in 45 ml of dimethylformamide, was added dropwise, 3.0 g of 3-(1-methyl-4-piperidinyl)-1H-indazole dissolved in 10 ml of hot dimethylformamide. The reaction mixture was stirred at ambient temperature for 45 min and then 3.9 g of 3-(3-chloroprop-1-yl)-6-fluoro-1,2-benzisoxalzole was added. The reaction mixture was stirred at ambient temperature overnight (ca. 16 hr) and then poured into water. The aqueous suspension was extracted with ether and the ether extract was washed with water, dried over anhydrous magnesium sulfate, and filtered. Treatment of the ethereal solution with 2.0 g of maleic acid suspended in 10 ml of ethanol resulted in an oil. Decantation of the supernatant ether solution and subsequent trituration of the oil with ethyl acetate gave a solid. Recrystallization of the solid from ethyl acetate yielded 3.0 g (43%) of product, mp 127°–129° C.

ANALYSIS: Calculated for $C_{23}H_{25}FN_4O.C_4H_4O_4$: 63.77%C, 5.75%H, 11.02%N. Found: 63.53%C, 5.71%H, 11.15%N.

EXAMPLE 12

1-Cyclopropylmethyl-3-(1-methyl-4-piperidinyl)-1H-indazole hydrobromide

To a stirred mixture of 1.19 g of sodium hydride (50% oil dispersion) in 65 ml of dimethylformamide was added, dropwise, 4.0 g of 3-(1-methyl-4-piperidinyl)-1H-indazole in 20 ml of hot dimethylformamide. The mixture was stirred for 1 hr at ambient temperature and then 1.40 g of chloromethylcyclopropane in 10 ml of dimethylformamide was added dropwise. The reaction mixture was stirred for 2½ days at ambient temperature. The reaction mixture was quenched with water, extracted with ethyl acetate, washed with water, dried over anhydrous magnesium sulfate and the solvent was removed in vacuo to yield an oil. The oil was dissolved in ether and saturated hydrogen bromide/ether solution was added dropwise to precipitate a salt. The salt was recrystallized from toluene and ethyl acetate to yield 2.8 g (32%) of product, mp 177°–179° C.

ANALYSIS: Calculated for $C_{17}H_{23}N_3.HBr$: 58.29%C, 6.86%H, 12.00%N. Found: 58.20%C, 6.59%H, 11.82%N.

EXAMPLE 13

1-Phenylmethyl-3-(1-methyl-4-piperidinyl)-1H-indazole hydrobromide

To a stirred suspension of 0.86 g of sodium hydride (50% oil dispersion) in 50 ml of dimethylformamide under nitrogen, was added, dropwise, 3.0 g of 3-(1-methyl-4-piperidinyl)-1H-indazole dissolved in 15 ml of hot dimethylformamide. After stirring one hr. at ambient temperature, 2.6 g of benzyl bromide in 5 ml of dimethylformamide was added. The reaction mixture was stirred at ambient temperature for 15 hrs and then poured into water. The aqueous mixture was extracted with ethyl acetate. The ethyl acetate extract was washed with water, brine and dried over anhydrous magnesium sulfate. The ethyl acetate was evaporated in vacuo to yield an oil. The oil was dissolved in ether and gaseous hydrogen bromide was passed through the solution to yield an oily material. The oily material was triturated with boiling ethyl acetate. The solid was collected and recrystallized from absolute ethanol to yield 2.4 g (44.3%) of product, mp 218°–220° C.

ANALYSIS: Calculated for $C_{20}H_{23}N_3.HBr$: 62.18%C, 6.00%H, 10.88%N. Found: 62.13%C, 6.24%H, 10.87%N.

EXAMPLE 14

1-(2-Phenylethyl)-3-(1-methyl-4-piperidinyl)-1H-indazole hydrobromide

To a stirred mixture of 0.86 g of sodium hydride (50% oil dispersion) in 50 ml of dimethylformamide was added, dropwise, 3.0 g of 3-(1-methyl-4-piperidinyl)-1H-indazole in 15 ml of hot dimethylformamide. The reaction mixture was stirred at ambient temperature for 1 hr and then a solution of 3.33 g of (2-bromoethyl)benzene in 10 ml of dimethylformamide was added dropwise. The reaction mixture was stirred for 2½ days at ambient temperature, cooled to 0°, and water was added dropwise. The mixture was extracted with ethyl acetate, washed with water, dried over anhydrous magnesium sulfate and the solvent was removed in vacuo to yield an oil. The oil was dissolved in ether and a saturated hydrogen bromide/ether solution was added dropwise. The resultant solid was recrystallized two times from ethanol to yield 2.0 g (36%) of product, mp 163°–164° C.

ANALYSIS: Calculated for $C_{21}H_{25}N_3.HBr$: 63.00%C, 6.50%H, 10.50%N. Found: 62.93%C, 6.58%H, 10.55%N.

EXAMPLE 15

1-Acetyl-3-(1-methyl-4-piperidinyl)-1H-indazole hydrochloride

A mixture of 2.0 g of 3-(1-methyl-4-piperidinyl)-1H-indazole, 20 ml of acetic anhydride and a few drops of pyridine was stirred under reflux for 2 hrs. Most of the acetic anhydride was evaporated in vacuo and the resultant solution was poured into 80 ml of water. The solution was made basic with ammonium hydroxide solution. A white solid precipitated. The solid was collected, dried and dissolved in ether. Saturated ether-hydrogen chloride solution was added. The salt was reprecipitated from cold methanol with ether to yield 1.6 g (60.5%) of product, mp 238°–239° C.

ANALYSIS: Calculated for $C_{15}H_{19}N_3O.HCl$: 61.32%C, 6.86%H, 14.30%N. Found: 61.08%C, 6.76%H, 14.32%N.

EXAMPLE 16

1-Benzoyl-3-(1-methyl-4-piperidinyl)-1H-indazole hydrochloride

A mixture of 3.0 g of 3-(1-methyl-4-piperidinyl)-1H-indazole and 3.2 ml of benzoyl chloride was heated at 100° for 2 hrs. The resultant solid was triturated with ether and collected. The salt was twice recrystallized from ethanol-ether to yield 3.1 g (62.2%) of product, mp 234°–236° C.

ANALYSIS: Calculated for $C_{20}H_{21}N_3O.HCl$: 67.50%C, 6.23%H, 11.81%N. Found: 67.22%C, 6.15%H, 11.82%N.

EXAMPLE 17

3-(1-Methyl-4-piperidinyl)-1-trichloroethoxycarbonyl-1H-indazole hydrochloride

A mixture of 2.3 g of trichloroethyl chloroformate, 3.0 g of potassium carbonate, 2.1 g of 3-(1-methyl-4-piperidinyl)-1H-indazole and chloroform was heated under reflux for 16 hrs. The reaction mixture was cooled, filtered, and the filtrate was concentrated to a solid in vacuo. The solid was triturated with ethyl acetate, collected, and recrystallized from ethanol to yield 3.9 g (91%) of product, mp 190°–192° C.

ANALYSIS: Calculated for $C_{16}H_{18}Cl_3N_3O_2.HCl$: 44.99%C, 4.48%H, 9.85%N. Found: 44.64%C, 4.46%H, 9.84%N.

EXAMPLE 18

1-Phenylsulfonyl-3-(1-methyl-4-piperidinyl)-1H-indazole hydrochloride

A mixture of 2.5 g of 3-(1-methyl-4-piperidinyl)-1H-indazole and 50 ml of benzenesulfonyl chloride was heated on a steam bath for 1 hr. The solution was cooled to ambient temperature and then poured into ether. The precipitate was collected and triturated with ethyl acetate to yield a solid. The solid was combined with 1.5 g of solid from another experiment and recrystallized twice from isopropanol to yield 2.3 g (36%) of product, mp 222°–224° C.

ANALYSIS: Calculated for $C_{19}H_{21}N_3O_2S$: 58.24%C, 5.66%H, 10.72%N. Found: 58.17%C, 5.77%H, 10.80%N.

EXAMPLE 19

1-(4-Fluorobenzoyl)-3-(1-methyl-4-piperidinyl)-1H-indazole

A solution of 3.0 g of 3-(1-methyl-4-piperidinyl)-1H-indazole in 15 ml of 4-fluorobenzoyl chloride was heated at 100° for 2 hrs. The reaction mixture was poured into ether and the precipitate was collected. The precipitate was treated with dilute aqueous sodium hydroxide solution and extracted with chloroform. The chloroform extract was dried over anhydrous magnesium sulfate and the solvent removed in vacuo to yield 2.5 g (53%) of product, mp 132°–133° C.

ANALYSIS: Calculated for $C_{20}H_{20}FN_3O$: 71.20%C, 5.98%H, 12.45%N. Found: 71.42%C, 6.21%H, 12.50%N.

EXAMPLE 20

1-Ethoxycarbonyl-3-(1-methyl-4-piperidinyl)-1H-indazole hydrochloride

To a stirred mixture of the 3.5 g of 3-(1-methyl-4-piperidinyl)-1H-indazole, 2.7 g of potassium carbonate and 40 ml of chloroform was added, dropwise, 21.1 g of ethyl chloroformate. The reaction mixture was stirred under reflux for 16 hr, cooled, filtered, and the filtrate was concentrated in vacuo. The residue was triturated with ether. Recrystallization from ethanol-ether and then from isopropyl alcohol-ether gave 2.3 g (43.8%) of product, mp 181°–183° C. (gas evolution).

ANALYSIS: Calculated for $C_{16}H_{21}N_3O_2.HCl$: 59.34%C, 6.85%H, 12.98%N. Found: 58.76%C, 7.05%H, 12.80%N.

EXAMPLE 21

1-(4-Methoxybenzoyl)-3-(1-methyl-4-piperidinyl)-1H-indazole hydrochloride

A solution of 3.0 g of 3-(1-methyl-4-piperidinyl)-1H-indazole in 10 ml of p-anisoyl chloride was heated at 100° C. for 3 hr. The reaction mixture was cooled to ambient temperature, ether was added and the solid was collected. The solid, suspended in ether, was stirred for 16 hr. The mixture was filtered, and dried. Recrystallization from ethanol (twice) yielded 4.0 g (74.4%) of product, mp 235°–237° C.

ANALYSIS: Calculated for $C_{21}H_{23}N_3O_2.HCl$: 65.36%C, 6.27%H, 10.89%N. Found: 64.83%C, 6.16%H, 10.82%N.

EXAMPLE 22

1-(2-Chlorophenyl)-3-(1-methyl-4-piperidinyl)-1H-indazole fumarate

To a stirred suspension of 1.1 g of sodium hydride (50% oil dispersion) in 40 ml of dimethylformamide under nitrogen was added, dropwise, 4.0 g of 3-(1-methyl-4-piperidinyl)-1H-indazole in 25 ml of hot dimethylformamide. The reaction was stirred at ambient temperature for 1 hr and then 3.6 g of 1-chloro-2-fluorobenzene was added. The temperature was then raised to 120° and held at 120° for 20 hrs. The reaction was poured into water and the aqueous suspension was extracted with ether. The ether extract was washed with water, dried over anhydrous magnesium sulfate, and the ether was removed in vacuo. The residue was chromatographed on a Water's preparative high-pressure liquid chromatograph using a silica gel columns eluted with tetrahydrofuran-$(C_2H_5)_2NH$ (99:1). Evaporation of the appropriate fractions yielded an oil. The oil was dissolved in ether and 1.5 g of fumaric acid was added. The mixture was stirred at ambient temperature for 16 hr., and the solid was collected. Recrystallization from isopropyl alcohol-ether and then from ethanol-ether gave 2.5 g (31.4%) of product, mp 179°–181° C.

ANALYSIS: Calculated for $C_{19}H_{20}ClN_3.C_4H_4O_4$: 62.51%C, 5.47%H, 9.51%N. Found: 62.46%C, 5.50%H, 9.43%N.

EXAMPLE 23

4-(1-Benzoyl-1H-indazol-3-yl)piperidine-1-carbonitrile

A sample of 8.4 g of 1-benzoyl-3-(1-methyl-4-piperidinyl)-1H-indazole hydrochloride was converted to its free base and the base was dissolved in 135 ml of chloroform. The solution was stirred and 4.0 g of potassium carbonate was added followed by 2.7 g of cyanogen bromide. The reaction mixture was stirred under reflux for 16 hrs. The mixture was filtered, and the solvent was removed in vacuo. The mixture was chromatographed on a high-pressure column chromatography apparatus (silica gel), eluting with 0.3% methanol/dichloromethane. Evaporation of the appropriate fraction followed by recrystallization from toluene hexane yielded 2.2 g (28%) of the product, mp 144°–146° C.

ANALYSIS: Calculated for $C_{20}H_{18}N_4O$: 72.71%C, 5.59%H, 16.97%N. Found: 72.56%C, 5.57%H, 17.18%N.

EXAMPLE 24

6-Fluoro-3(4-piperidinyl)-1H-indazole

A solution of 20.0 g of 1-acetyl-4-(2,4-difluorobenzoyl)piperidine, 60 ml of hydrazine hydrate and 150 ml of n-butanol was refluxed for 48 hrs. The reaction was poured into 1 l of water, and the mixture was extracted with ethyl acetate. The ethyl acetate extract was washed with water, dried over anhydrous magnesium sulfate and the solvent was evaporated in vacuo. Recrystallization of the residue from isopropanol-water and then from isopropanol yielded 3.3 g (20.1%) of product, mp 214°–216° C.

ANALYSIS: Calculated for $C_{12}H_{14}N_3F$: 65.73%C, 6.44%H, 19.17%N. Found: 65.55%C, 6.35%H, 19.30%N.

EXAMPLE 25

1-(2-Furoyl)-3-(1-methyl-4-piperidinyl)-1H-indazole hydrochloride

A mixture of 4.0 g of 3-(1-methyl-4-piperidinyl)-1H-indazole, 2.7 ml of 2-furoyl chloride (95% pure) and 60 ml of chloroform was refluxed for 3 hrs. The mixture was filtered. The filtrate was evaporated under reduced pressure, the residue was triturated with ethyl acetate and the solid was collected. The solid and filtrate were combined and recrystallized twice from ethanol to yield 3.3 g (51.5%) of product, mp 268°–270° C.

ANALYSIS: Calculated for $C_{18}H_{19}N_3O_2 \cdot HCl$: 62.51%C, 5.83%H, 12.15%N. Found: 62.78%C, 6.00%H, 12.11%N.

EXAMPLE 26

1-(4-Chlorophenyl)-3-(1-methyl-4-piperidinyl)-1H-indazole fumarate

To a stirred suspension of 1.1 g of sodium hydride (50% oil dispersion) in 40 ml of dimethylformamide was added, dropwise, under nitrogen, 4.0 g of 3-(1-methyl-4-piperidinyl)-1H-indazole dissolved in 25 ml of hot dimethylformamide. The reaction was stirred at ambient temperature for 45 min, and 2.9 ml of 4-fluorochlorobenzene was added. The temperature was increased to 120° and the reaction proceeded at this temperature for 24 hr. The reaction was poured into water and the aqueous mixture was extracted with ethyl acetate. The ethyl acetate extract was washed with water, dried over anhydrous magnesium sulfate and evaporated in vacuo. The residue was heated (steam bath) with 3N hydrochloric acid and the salt was collected. The salt was immediately recrystallized from water. The wet salt was treated with ammonium hydroxide and the base was extracted into dichloromethane. Evaporation of the dichloromethane in vacuo gave an oil. The oil solidified on standing. The solid was dissolved in ether and 1.4 g of fumaric acid was added. Recrystallization from 2-propanol gave 3.9 g (47.5%) of product, mp 176°–178° C.

ANALYSIS: Calculated for $C_{19}H_{20}ClN_3 \cdot C_4H_4O_4$: 62.25%C, 5.47%H, 9.51%N. Found: 62.32%C, 5.40%H, 9.56%N.

EXAMPLE 27

6-Fluoro-3-[1-(1-propyl)-4-piperidinyl]-1H-indazole

A mixture of 3.0 g of 6-fluoro-3-(4-piperidinyl)-1H-indazole, 1.8 g of 1-bromopropane, 2.5 g of sodium bicarbonate and 30 ml of dimethylformamide was stirred and heated at 60° for 2 hr. After stirring at ambient temperature for 14 hr, the reaction was poured into water and the aqueous suspension was extracted with ethyl acetate. The ethyl acetate was washed with water, dried over anhydrous magnesium sulfate and the solvent was removed in vacuo. Recrystallization of the residue from ethyl acetate yielded 2.3 g (63%) of product. This material was combined with a sample from another experiment and recrystallized from ethyl acetate to yield the analytical sample, mp 175°–177° C.

ANALYSIS: Calculated for $C_{15}H_{20}FN_3$: 68.94%C, 7.71%H, 16.08%N. Found: 69.24%C, 7.62%H, 16.15%N.

EXAMPLE 28

6-Fluoro-3-[1-(2-phenylethyl)-4-piperidinyl]-1H-indazole

A mixture of 5.0 g of 6-fluoro-3-(4-piperidinyl)-1H-indazole, 4.6 g of (2-bromoethyl)benzene, 4.2 g of sodium bicarbonate and 50 ml of dimethylformamide was stirred at 60° for 3 hr and at ambient temperature for 14 hr. The reaction was poured into water and the aqueous mixture extracted with ethyl acetate. The ethyl acetate was washed with water, dried over anhydrous magnesium sulfate and the solvent was removed in vacuo. The residue was recrystallized twice from 2-propanol (one charcoal treatment) to yield 2.6 g (35%) of product, mp 163°–165° C.

ANALYSIS: Calculated for $C_{22}H_{22}FN_3$: 74.27%C, 6.86%H, 12.99%N. Found: 74.45%C, 6.96%H, 13.49%N.

EXAMPLE 29

1-Benzoyl-3-[1-(2-phenylethyl)-4-piperidinyl]-1H-indazole hydrochloride

A mixture of 1.6 g of 3-(1-pheneth-2-yl-4-piperidinyl)-1H-indazole and 7 ml of benzoyl chloride was heated at 100° for 2 hr. After cooling, ether was added and the solid was collected. The solid was combined with material from a prior experiment and recrystallized from methanol to yield 2.4 g (51%) of product, mp 248°–250° C.

ANALYSIS: Calculated for $C_{27}H_{26}FN_3O \cdot HCl$: 69.89%C, 5.86%H, 9.06%N. Found: 70.03%C, 5.96%H, 9.22%N.

EXAMPLE 30

1-(3-Chlorobenzoyl)-3-(1-methyl-4-piperidinyl)-1H-indazole hydrochloride

A mixture of 3.0 g of 3-(1-methyl-4-piperidinyl)-1H-indazole and 8 ml of 3-chlorobenzoyl chloride was heated at 100° C. for 2 hours. The reaction was allowed to cool, and ether was added. The resultant solid was collected and recrystallized twice from isopropyl alcohol to yield 3.7 g (67.7%) of product, mp 209°–211° C.

ANALYSIS: Calculated for $C_{20}H_{20}ClN_3O \cdot HCl$: 61.54%C, 5.42%H, 10.77%N. Found: 61.54%C, 5.57%H, 10.66%N.

EXAMPLE 31

1-(2-Chlorobenzoyl)-3-(1-methyl-4-piperidinyl)-1H-indazole fumarate

A mixture of 3.0 g of 3-(4-piperidinyl)-1H-indazole and 8 ml of 2-chlorobenzoyl chloride was heated at 100° (steam bath) for 2 hr. The reaction was cooled to ambient temperature, and ether was added. The oil, which separated, solidifed upon scratching. The solid was treated with ammonium hydroxide and the precipitate was dissolved in ether-ethanol (350:10 ml). Fumaric acid (1.4 g) was added, and the mixture was stirred at ambient temperature for 4 hr. The resultant solid was collected, dried, triturated with hot acetone, and recrystallized from isopropyl alcohol to yield 3.6 g (54.7%) of the product, mp 182°–184° C.

ANALYSIS: Calculated for $C_{20}H_{20}ClN_3O \cdot C_4H_4O_4$: 61.34%C, 5.15%H, 8.94%N. Found: 61.54%C, 5.30%H, 8.96%N.

EXAMPLE 32

6-Fluoro-3-(1-methyl-4-piperidinyl)-1H-indazole

To a stirred suspension, under nitrogen, of 4.7 g of lithium aluminum hydride (50–55% oil dispersion) in 90 ml of tetrahydrofuran was added, dropwise, 8.9 g of 6-fluoro-3-(1-methoxycarbonyl-4-piperidinyl)-1H-indazole, dissolved in 50 ml of tetrahydrofuran. After the addition was complete, the reaction was heated under reflux for 2 hr. The reaction was cooled in an ice-salt bath and water was carefully added. The mixture was filtered and the filter cake was washed with tetrahydrofuran and twice with not methanol. The filtrate was concentrated in vacuo. The residue was triturated with ethyl acetate to yield 5.1 g (68%) of product, mp 217°–220°. Recrystallization from ethanol (twice) provided the analytical sample, mp 218°–220° C.

ANALYSIS: Calculated for $C_{13}H_{16}FN_3$: 66.93%C, 6.91%H, 18.01%N. Found: 67.00%, 6.97%H, 18.09%N.

EXAMPLE 33

1-(2-Nitrophenyl)-3-(1-methyl-4-piperidinyl)-1H-indazole fumarate

To a stirred suspension, under nitrogen, of 0.86 g of a 50% oil dispersion of sodium hydride in 20 ml of dimethylformamide was added, dropwise, 3.2 g of 3-(1-methyl-4-piperidinyl)-1H-indazole dissolved in 25 ml of hot dimethylforamide. Upon completion of the addition, the reaction mixture was stirred at ambient temperature for one hr and a solution of 2.2 g of 1-fluoro-2-nitrobenzene in 5 ml of dimethylformamide was added slowly. The reaction mixture was stirred at ambient temperature for 2 hrs and then poured into water. The precipitate was collected and then dissolved in ethanol-ether. To the stirred solution, 1.7 g of fumaric acid was added. After stirring at ambient temperature for four hrs, the mixture was filtered and the filter cake was recrystallized from methanol-ether (twice) to yield 4.3 g (67.8%) of product, mp 210°–212° C.

ANALYSIS Calculated for $C_{19}H_{20}N_4O_2 \cdot C_4H_4O_4$: 61.05%C, 5.35%H, 12.38%N. Found: 61.08%C, 5.43%H, 12.47%N.

EXAMPLE 34

1-(2-Chlorophenyl)-3-(4-piperidinyl)-1H-indazole fumarate

To a stirred mixture of 4.2 g of cyanogen bromide, 6.3 g of potassium carbonate and 125 ml of dimethylsulfoxide was added, dropwise, 12.0 g of 1-(2-chlorophenyl)-3-(1-methyl-4-piperidinyl)-1H-indazole dissolved in 30 ml of dimethylsulfoxide. The reaction mixture was stirred at ambient temperature for two hrs and then poured into water. The aqueous mixture was extracted with ethyl acetate. The ethyl acetate extracts were washed with water, dried over anhydrous magnesium sulfate, and the solvent was removed in vacuo to give an oil. The oil was triturated with ether to give 7.1 g (57%) of 4-[2-(2-chlorophenyl)-1H-indazol-3-yl]piperidine-1-carbonitrile, mp 109°–111° C.

A stirred mixture of 6.5 of 4-[2-(2-chlorophenyl)-1H-indazol-3-yl]piperidine-1-carbonitrile and 60 ml of 25% aqueous sulfuric acid was heated under reflux for 16 hr. The reaction mixture was cooled in an ice-bath and 50% aqueous sodium hydroxide solution was added dropwise until the mixture was basic. The aqueous mixture was extracted with ethyl acetate. The extracts were washed with water, dried over anhydrous magnesium sulfate and the solvent removed in vacuo to give an oil. The oil was dissolved in ethanol-ether and 2.2 g of fumaric acid was added. After stirring at ambient temperature for 6 hrs, the salt was collected. The salt was recrystallized twice from methanol-ether to yield 2.4 g (30%) of product, mp 213°–215° C.

ANALYSIS: Calculated for $C_{18}H_{18}ClN_3 \cdot C_4H_4O_4$: 61.75%C, 5.18%H, 9.82%N. Found: 61.55%C, 5.48%H, 9.62%N.

EXAMPLE 35

1-(2-Aminophenyl)-3-(1-methyl-4-piperidinyl)-1H-indazole fumarate

To a cooled (5° C.), stirred solution of 9.5 g of stannous chloride dihydrate in 20 ml of concentrated hydrochloric acid and 10 ml of tetrahydrofuran was added, dropwise, 3.6 g of 1-(2-nitro-phenyl)-3-(1-methyl-4-piperidinyl)-1H-indazole dissolved in 25 ml of tetrahydrofuran. After completion of the addition, the cooling bath was removed and the reaction mixture was stirred at ambient temperature for 3 hrs. The reaction mixture was poured into ice water and made basic with 10% sodium hydroxide solution. The mixture was extracted with ethyl acetate. The extract was washed with water, dried over anhydrous magnesium sulfate and the solvent was removed in vacuo. The residue was dissolved in ethanol (warming) and 2.0 g of fumaric acid was added. The mixture was then warmed on the steam bath for a few mins. The salt was collected to give 3.4 g (80%) of product. The salt was combined with 1.1 g of another experiment and recrystallized first from dimethylformamide-ethyl acetate (twice) and then from methanol-ether to yield the analytical sample, mp 208°–210° C.

ANALYSIS: Calculated for $C_{19}H_{22}N_4 \cdot C_4H_4O_4$: 65.40%C, 6.21%H, 13.24%N. Found: 65.46%C, 6.40%H, 13.35%N.

EXAMPLE 36

1-(2-Fluorophenyl)-3-(1-methyl-4-piperidinyl)-1H-indazole hydrochloride

To a stirred suspension of 1.0 g of a 50% oil dispersion of sodium hydride in 20 ml of dimethylformamide, under nitrogen, was added, dropwise, 3.2 g of 3-(1-methyl-4-piperidinyl)-1H-indazole dissolved in 25 ml of hot dimethylformamide. After ageing at ambient temperature for 45 mins, 3.6 g of 1,2-difluorobenzene was added and the temperature was raised to 120° C. and held there for 6 hrs. The reaction mixture was quenched with water and the aqueous mixture extracted with ether. The ether extract was washed with water, dried over anhydrous magnesium sulfate and the solvent removed in vacuo to yield an oil. The oil was combined with 2.7 g of oil from another experiment and the combined sample (6.9 g) was chromatographed. Flash chromatographed was utilized with 210 g of silica gel and ethyl acetate-diethylamine (10%) as the eluent. Evaporation of the appropriate fractions gave 4.3 g (57%) of product, as an oil. Treatment of the oil with ethereal hydrogen chloride gave the hydrochloride salt. The salt was recrystallized from ethanol-ether and then from acetonitrile to yield the analytical sample, mp 215°–217° C.

ANALYSIS: Calculated for $C_{19}H_{20}FN_3 \cdot HCl$: 65.98%C, 6.11%H, 12.16%N. Found: 65.79%C, 6.16%H, 12.21%N.

EXAMPLE 37

1-(3-Fluorophenyl)-3-(1-methyl-4-piperidinyl)-1H-indazole hydrochloride

To a suspension of 2.0 g of a 50% oil dispersion of sodium hydride in 40 ml of dimethylformamide was added, dropwise, 6.4 g of 3-(1-methyl-4-piperidinyl)-1-H-indazole in 50 ml of hot dimethylformamide. After stirring for 40 mins at ambient temperature, 7.2 g of 1,3-difluorobenzene was added. The mixture was heated at 120° C. for 20 hrs, cooled and poured into water. The mixture was extracted with ether. The extracts were dried over anhydrous magnesium sulfate and concentrated to yield an oil. The oil was purified using flash chromatograhy (silica gel, diethylamine-ethyl acetate, 1:9). Evaporation of appropriate fractions gave an oil. The oil was dissolved in anhydrous ether and hydrogen chloride gas was bubbled into the solution. The ether was decanted and the solid was recrystallized twice from ethanol-ether to yield 2.6 g (25%) of product, mp 254°–256° C.

ANALYSIS: Calculated for $C_{19}H_{20}FN_3 \cdot HCl$: 65.99%C, 6.12%H, 12.15%N. Found: 65.83%C, 6.09%H, 12.15%N.

EXAMPLE 38

6-Fluoro-1-(2-fluorophenyl)-3-(1-methyl-4-piperidinyl)-1H-indazole fumarate

To a stirred suspension, under nitrogen, of 1.2 g of a 50% oil dispersion of sodium hydride in 25 ml of dimethylformamide was added, dropwise, 4.2 g of 6-fluoro-3-(1-methyl-4-piperidinyl)-1H-indazole dissolved in 30 ml of hot dimethylformamide. The reaction mixture was stirred at ambient temperature for 45 mins and then 4.4 g of 1,2-difluorobenzene was added. The temperature was raised to 120° C. and held there for 6 hrs. The reaction mixture was poured into water and the aqueous mixture was extracted with ethyl acetate. The extract was washed with water, dried over anhydrous magnesium sulfate and the solvent concentrated to yield an oil. The oil was triturated with hexane to yield 1.3 g of the indazole starting material. The filtrate was concentrated to an oil. The oil was purified by flash chromatography utilizing a silica gel column (50×145 mm) and ethyl acetate-diethylamine (10%) as the eluent. Concentration of the appropriate fractions gave 2.0 g (33%) of product, as an oil. The oil was dissolved in ether, stirred, and 0.8 g of fumaric acid was added. The salt was collected, dried and had mp 181°–183° C.

ANALYSIS: Calculated for $C_{19}H_{19}F_2N_3 \cdot C_4H_4O_4$: 62.29%C, 5.23%H, 9.48%N. Found: 62.15%C, 5.40%H, 9.47%N.

EXAMPLE 39

1-Acetyl-4-(6-fluoro-1-phenyl-1H-indazol-3-yl)piperidine

To a stirred solution of 3.0 g of 1-acetyl-4-(2,4-difluorobenzoyl)piperidine phenylhydrazone in 30 ml of dimethylformamide, under nitrogen, was added 0.44 g of a 50% oil dispersion of sodium hydride. The reaction mixture was heated, and at about 40° C. a vigorous evolution of hydrogen occurred. The temperature was then raised to 80° C. and held there for 1.5 hrs. The reaction mixture was poured into water and the aqueous suspension was extracted with ethyl acetate. The ethyl acetate extracts were washed with water, dried over anhydrous magnesium sulfate and concentrated to yield an oil. The oil was combined with the oil from another experiment and a total of 13.5 g of material was chromatographed on a Water's Prep LC 500. Two silica gel columns were utilized and dichloromethane-methanol (3%) was used as the eluent. The appropriate fractions were evaporated. The residue was recrystallized twice from isopropyl alcohol-water (one charcoal treatment) to yield 2.4 g (18%) of product, mp 126°–128° C.

ANALYSIS: Calculated for $C_{20}H_{20}FN_3O$: 71.20%C, 5.98TH, 12.45%N. Found: 70.98%C, 5.99%H, 12.48%N.

EXAMPLE 40

1-[2-(Trifluoromethyl)phenyl]-3-(1-methyl-4-piperidinyl)-1H-indazole

To a stirred suspension of 1.0 g of a 50% oil dispersion of sodium hydride in 20 ml of dimethylformamide was added, dropwise, 3.2 g of 3-(1-methyl-4-piperidinyl)-1H-indazole dissolved in 25 ml of hot dimethylformamide. After stirring for one hr at ambient temperature, 3.75 ml of 2-fluorobenzotrifluoride was added. The reaction mixture was heated to 90° C. and stirred for 17 hrs. The mixture was then poured inter water, extracted with ether, dried over anhydrous magnesium sulfate and concentrated. The residue was purified using flash chromatography (silica gel, diethylamine-ethyl acetate, 1:9). The appropriate fractions were evaporated. The residue was recrystallized once from hexane, then combined with a previously prepared sample (1.1 g), and recrystallized from hexane to yield 2.17 g (24%) of product, mp 110°–111° C.

ANALYSIS: Calculated for $C_{20}H_{20}F_3N_3$: 66.84%C, 5.61%H, 11.69%N. Found: 66.65%C, 5.59%H, 11.82%N.

EXAMPLE 41

1-(2-Fluorophenylmethyl)-3-(1-methyl-4-piperidinyl)-1H-indazole hydrobromide To a suspension of 0.86 g of a 50% oil dispersion of sodium hydride in 50 ml of dimethylformamide was added, dropwise, 3.0 g of 3-(1-methyl-4-piperidinyl)-1N-indazole dissolved in 15 ml of hot dimethylformamide. After stirring for 1 hr, 2.19 g of 2-fluorobenzyl chloride was added. The reaction mixture was stirred at ambient temperature for 17 hrs and then poured into 250 ml of water. The mixture was extracted with ether. The extract was washed with water, brine and dried over anhydrous magnesium sulfate. The solvent was evaporated. The residue was dissolved in anhydrous ether and hydrogen bromide gas was bubbled through the solution. The salt was triturated with ether and recrystallized from ethanol-ether and then ethanol to yield 3.06 g (54%) of product, mp 205°–206° C.

ANALYSIS: Calculated for $C_{20}H_{22}FN_3 \cdot HBr$: 59.41%C, 5.73%H, 10.39%N. Found: 59.02%C, 5.68%H, 10.29%N.

EXAMPLE 42

1-Benzoyl-6-chloro-3-(1-methyl-4-piperidinyl)-1H-indazole hydrochloride

A mixture of 3.0 g of 6-chloro-3-(1-methyl-4-piperidinyl)-1H-indazole and 8 ml of benzoyl chloride was heated at 100° C. on a steam bath for 4 hrs. The reaction mixture was cooled to ambient temperature and ether was added. The precipitate was filtered, washed with ether and dried. Recrystallization from ethanol (twice) yielded 2.6 g (56%) of product, mp 248°–250° C.

ANALYSIS: Calculated for $C_{20}H_{20}ClN_3O.HCl$: 61.54%C, 5.42%H, 10.77%N. Found: 61.34%C, 5.46%H, 10.67%N.

EXAMPLE 43

1-(4-Chlorobenzoyl)-3-(1-ethyl-4-piperidinyl)-6-fluoro-1H-indazole hydrochloride A mixture of 3.0 g of 3-(1-ethyl-4-piperdinyl)-6-fluoro-1H-indazole and 8 ml of 4-chlorobenzoyl chloride was heated at 100° C. in a steam bath for 4 hrs. Ether was added and the solid was collected. The solid was recrystallized twice from ethanol-ether to yield 2.9 g (57%) of product, mp 240°–242° C.

ANALYSIS: Calculated for $C_{21}H_{21}ClFN_3O.HCl$: 59.72%C, 5.01%H, 9.95%N. Found: 59.69%C, 5.39%H, 9.92%N.

EXAMPLE 44

1-(4-Chlorobenzoyl)-6-fluoro-3-(1-methyl-4-piperidinyl)-1H-indazole hydrochloride A mixture of 2.0 g of 6-fluoro-3-(1-methyl-4-piperidinyl)-1H-indazole and 5 ml of 4-chlorobenzoyl chloride was heated at 100° C. in a steam bath for 2 hours. After cooling, ether was added and the solid was collected. The solid was combined with a 2.5 g sample from another experiment and recrystallized twice from ethanol-ether to yield 4.7 g (56%, calculated on the combination of both experiments) of product, mp 258°–260° C.

ANALYSIS: Calculated for $C_{20}H_{19}ClN_3.HCl$: 58.83%C, 4.69%H, 10.29%N. Found: 59.02%C, 5.07%H, 10.30%N.

EXAMPLE 45

1-(4-Methylbenzoyl)-3-(1-methyl-4-piperidinyl)-1H-indazole fumarate

A mixture of 3.0 g of 3-(1-methyl-4-piperidinyl)-1H-indazole and 8 ml of 4-toluoyl chloride was heated at 100° C. on a steam bath for 4 hrs. Ether was added to the cooled mixture and the salt was collected. The salt was converted to its free base by means of ammonium hydroxide solution. The base was dissolved in ethanol (90 ml)-ether (175 ml) and 1.5 g of fumaric acid was added. The mixture was stirred at ambient temperature for 16 hrs, and the resultant fumarate salt was collected. Recrystallization twice from methanol-ether yielded 3.8 g (60%) of product, mp 205°–207° C.

ANALYSIS: Calculated for $C_{21}H_{23}N_3O.C_4H_4O_4$: 66.80%C, 6.06%H, 9.35%N. Found: 66.98%C, 6.14%H, 9.44%N.

EXAMPLE 46

1-(3,4-Dichlorobenzoyl)-3-(1-methyl-4-piperidinyl)-1H-indazole

A mixture of 3.0 g of 3-(1-methyl-4-piperidinyl)-1H-indazole and 8 ml of 3,4-dichlorobenzoyl chloride was heated at 100° C. in a steam bath for 4 hrs. After the reaction mixture cooled to ambient temperature, ether was added and the salt was collected. The salt was mixed with water and ammonium hydroxide solution was added until the mixture was basic. The mixture was warmed on the steam bath for about 5 mins, cooled and extracted with dichloromethane. Evaporation of the dichloromethane in vacuo provided the free base. The base was recrystallized from methanol-trichloromethane (with concentration of the mother liquor) to yield 3.0 g (57%) of product, mp 187°–189° C.

ANALYSIS: Calculated for $C_{20}H_{19}Cl_2N_3O$: 61.86%C, 4.93%H, 10.82%N. Found: 61.83%C, 5.02%H, 10.84%N.

EXAMPLE 47

1-Benzoyl-6-fluoro-3-(1-methyl-4-piperidinyl)-1H-indazole fumarate

A mixture of 3.1 g of 6-fluoro-3-(1-methyl-4-piperidinyl)-1H-indazole and 8 ml of benzoyl chloride was heated at 100° C. in a steam bath for 8 hrs. After cooling, ether was added and the solid was collected. The solid was treated with ammonium hydroxide solution to give an oil. The oil was dissolved in 300 ml of ether, stirred and 1.2 g of fumaric acid was added. After four hrs at ambient temperature, the fumarate salt was collected. Recrystallization from ethanol-ether yielded 3.0 g (50.9%) of product, mp 180°–182° C.

ANALYSIS: Calculated for $C_{20}H_{20}FN_3O.C_4H_4O_4$: 63.57%C, 5.33%H, 9.27%N. Found: 63.51%C, 5.43%H, 9.35%N.

EXAMPLE 48

1-[4-(Trifluoromethyl)benzoyl]-3-(1-methyl-4-piperidinyl)-1H-indazole fumarate

A mixture of 3.0 g of 3-(1-methyl-4-piperidinyl)-1H-indazole and 8 ml of 4-trifluoromethylbenzoyl chloride was heated at 100° C. on a steam bath. After 2 hrs, an additional 5 ml of 4-trifluoromethylbenzoyl chloride was added and heating was continued for two additional hrs. After cooling to ambient temperature, ether was added and the salt was collected. The salt was converted to its free base by means of ammonium hydroxide solution. The free base was dissolved in ethanol-ether and 0.75 g of fumaric acid was added to give 2.7 g (38%) of product. Two samples of the salt were combined and recrystallized from ethanol (twice) to yield the analytical sample, mp 212°–214° C.

ANALYSIS: Calculated for $C_{21}H_{20}F_3N_3O.C_4H_4O_4$ 59.64%C, 4.80%H, 8.35%N. Found: 59.57%C, 4.86%H, 8.41%N.

EXAMPLE 49

1-(4-Chlorobenzoyl)-3-(1-methyl-4-piperidinyl)-1H-indazole fumarate

A solution of 3.0 g of 3-(1-methyl-4-piperidinyl)-1H-indazole and 8 ml of 4-chlorobenzoyl chloride was heated at 100° C. in a steam bath for 4 hrs. After cooling to ambient temperature, ether was added and the salt was collected. The salt was converted into its free base by means of ammonium hydroxide soluton and extractive isolation with dichloromethane. The base was dissolved in 150 ml of hot ethanol and 1.6 g of fumaric acid was added. Ether (200 ml) was added to the solution and the fumarate salt was collected. Two recrystallizations from ethanol yielded 3.5 g (54%) of product, mp 216°–218° C.

ANALYSIS: Calculated for $C_{20}H_{20}ClN_3O.C_4H_4O_4$: 61.34%C, 5.15%H, 8.94%N. Found: 61.42%C, 5.18%H, 9.00%N.

EXAMPLE 50

6-Chloro-3-(1-methyl-4-piperidinyl)-1H-indazole

To a stirred solution, under nitrogen, of 13.0 g of 4-(6-chloro-1H-indazol-3-yl)piperidine-1-carboxylic acid methyl ester in 150 ml of tetrahydrofuran was added, dropwise, 48 ml of a 1M solution of lithium aluminum hydride (0.048 mole) in tetrahydrofuran. The solution was stirred under reflux for 1 hr. The reaction mixture was cooled in an ice-salt bath and water was added slowly. The reaction mixture was filtered, the filter cake washed with tetrahydrofuran and methanol, and the filtrate was concentrated. Recrystallization of the residue from ethanol-water yielded 7.6 g (69%) of product, mp 211°–213° C.

ANALYSIS: Calculated for $C_{13}H_{16}ClN_3$: 62.52%C, 6.46%H, 16.83%N. Found: 62.73%C, 6.61%H, 16.96%N.

EXAMPLE 51

3-(1-Ethyl-4-piperidinyl)-6-fluoro-1H-indazole

To a stirred suspension, under nitrogen, of 14.0 g of 3-(1-acetyl-4-piperidinyl)-6-fluoro-1H-indazole in 180 ml of tetrahydrofuran was added, dropwise, 55 ml of a 1M solution of lithium aluminum hydride in tetrahydrofuran. The reaction mixture was stirred under reflux for 1 hr and then stirred at ambient temperature for 15 hrs. The reaction mixture was cooled in an ice-salt bath and water was added slowly. The reaction mixture was filtered. The filter cake was washed with tetrahydrofuran and the filtrate was concentrated. Recrystallization of the residue from toluene afforded 9.0 g (68%) of product. Recrystallization of a 3.0 g sample from toluene yielded the analytical sample, mp 175°–178° C.

ANALYSIS: Calculated for $C_{14}H_{18}FN_3$: 67.99%C, 7.34%H, 16.99%N. Found: 68.07%C, 7.33%H, 17.11%N.

EXAMPLE 52

6-Chloro-3-(4-piperidinyl)-1H-indazole

A solution of 18.0 g of 1-acetyl-4-(4-chloro-2-fluorobenzoyl)piperidine, 130 ml of n-butanol and 51 ml of hydrazine monohydrate was stirred under reflux for 48 hrs. Most of the n-butanol was evaporated in vacuo and the residue was diluted with water. The aqueous mixture was extracted with ethyl acetate, and the extract was washed with water, dried over anhydrous magnesium sulfate and concentrated. The residue was recrystallized from acetonitrile to yield 3.0 g (20%) of product. This product was combined with a 1.3 g sample from another experiment and the combined samples (4.3 g) were recrystallized from acetonitrile to yield the analytical sample, mp 174°–176° C.

ANALYSIS Calculated for $C_{12}H_{14}ClN_3$: 61.14%C, 5.99%H, 17.88%N. Found: 61.02%C, 5.94%H, 17.94%N.

EXAMPLE 53

3-(4-piperidinyl)-1H-indazole

A solution of 4.7 g of 4-(1H-indazol-3-yl)piperidine-1-carboximidic acid methyl ester and 80% of acetic acid was heated under reflux for 48 hrs. The reaction mixture was cooled and poured into water. The aqueous phase was extracted with ether and then made basic by the slow addition of a 50% aqueous sodium hydroxide soluton. A solid separated from the solution. The solid was collected and dried. Recrystallization from ethanol yielded 1.7 g (46%) of product. Concentration of the mother liquors from this and another experiment gave additional product, mp 213°–215° C.

ANALYSIS: Calculated for $C_{12}H_{15}N_3$: 71.61%C, 7.51%H, 20.88%N. Found: 70.89%C, 7.48%H, 20.74%N.

EXAMPLE 54

6-Bromo-1-methyl-3-(4-piperidinyl)-1H-indazole hydrochloride

A solution of 3.3 g of 4-(4-bromo-2-fluorobenzoyl)-1-acetylpiperidine, 1.1 g (0.013 mole) of methylhydrazine and 30 ml of n-butanol was heated under reflux for 16 hrs. The reaction mixture was concentrated in vacuo and the residue was diluted with water. The aqueous suspension was made basic with ammonium hydroxide solution and extracted with dichloromethane. The extract was washed with water, dried over anhydrous potassium carbonate and the solvent was concentrated to give 3-(1-acetyl-4-piperidinyl)-6-bromo-1H-indazole, as an oil.

A solution of 3.0 g of 3-(1-acetyl-4-piperidinyl)-6-bromo-1H-indazole and 30 ml of 6N hydrochloric acid was heated under reflux for 4 hrs. The reaction mixture was cooled in an ice-bath, stirred and 50% aqueous sodium hydroxide solution was added dropwise until the reaction mixture was basic. The aqueous mixture was extracted with ether. The ether extracts were washed with water, dried over anhydrous magnesium sulfate and the solvent was concentrated to yield 1.6 g (62%) of product, as an oil. The products from three experiments were combined and converted to the hydrochloride salt with ethereal hydrogen chloride. The salt was recrystallized twice from ethanol-ether and then once from trichloromethane-ether to yield the analytical sample, mp 238°–240° C.

ANALYSIS: Calculated for $C_{13}H_{16}BrN_3 \cdot HCl$: 47.22%C, 5.18%H, 12.71%N. Found: 46.96%C, 5.12%H, 22.66%N.

EXAMPLE 55

3-(1-Acetyl-4-piperidinyl)-6-fluoro-1H-indazole

A solution ōf 15.0 g of 4-(2,4-difluorobenzoyl)-1-acetylpiperidine, 6.9 g of hydrazine hydrate and 140 ml of ethanol was heated under reflux for 4 hrs. The ethanol was removed in vacuo to give a solid. The solid was triturated with water, filtered and dried to yield 12.5 g (64%) of 1-acetyl-4-(2,4-difluorobenzoyl)piperidine hydrazone, mp 139°–142° C.

A mixture of 12.1 g of 1-acetyl-4-(2,4-difluorobenzoyl)piperidine hydrazone, 11.8 g of potassium carbonate and 120 ml of dimethylformamide was stirred and heated at 120° C. for 16 hrs. The reaction mixture was poured into water and the aqueous solution was extracted with ethyl acetate. The extract was washed with water, dried over anhydrous magnesium sulfate and the solvent concentrated to give a solid. Recrystallization of the solid from ethyl acetate (twice) yielded 4.1 g (42% with concentration of mother liquor) of product, mp 162°–164° C.

ANALYSIS: Calculated for $C_{14}H_{16}FN_3O$: 64.35%C, 6.17%H, 16.08%N. Found: 64.10%C, 6.31%H, 15.89%N.

EXAMPLE 56

3-(1-Acetyl-4-piperidinyl)-6-chloro-1H-indazole

A mixture of 19.6 g of 1-acetyl-4-(2-fluoro-4-chlorobenzoyl)piperidine hydrazone, 18.2 g of potassium carbonate and 200 ml of dimethylformamide was stirred, under nitrogen, at 120° C. for 16 hrs. After cooling to ambient temperature, the reaction mixture was poured into water and the aqueous mixture was extracted with ethyl acetate. The extract was washed with water, dried over anhydrous magnesium sulfate and concentrated to an oil. Upon standing, a solid formed. The solid was triturated with ethyl acetate to yield 3.8 g (21%) of product. Recrystallization from acetonitrile gave the analytical sample, mp 172°–174° C.

ANALYSIS: Calculated for $C_{14}H_{16}ClN_3O$: 60.54%C, 5.81%H, 15.13%N. Found: 60.55%C, 5.83%H, 15.33%N.

EXAMPLE 57

4-(6-Chloro-1H-indazol-3-yl)piperidine-1-carboxylic acid methyl ester

To a stirred suspension of 5.8 g of 6-chloro-3-(4-piperidinyl)-1H-indazole, 4.6 g of sodium bicarbonate and trichloromethane (25 ml)-tetrahydrofuran (25 ml) was added, dropwise, 5.2 g of methyl chloroformate. The reaction mixture was stirred at ambient temperature for 16 hrs and then poured into water. The organic layer was collected, washed with water, dried over anhydrous potassium carbonate and the solvent concentrated to give 4-(6-chloro-1-methyoxycarbonyl-1H-indazol-3-yl)piperidine-1-carboxylic acid methyl ester, as an oil. The oil was dissolved in 50 ml of methanol and 1.5 ml of a 25% sodium methoxide-methanol solution was added. The reaction mixture was stirred at ambient temperature for 0.5 hrs, poured into water and the aqueous mixture extracted with dichloromethane. The dichloromethane extract was washed with water, dried over anhydrous magnesium sulfate and the solvent evaporated to an oil. The oil was triturated with hexane. Recrystallization from toluene-hexane (twice) yielded 3.5 g (47%) of product, mp 132°–134° C.

ANALYSIS: Calculated for $C_{14}H_{16}ClN_3O_2$: 57.24%C, 5.49%H, 14.30%N. Found: 57.22%C, 5.46%H, 14.33%N.

EXAMPLE 58

1-(4-Pyridinyl)-3-(1-methyl-4-piperidinyl)-1H-indazole sesquifumarate

To a stirred suspension of 1.72 g of a 50% oil dispersion of sodium hydride, under nitrogen, in 30 ml of dimethylformamide was added, dropwise, 3.2 g of 3-(1-methyl-4-piperidinyl)-1H-indazole in 25 ml of hot dimethylformamide. After stirring at ambient temperature for 45 mins, 2.3 g of 4-chloropyridine hydrochloride was added portionwise. The reaction mixture was stirred at ambient temperature for 16 hrs and then heated under reflux for 12 hrs. The reaction mixture was cooled to ambient temperature and 0.43 g of a 50% oil dispersion of sodium hydride was added followed by 0.6 g of 4-chloropyridine. The reaction mixture was then heated under reflux for an additional 4 hrs, cooled to ambient temperature and poured into water. The aqueous mixture was extracted with ethyl acetate. The ethyl acetate extract was washed with water, dried over anhydrous magnesium sulfate and the solvent was removed in vacuo. The residue was purified in two runs by flash chromatography (silica gel, 150×50 mm), eluting with ethyl acetate-diethylamine (9:1). Similar fractions were combined and evaporated. The residue was converted to the fumarate salt by dissolution in ethanol (25ml)-ether (175 ml) and by adding 1.9 g of fumaric acid. Recrystallization from dimethylformamide yielded 3.2 g (46%) of product, mp 205°–207° C.

ANALYSIS: Calculated for $C_{18}H_{20}N_4 \cdot 1.5C_4H_4O_4$: 61.79%C, 5.62%H, 12.01%N. Found: 61.50%C, 5.78%H, 12.18%N.

EXAMPLE 59

1-(2-Pyridinyl)-3-(1-methyl-4-piperidinyl)-1H-indazole fumarate

To a stirred suspension, under nitrogen, of 0.86 g of a 50% oil dispersion of sodium hydride in 20 ml of dimethylformamide was added, dropwise, 3.2 g of 3-(1-methyl-4-piperidinyl)-1H-indazole dissolved in 25 ml of hot dimethylformamide. The reaction mixture was stirred at ambient temperature for 1 hr and then 1.5 g of 2-fluoropyridine was added. The temperature was raised to 95°–100° C. and held there for 6 hrs. The reaction mixture was allowed to cool and was then poured into water. A solid separated from the solution. The solid was collected and dried to yield 3.5 g (79.8%) of product, mp 123°–125° C., as the free base. The fumarate salt was prepared by dissolving the product in hot ethanol, adding 2.7 g of fumaric acid and heating the mixture on the steam bath. After a few mins, the fumarate salt precipitated from the solution. The mixture was allowed to stand overnight at ambient temperature and the salt was collected. Two recrystallizations from methanol-ether yielded 2.8 g (46%) of product, mp 203°–205° C.

ANALYSIS: Calculated for $C_{18}H_{20}N_4 \cdot C_4H_4O_4$: 64.69%C, 5.92%H, 13.72%N. Found: 64.69%C, 6.00%H, 13.77%N.

EXAMPLE 60

1-(3-Hydroxy-1-propyl)-3-(1-methyl-4-piperidinyl)-1H-indazole

To a stirred suspension of 0.35 g of a 50–55% oil dispersion of lithium aluminum hydride in 50 ml of tetrahydrofuran was added, dropwise, under nitrogen, 2.4 g of 1-(3-ethoxycarbonyl-1-ethyl)-3-(1-methyl-4-piperidinyl)-1H-indazole in 25 ml of tetrahydrofuran. The reaction mixture was stirred under reflux for 1.5 hrs, cooled in an ice-salt bath, and water was added dropwise. The reaction mixture was filtered. The filter cake was washed with tetrahydrofuran and the filtrate concentrated in vacuo to give an oil. The oil was taken up in dichloromethane. The dichloromethane was washed with water, dried over anhydrous magnesium sulfate and the solvent removed in vacuo to yield 1.7 g (81%) of product. The product was combined with that from another experiment (total 3.2 g) and recrystallized twice from ethyl acetate-hexane to yield the analytical sample, mp 96°–98° C.

ANALYSIS: Calculated for $C_{16}H_{23}N_3O$: 70.29%C, 8.48%H, 15.37%N. Found: 70.53%C, 8.34%H, 15.47%N.

EXAMPLE 61

4-(4-Bromo-2-fluorobenzoyl)-1-acetylpiperidine

To a stirred suspension of 21.1 g of aluminum chloride and 63 ml of 3-fluorobromobenzene was added, portionwise, 16.0 g of 1-acetylisonipecotoyl chloride. The reaction mixture was stirred under reflux for 4 hrs. Most of the supernatant 3-fluorobromobenzene was decanted and ice water was added. The aqueous mixture was extracted with dichloromethane and the extract was washed with water, dried over anhydrous magnesium sulfate and the solvent concentrated to give an oil. The oil was triturated with ether and a solid separated out. Recrystallization of the solid from cyclohexane gave 4.9 g (19%) of product. Recrystallization from cyclohexane yielded the analytical sample, mp 111°–113° C.

ANALYSIS: Calculated for $C_{14}H_{15}BrFNO_2$: 51.23%C, 4.61%H, 4.24%N. Found: 51.40%C, 4.61%H, 3.92%N.

EXAMPLE 62

1-(3-Ethoxycarbonyl-ethyl)-3-(1-methyl-4-piperidinyl)-1H-indazole

To a stirred suspension, under nitrogen, of 1.7 g of a 50% oil dispersion of sodium hydride in 75 ml of dimethylformamide was added, dropwise, 6.0 g of 3-(1-methyl-4-piperidinyl)-1H-indazole in 30 ml of hot dimethylformamide. Upon completion of the addition, the reaction mixture was stirred at ambient temperature for 1 hr and a solution of 6.5 g of ethyl 3-bromopropionate was added dropwise. The reaction mixture was stirred at ambient temperature for 3 hrs and then poured into water. The aqueous mixture was extracted with ethyl acetate and the extracts were washed with water, dried over anhydrous magnesium sulfate and filtered. Evaporation of the filtrate under vacuum gave 6.5 g (70.8%) of product, as an oil.

EXAMPLE 63

6-Bromo-3-(4-piperidinyl)-1H-indazole

A mixture of 9.6 g of 1-acetyl-4-(4-bromo-2-fluorobenzoyl)piperidine and 50 ml of hydrazine hydrate was stirred in an autoclave at 135°–140° C. for 20 hr. The reaction mixture was quenched with water and the solid was collected. The solid was recrystallized from acetonitrile (charcoal) to yield 2.6 g (32%) of product, mp 163°–165° C.

ANALYSIS: Calculated for $C_{12}H_{14}BrN_3$: 51.44%C, 5.04%H, 15.00%N. Found: 51.35%C, 5.05%H, 15.23%N.

EXAMPLE 64

3-(1-Methyl-4-piperidinyl)-1-methyl-1H-indazole hydrochloride monohydrate

A mixture of 10.0 g of 4-(2-fluorobenzoyl)-1-methylpiperidine and 2.70 g of methyl hydrazine in 250 ml of n-butanol was heated under reflux for 16 hrs. The reaction mixture was then poured into water and extracted with ethyl acetate. The organic layer was dried over anhydrous magnesium sulfate and concentrated to an oil. An ethereal hydrogen chloride solution was added to the oil. The salt was recrystallized twice from ethanol-ether to yield 3.1 g (26%) of product, mp 198°–200° C.

ANALYSIS: Calculated for $C_{14}H_{19}N_3.HCl.H_2O$: 59.25%C, 7.81%H, 14.81%N. Found: 59.81%C, 7.67%H, 14.81%N.

EXAMPLE 65

3-(1-Methyl-4-piperidinyl)-1-[3-(trifluoromethyl)-phenyl]-1H-indazole

To a stirred suspension of 4.9 g of a 50% oil dispersion of sodium hydride in 60 ml of dimethylformamide was added dropwise a solution a 10.0 g of 3-(1-methyl-4-piperidinyl)-1H-indazole in 80 ml of hot dimethylformamide. The reaction mixture was stirred for 1 hr and then 15.2 g of 3-fluorobenzotrifluoride was added. The reaction was heated at 90° C. for 22 hrs, cooled and poured into water. The aqueous mixture was extracted with ether. The ethereal extracts were dried over anhydrous magnesium sulfate and concentrated to give an oil. The oil was flash chromatographed (silica gel, diethylamine-ethyl acetate (1:9)). Evaporation of the appropriate fractions followed by recrystallization twice from hexane yielded 2.96 g (18%) of product, mp 103°–105° C.

ANALYSIS: Calculated for $C_{20}H_{20}F_3N_3$: 66.84%C, 5.61%H, 11.69%N. Found: 66.74%C, 5.64%H, 11.76%N.

EXAMPLE 66

3-(1-Methyl-4-piperidinyl)-1-phenyl-1H-indazole hydrochloride

A mixture of 14.6 g of 4-(2-fluorobenzoyl)-1-methylpiperidine, 12.0 g of phenylhydrazine hydrochloride and 16.0 g of sodium acetate in 280 ml of n-butanol was heated under reflux for 3.5 hrs. The reaction mixture was cooled, filtered and concentrated. The residue was washed with ether to yield 17 g (83%) of 4-(2-fluorobenzoyl)-1-methylpiperidine phenylhydrazone, mp 131°–134° C.

To a solution of 10.0 g of 4-(2-fluorobenzoyl)-1-methylpiperidine phenylhydrazone in 110 ml of dimethylformamide was added 2.42 g of a 50% oil dispersion of sodium hydride. The reaction mixture was stirred at 80° C. for 2 hrs, cooled and poured into water. The aqueous mixture was extracted with ethyl acetate. The extracts were dried over anhydrous magnesium sulfate and concentrated to an oil. The oil was dissolved in ether and a solution of hydrogen chloride gas in ether was added. The salt was washed with ether and recrystallized twice from acetonitrile to yield 3.66 g (35%) of product, mp 277°–279° C.

ANALYSIS: Calculated for $C_{19}H_{21}N_3.HCl$: 69.61%C, 6.76%H, 12.82%N. Found: 69.47%C, 6.77%H, 12.90%N.

EXAMPLE 67

1-(4-Fluorophenyl)-3-(1-methyl-4-piperidinyl)-1H-indazole hydrochloride

A stirred mixture of 21.8 g of 4-(2-fluorobenzoyl)-1-methylpiperidine, 20.25 g of 4-fluorophenyl hydrazine hydrochloride and 25.0 g of sodium acetate in 420 ml of n-butanol was heated under reflux for 8 hrs. The mixture was cooled, filtered, and concentrated. The residue was washed with ether to give 7.5 g (23%) of 4-(2-fluorobenzoyl)-1-methylpiperidine 4-fluorophenylhydrazone, mp 125°–126° C.

To a solution of 7.5 g of 4-(2-fluorobenzoyl)-1-methylpiperidine 4-fluorophenylhydrazone in 80 ml of dimethylformamide was added 2.4 g of a 50% oil dispersion of sodium hydride. The reaction mixture was stirred at 80° C. for 2 hrs, cooled and poured into water.

The aqueous mixture was extracted with ethyl acetate. The extracts were dried over anhydrous magnesium sulfate and concentrated to an oil. The oil was dissolved in ether and an ethereal hydrogen chloride solution was added. The salt was washed with ether and recrystallized twice from acetonitrile to yield 2.0 g of product. The product was combined with 2.1 g of a previously prepared sample and recrystallized from acetonitrile to give 3.0 g (19%) of product, mp 198°–199° C.

ANALYSIS: Calculated for $C_{19}H_{20}FN_3 \cdot HCl$: 65.99%C, 6.12%H, 12.15%N. Found: 65.87%C, 6.07%H, 12.18%N.

EXAMPLE 68

6-Fluoro-1-methyl-3-(4-piperidinyl)-1H-indazole hydrochloride

A solution of 5.0 g of 1-acetyl-4-(2,4-difluorobenzoyl)piperidine, 1.2 g of methylhydrazine and 50 ml of n-butanol was heated under reflux for 16 hrs. After cooling, the solvent was removed in vacuo and the residue was diluted with water. The aqueous mixture was made basic with ammonium hydroxide and extracted with dichloromethane. The organic extract was washed with water, dried over anhydrous magnesium sulfate and concentrated to yield 5.6 g of 3-(1-acetyl-4-piperidinyl)-6-fluoro-1-methyl-1H-indazole as an oil.

A solution of 16.8 g of 3-(1-acetyl-4-piperidinyl)-6-fluoro-1-methyl-1H-indazole and 100 ml of 6N hydrochloric acid was heated under reflux for 4 hrs. The solution was cooled in an ice bath, 50% aqueous sodium hydroxide was added, dropwise, with stirring and the mixture was extracted with ethyl acetate. Concentration of the organic extract gave an oil. The oil was dissolved in ethyl acetate and a saturated solution of ethyl acetate-hydrogen chloride was added. The salt was recrystallized twice from trichloromethane-ether and then from isopropanol (charcoal) to yield 3.0 g (21%) of product, mp 256°–258° C.

ANALYSIS: Calculated for $C_{13}H_{16}FN_3 \cdot HCl$: 57.88%C, 5.98%H, 15.58%N. Found: 57.58%C, 6.34%H, 15.48%N.

EXAMPLE 69

4-(1H-Indazol-3-yl)piperidine-1-carboximidic acid methyl ester

To a stirred suspension of 4-(1H-indazol-3-yl)piperidine-1-carbonitrile (7.9 g, 0.024 mole) in methanol (15 ml) was added 4.9 ml of 25% solution of sodium methoxide in methanol. The solution was stirred at ambient temperature for 16 hours, made neutral to pH paper with glacial acetic acid, and extracted with ether. The aqueous solution was made basic with concentrated NH$_4$OH, and extracted thrice with CH$_2$Cl$_2$ (35 ml). The organic extracts were combined, washed (H$_2$O), dried (MgSO$_4$) and the solvent removed in vacuo to yield 6.6 g of an oil. The oil was triturated with hexane and the resultant solid collected (5.4 g). Recrystallization from CH$_3$CN (twice) yielded 3.5 g (56.8%) of 4-(1H-indazol-3-yl)piperidine-1-carboximidic acid methyl ester having a melting point of 153°–155° C.

ANALYSIS: Calculated for $C_{14}H_{18}N_4O$: 65.09%C, 7.02%H, 21.69%N. Found: 65.27%C, 6.96%H, 21.74%N.

EXAMPLE 70 a. 4-(6-Fluoro-1H-indazol-3-yl)piperidine-1-carbonitrile

To a mixture of NaHCO$_3$ (2.3 g., 1.027 mol), BrCN (1,5 g, 0.0141 mol., 97%) and dimethyl sulfoxide (DMSO) [20 ml.], was added dropwise 6-fluoro-3-(4-piperidinyl)-1H-indazole (3.0 g., 0.014 mol) dissolved in 30 ml. of warm DMSO. After two hours at ambient temperature the reaction mixture was poured into water and the resultant solid was collected, dried and yielded 3.6 g. of 4-(6-fluoro-1H-indazol-3-yl)piperidine-1-carbonitrile, m.p. 143°–145° C.

b. 4-(6-fluoro-1H-indazol-3-yl)piperidine-1-carboximidic acid methyl ester

A solution of 4-(6-fluoro-1H-indazol-3-yl)piperidine-1-carbonitrile (3.0 g. 0.012 mol) of Example 70a, methanol (35 ml) and 25% sodium methoxide in methanol (2.5 ml) was stirred at ambient temperature for 16 hours. Most of the methanol was removed in vacuo and the residue diluted with water. The aqueous mixture was extracted with CH$_2$Cl$_2$. The extract was washed (H$_2$O), dried (Na$_2$SO$_4$) and the solvent evaporated to yield 3.0 g of a solid. The material was recrystallized from toluene to give 2.4 g (72%) of 4-(6-fluoro-1H-indazol-3-yl)piperidine-1-carboximidic acid methyl ester, m.p. 162°–164° C.

ANALYSIS: Calculated for $C_{14}H_{17}FN_4O$: 60.85%C, 6.20%H, 20.28%N. Found: 61.39%C, 6.28%H, 20.09%N.

EXAMPLE 71

4-(6-Fluoro-1-methyl-1H-indazol-3-yl)piperidine-1-carboximidic acid methyl ester To a stirred mixture of cyanogen bromide (2.2 g, 0.021 mol), sodium bicarbonate (3.5 g) and dimethyl sulfoxide (DMSO) (40 ml) was added 6-fluoro-1-methyl-3-(4-piperidinyl)-1H-indazole (5.0 g, 0.021 mol) free base of Example 68 in DMSO (50 ml). The reaction was stirred at ambient temperature for 2 hours and then poured into water. The cyanamide separated from solution and was collected to yield 4.9 g of a solid. Recrystallization from ethylacetate-hexane yielded 3.6 g (66%) of 4-(6-fluoro-1-methyl-1H-indazol-3-yl)piperidine-1-carbonitrile,, mp. 133°–136° C.

To a stirred mixture of 4-(6-fluoro-1-methyl-1H-indazol-3-yl)piperidine-1-carbonitrile (3.4 g, 0.013 mole) and methanol (40 ml) was added a 25% sodium methoxide-methanol solution (2.5 ml). The mixture was warmed briefly to effect solution and was then stirred at ambient temperature for 16 hours. The methanol was concentrated and the residue was diluted with water. The resulting precipitate was collected to yield 3.8 g of the product as a solid. The material was recrystallized from toluene-hexane to yield 3.0 g of 4-(6-fluoro-1-methyl-1H-indazol-3-yl)piperidine-1-carboximidic acid methyl ester, mp 132°–135° C.

ANALYSIS: Calculated for $C_{15}H_{19}FN_4O$: 62.05%C, 6.59%H, 19.30%N. Found: 61.95%C, 6.54%H, 19.13%N.

EXAMPLE 72

4-(6-Chloro-3H-indazol-3-yl)piperidine-1-carboximidic acid methyl ester

To a stirred mixture of cyanogen bromide (1.8 g, 0.017 mol), sodium bicarbonate (2.80 g) and dimethyl sulfoxide (DMSO) (40 ml) was added dropwise 6-chloro-3-(4-piperidinyl)-1H-indazole (4.0 g, 0.017 mol) of Example 52 dissolved in DMSO (50 ml). The reaction was stirred at ambient temperature for 1 hour and poured into water. The resulting solid was collected, dried and weighed 4.0 g. Recrystallization from toluene-hexane afforded 3.1 g (70%) of 4-(6-chloro-1H-indazol-3-yl)piperidine-1-carbonitrile, m.p. 180°–188° C. To a stirred mixture of 4-(6-chloro-1H-indazol-3-yl)piperidine-1-carbonitrile (3.0 g., 0.015 mol) in methanol (30 ml) was added a solution of 25% sodium methoxide in methanol (2.5 ml). The reaction was warmed on a steam bath to effect solution and then stirred at ambient temperature for 16 hours. Most of the methanol was removed in vacuo and the residue was diluted with water. An initial oil solidified and 3.5 g of a solid was collected. This was recrystallized from methanol-water to yield 2.9 g (66%) of 4-(6-chloro-1H-indazol-3-yl)piperidine-1-carboximidic acid methyl ester, mp 173°–175° C.

ANALYSIS: Calculated for $C_{14}H_{19}ClN_4O$: 57.43%C, 5.85%H, 19.14%N. Found: 57.44%C, 5.87%H, 19.34%N.

EXAMPLE 73

4-(1-Phenyl-1H-indazole-3-yl)piperidine-1-carbonitrile

To a mixture of cyanogen bromide (5.76 g, 0.054 moles) and $K_2CO_3$ (8.82 g, 0.064 moles) in dimethylsulfoxide (110 ml) was added 3-(1-methyl-4-piperidinyl)-1-phenyl-1H-indazole (14.8 g, 0.051 moles) of Example 66 in dimethylsulfoxide (DMSO) (15 ml). The reaction was stirred at ambient temperature for 16 hours and then poured into water and extracted with ether. A precipitate formed in the ether which was collected and then the ether was concentrated to yield additional product. The crude product (11.5 g) was recrystallized three times from isopropyl alcohol which yielded 6.75 g (37%) of 4-(1-phenyl-1H-indazol-3-yl)piperidine-1-carbonitrile, m.p. 124°–125° C.

ANALYSIS: Calculated for $C_{19}H_{18}N_4$: 75.47%C, 6.00%H, 18.52%N. Found: 75.59%C, 6.07%H, 18.61%N.

EXAMPLE 74

4-[1-(2-Fluorophenyl)-1H-indazol-3-yl]piperidine-1-carbonitrile

To a stirred mixture of cyanogen bromide (15.5 g, 0.146 moles) and potassium carbonate (23.7 g, 0.167 moles) in dimethylsulfoxide (DMSO) [300 ml] was added dropwise a solution of 1-(2-fluorophenyl)-3-(1-methyl-4-piperidinyl)-1H-indazole, the free base of example 36, (42.0 g, 0.137 moles) in dimethylsulfoxide (40 ml). The reaction temperature rose to 36° C. and the mixture was stirred at ambient temperature for 2.5 days. The reaction mixture was then poured into $H_2O$ and the product extracted with ether. The ether was dried ($MgSO_4$) and concentrated which left 40 g of a solid. The product was recrystallized 5 times from isopropyl alcohol which yielded 13.6 g (31%) of 4-[1-(2-fluorophenyl)-1H-indazol-3-yl]piperidine-1-carbonitrile, m.p. 119°–121° C.

ANALYSIS: Calculated for $C_{19}H_{17}FN_4$: 71.33%C, 5.35%H, 17.49%N. Found: 71.13%C, 5.62%H, 17.43%N.

EXAMPLE 75

N-Phenyl-4-(6-fluoro-1-phenyl-1H-indazol-3-yl)piperidine-1-carboxamide

To a solution of 6-fluoro-1-phenyl-3-(4-piperidinyl)-1H-indazole the free base of Example 98 (1.8 g, 0.0061 mol) in toluene (25 ml) was added phenyl isocyanate (0.8 g, 0.0067 mol), and the solution was warmed at 100° C. (steam bath) for 15 minutes. Upon cooling to ambient temperature, a solid precipitated from solution. Cyclohexane was added, and the product was collected yielding 2.1 g (83%) of a solid, mp 163°–165° C. This material was combined with a 2.5 g sample from another reaction, and recrystallization from toluene-cyclohexane and then from toluene yielded 3.4 g of N-phenyl-4-(6-fluoro-1-phenyl-1H-indazol-3-yl)piperidine-1-carboxamide, mp 163°–165° C.

ANALYSIS: Calculated for $C_{25}H_{23}FN_4O$: 72.44%C, 5.59%H, 13.52%N. Found: 72.40%C, 5.62%H, 13.50%N.

EXAMPLE 76

N-Phenyl-4-[1-(2-fluorophenyl)-1H-indazol-3-yl]piperidine-1-carboxamide

A stirred mixture of 4-[1-(2-fluorophenyl)-1H-indazole-3-yl]piperidine-1-carbonitrile of Example 74 (32.7 g, 0.102 moles) and 25% $H_2SO_4$ (300 ml) was refluxed for 20 hours. The mixture was cooled, poured into water and basified with 25% NaOH solution. The product was extracted with dichloromethane, dried ($MgSO_4$) and concentrated which yielded 28 g of an oil. The oil was triturated with acetone to produce 14 g (47%) of product as a solid. To a suspension of the solid (4.0 g, 0.0136 moles) in toluene (100 ml) was added dropwise phenyl isocyanate (4.4 ml, 0.041 moles). The mixture was then stirred at reflux for 12 hours. Concentration of the reaction mixture yielded 6.8 g of an oil. The oil was purified using high pressure liquid chromatography (silica gel, 40% ethyl acetate/hexane) which yielded 2.65 g of a solid. The solid was recrystallized from toluene-hexane which yielded 2.25 g (40%) of N-phenyl-4-(6-fluoro-1-phenyl-1H-indazol-3-yl)piperidine-1-carboxamide, m.p. 166°–168° C.

ANALYSIS: Calculated for $C_{25}H_{23}FN_4O$: 72.455C, 5.59%H, 13.52%N. Found: 72.60%C, 5.69%H, 13.24%N.

EXAMPLE 77

4-[1-[4-(Trifluoromethyl)phenyl]-1H-indazol-3-yl]-1-piperidine carboxamide hydrobromide A mixture of 4-[1-[4-(trifluoromethyl)phenyl]-1H-indazol-3-yl]piperidine-1-carbonitrile of Example 101 (5.0 g, 0.0135 moles) and $NaOCH_3$ (3.1 ml of a 25% methanol solution, 0.0136 moles) in methanol (30 ml) was warmed to effect solution and then stirred at ambient temperature for 3 hours. The mixture was poured into $H_2O$, extracted with $CHCl_3$, and dried with $MgSO_4$. Concentration produced an oil which was triturated with hexane to yield 3.93 g (72%) of an imidate as a solid, mp 96°–98° C. A mixture of the imidate (3.9 g, 0.0097 moles) and a HBr solution (40 ml of a 48% solution) was heated at 90° C. for 17 hours. The mixture was cooled, causing the product to precipitate from the solution. The product was collected, washed with ether, and then recrystallized from isopropyl alcohol-ether to yield 2.1 g (46%) of 4-[1-[4-(trifluoromethyl)-phenyl]-1H-indazol-3-yl]piperidine-1-carboxamide hydrobromide, mp 130°–132°.

ANALYSIS: Calculated for $C_{20}H_{19}F_3N_4O \cdot HBr$: 51.19%C, 4.30%H, 11.94%N. Found: 51.47%C, 4.31%H, 11.84%N.

EXAMPLE 78

N-Phenyl-4-[1-[4-(trifluoromethyl)phenyl]-1H-indazol-3-yl]piperidine-1-carboxamide A stirred mixture of 4-[1-[4-(trifluoromethyl)phenyl]-1H-indazol-3-yl]piperidine-1-carbonitrile of Example 77 (15 g, 0.041 moles) and 25% $H_2SO_4$ (100 ml) was refluxed for 20 hours. The mixture was cooled, poured into $H_2O$, and basified with a 25% NaOH solution. The product was extracted (dichloromethane), dried ($MgSO_4$), and concentrated to yield 13 g (93%) of 1-[4-(trifluoromethyl)phenyl]-3-(4-piperidinyl)-1H-indazole as an oil. To a stirred suspension of the indazole (4.0 g, 0.012 moles) in toluene (60 ml) was added phenyl isocyanate (1.38 ml, 0.013 moles). The reaction temperature rose to 35° C. and the product precipitated from the solution. The product was collected and recrystallized twice from toluene to yield 3.57 g (66%) of N-phenyl-4-[1-(4-trifluoromethyl)phenyl]-1H-indazol-3-yl]piperidine-1-carboxamide, m.p. 190°–192° C.

ANALYSIS: Calculated for $C_{26}H_{23}F_3N_4O$: 67.23%C, 4.99%H, 12.06%N. Found: 67.16%C, 5.05%H, 11.96%N.

EXAMPLE 79

N-Methyl-4-(6-fluoro-1-phenyl-1H-indazol-3-yl)piperidine-1-carboxamide

To a solution of 6-fluoro-1-phenyl-3-(4-piperidinyl)-1H-indazole of Example 98 (4.0 g, 0.014 mol) in toluene (50 ml) was added methyl isocyanate (0.94 g. 0.016 mol). The reaction warmed on a steam bath for 15 minutes, and upon cooling to ambient temperature a solid precipitated. Hexane was added and the solid was filtered to yield 4.0 g of a urea. The compound was recrystallized twice from toluene to yield 3.4 g (69%) of N-methyl-4-(6-fluoro-1-phenyl-1H-indazol-3-yl)piperidine-1-carboxamide, mp 163°–165° C.

ANALYSIS: Calculated for $C_{20}H_{21}FN_4O$: 68.18%C, 6.00%H, 15.90%N. Found: 68.33%C, 6.00%H, 15.46%N.

EXAMPLE 80

N-Phenyl-4-(6-fluoro-1-phenyl-1H-indazol-3-yl)piperidine-1-carbothioamide

A solution of 6-fluoro-1-phenyl-3-(4-piperidinyl)-1H-indazole free base of Example 98 (3.5 g, 0.012 mol) and phenyl isothiocyanate (2.0 g, 0.015 mol) in toluene (20 ml) was heated on a steam bath for 15 minutes. An additional 0.2 ml of phenyl isothiocyanate was added and the solution was heated again for 15 minutes. The reaction was then stirred at ambient temperature for 16 hours, and a solid precipitated from solution. Hexane was added to the mixture, and the solid collected to yield 4.5 g of a thiourea. Two recrystallizations from toluene yielded 3.2 g (64%) of N-phenyl-4-(6-fluoro-1-phenyl-1H-indazol-3-yl)piperidine-1-carbothioamide, mp 151°–153° C.

ANALYSIS: Calculated for $C_{25}H_{23}FN_4S$: 69.75%C, 5.38%H, 13.02%N. Found: 69.87%C, 5.34%H, 12.91%N.

EXAMPLE 81

N-Methyl-4-[1-(4-(trifluoromethyl)phenyl)-1H-indazol-3-yl]piperidine-1-carboxamide A stirred mixture of 4-[1-(4-(trifluoromethyl)phenyl)-1H-indazol-3-yl]piperidine-1-carbonitrile of Example 101 (15 g, 0.041 moles) and 25% $H_2SO_4$ (100 ml) was refluxed for 20 hours. The mixture was cooled. poured into $H_2O$ and basified with a 25% NaOH solution. The product was extracted (dichloromethane), dried ($MgSO_4$), and concentrated to yield 13 g (93%) of 1-[4-(trifluoromethyl)phenyl]-3-(4-piperidinyl)-1H-indazole as an oil. To a stirred suspension of the indazole (4.0 g, 0.012 moles) in toluene (60 ml) was added methyl isocyanate (0.75 ml., 0.013 moles). The temperature of the reaction mixture rose to 35° C. following the addition. The mixture was stirred for 2 hours at ambient temperature and then concentrated to yield 4.6 g of a solid. The product was purified by high pressure liquid chromatography (3.5% methanol-$CHCl_3$; silica gel) and then recrystallized three times from toluene-hexane to yield 2.93 g (63%) of N-methyl-4-[1-(4-trifluoromethyl)-phenyl]-1H-indazol-3-yl]piperidine-1-carboxamide, m.p.: 150°–152° C.

ANALYSIS: Calculated for $C_{21}H_{21}F_3N_4O$: 62.68%C, 5.26%H, 13.92%N. Found: 62.91%C, 5.44%H, 13.84%N.

EXAMPLE 82

N-Methyl-4-[1-(4-fluorophenyl)-1H-indazol-3-yl]piperidine-1-carboxamide

A stirred mixture of 4-[1-(4-fluorophenyl)-1H-indazol-3-yl]piperidine-1-carbonitrile of Example 102 (30 g, 0.094 moles) and 25% $H_2SO_4$ (225 ml) was refluxed for 20 hours. The mixture was cooled, poured into $H_2O$, and basified with a 25% NaOH solution. The product was extracted (dichloromethane), dried ($MgSO_4$), and concentrated to yield 21 g (76%) of 1-(4-fluorophenyl)-3-(4-piperidinyl)-1H-indazole as an oil. To a stirred suspension of the indazole (5.0 g, 0.017 moles) in toluene (90 ml) was added methyl isocyanate (1.1 ml, 0.019 moles). The mixture was stirred for 16 hours at ambient temperature and then concentrated to yield 5.8 g of an oil. The oil was triturated with ether causing the product to solidify. The product was recrystallized twice from isopropyl alcohol-hexane to yield 3.44 g (58%) of N-methyl-4-[1-(4-fluorophenyl)-1H-indazol-3-yl]piperidine-1-carboxamide, m.p. 113°–115° C.

ANALYSIS: Calculated for $C_{20}H_{21}FN_4O$: 68.16%C, 6.01%H, 15.90%N. Found: 68.04%C, 5.95%H, 15.79%N.

EXAMPLE 83

N-Methyl-4-[1-(4-fluorophenyl)-1H-indazol-3-yl]piperidine-1-carbothioamide

A stirred mixture of 4-[1-(4-fluorophenyl)-1H-indazol-3-yl]piperidine-1-carbonitrile of Example 102 (30 g, 0.094 moles) and 25% $H_2SO_4$ (225 ml) was refluxed for 20 hours. The mixture was cooled, poured into $H_2O$, and basified with a 25% NaOH solution. The product was extracted (dichloromethane), dried (MgSO$_4$), and concentrated to yield 21 g (76%) of 1-(4-fluorophenyl)-3-(4-piperidinyl)-1H-indazole as an oil. To a stirred suspension of the indazole (4.0 g, 0.0135 moles) in toluene (70 ml) was added dropwise methyl isothiocyanate (1.5 ml, 0.022 moles). The mixture was stirred for 23 hours at ambient temperature during which time the product precipitated from the solution. The product was collected and recrystallized twice from isopropyl alcohol to yield 2.74 g (55%) of N-methyl-4-[1-(4-fluorophenyl)-1H-indazol-3-yl]piperidine-1-carbothioamide, m.p. 179°–181° C.

ANALYSIS: for C$_{20}$H$_{21}$FN$_4$S: 65.19%C, 5.74%H, 15.21%N. Found: 65.09%C, 5.77%H, 15.11%N.

EXAMPLE 84

4-[1-(4-Fluorophenyl)-1H-indazol-3-yl]piperidine-1-carboxamide

A mixture of 4-[1-(4-fluorophenyl)-1H-indazol-3-yl]piperidine-1-carbonitrile of Example 102 (8.0 g, 0.025 moles) and sodium methoxide (5.8 ml of a 25% methanol solution, 0.025 moles) in methanol (55 ml) was warmed to effect solution and then stirred at ambient temperatures for 3 hours. The mixture was poured into H$_2$O, extracted with CHCl$_3$, and dried with MgSO$_4$. Concentration produced 8.8 g (100%) of the imidate as an oil. A mixture of the imidate (8.8 g, 0.025 moles) and aqueous HBr (100 ml of a 48% solution) was heated at 90° C. for 2 hours. The mixture was then cooled, poured into H$_2$O, extracted (ethyl acetate), and dried (MgSO$_4$). Concentration produced an oil which was triturated with hexane to yield 5.5 g of product. The product was recrystallized thrice from toluene-hexane and then chromatographed on the high pressure liquid chromatograph (silica gel, 5% methanol/ethyl acetate) which yielded 4.7 g of an oil. Recrystallization from toluene followed by recrystallization from isopropyl alcohol yielded 2.70 g (32%) of 4-[1-(4-fluorophenyl)-1H-indazol-3-yl]piperidine-1-carboxamide, m.p. 145°–147° C.

ANALYSIS: Calculated for C$_{19}$H$_{19}$FN$_4$O: 67.44%C, 5.66%H, 16.56%N. Found: 67.56%C, 5.88%H, 16.55%N.

EXAMPLE 85

4-[1-[4-(Trifluoromethyl)phenyl]-1H-indazol-3-yl]piperidine-1-carboximidic acid methyl ester A mixture of 4-[1-(4-trifluoromethylphenyl)-1H-indazol-3-yl]-piperidine-1-carbonitrile of Example 101 (20.0 g, 0.054 moles) and sodium methoxide (12.4 ml of 25% sodium methoxide in methanol 0.054 moles) in methanol (120 ml) was warmed to effect solution and then stirred at ambient temperature for 3 hours. The mixture was poured into H$_2$O, extracted (CHCl$_3$), dried (MgSO$_4$), and concentrated to yield an oil. The oil was triturated with hexane which produced 19 g of a solid. The solid was recrystallized twice from toluene-hexane which yielded 14.2 g (65%) of 4-[1-[4-trifluoromethyl)-phenyl]-1H-indazol-3-yl]piperidine-1-carboximidic acid methyl ester, m.p. 113°–115° C..

ANALYSIS: Calculated for C$_{21}$H$_{21}$F$_3$N$_4$O 62.68%C, 5.26%H, 13.92%N. Found 62.58%C, 5.20%H, 13.91%N.

EXAMPLE 86

4-(6-Fluoro-1-phenyl-1H-indazol-3-yl)piperidine-1-carboxamide

A solution of 6-fluoro-1-phenyl-3-(4-piperidinyl)-1H-indazole free base of Example 98 (4.2 g, 0.0142 mol), nitrourea (1.5 g, 0.014 mol) and ethanol (100 ml) was refluxed for 4 hours. An additional 0.75 g more of the nitrourea was then added and the reaction was left to stand at ambient temperature for 16 hours. The ethanol was concentrated to yield a gum, which after standing in the presence of H$_2$O for 4 days yielded 2.8 g (58%) of a solid. This solid was combined with another sample, and the total (6.2 g) recrystallized from ethyl acetate-diethylamine to yield 4.0 g of a solid. The solid (3.7 g) was chromatographed on a preparative high pressure liquid chromatograph (HPLC) (silica gel) using CH$_2$Cl$_2$-methanol (4%) as the eluent. Evaporation of the appropriate fractions yielded 2.3 g of a solid, mp 147°–149° C. Recrystallization from isopropanol yielded 1.5 g of 4-(6-fluoro-1-phenyl-1H-indazol-3-yl)piperidine-1-carboxamide, m.p. 149°–151° C.

ANALYSIS: Calculated for C$_{19}$H$_{19}$FN$_4$O 67.44%C, 5.66%H, 16.56%N. Found 67.04%C, 5.88%H, 16.45%N.

EXAMPLE 87

(a) 6-chloro-1-phenyl-3-(4-piperidinyl)-1H-indazole

A mixture of 1-acetyl-4-(6-chloro-1-phenyl-1H-indazol-3-yl)piperidine (8.2 g; 0.023 mol) of Example 95(b) was stirred and refluxed with 6N HCl (75 ml) for 5 hours. The mixture was diluted with water and extracted with ethyl acetate. The ethyl acetate was evaporated and filtered. The aqueous solution was chilled, stirred and 50% NaOH was added dropwise. The resultant basic mixture was extracted with ethyl acetate and the organic extract was washed and dried and then concentrated to yield an oil which solidified on standing to yield 5.7 g of 6-chloro-1-phenyl-3-(4-piperidinyl)-1H-indazole.

(b)
4-(6-Chloro-1-phenyl-1H-indazol-3-yl)piperidine-1-carboxamide

To a stirred solution of 6-chloro-1-phenyl-3-(4-piperidinyl)-1H-indazole of Example 87 (a) (3.2 g, 0.01 mol) in acetone (100 ml) was added, all at once, nitrourea (2.4 g, 0.023 mol). The reaction was stirred at ambient temperature for 16 hours. A solid (1.5 g) was filtered, and the filtrate was concentrated to yield 3.4 of product as a foam. The product was combined with 2.0 g from another run and chromatographed on a preparative high pressure liquid chromatography (HPLC) [silica gel], eluting with CH$_2$Cl$_2$-methanol (4%). Upon evaporation of the appropriate fractions there remained 3.4 g of a foam which upon trituration with hexane gave 3.0 g of a solid. The solid was recrystallized from ethyl acetate to yield 2.1 g (33%) of 4-(6-chloro-1-phenyl-1H-indazol-3-yl)piperidine-1-carboxamide, m.p. 148°–150° C.

ANALYSIS: Calculated for C$_{14}$H$_{19}$ClN$_4$O 64.31%C, 5.40%H, 15.80%N. Found 64.38%C, 5.63%H, 15.86%N.

EXAMPLE 88

N,N-Dimethyl-4-[1-[4-(trifluoromethyl)phenyl]-1H-indazol]-3-yl]piperidine-1-carboxamide A stirred mixture of 4-[1-[4-(trifluoromethyl)phenyl]-1H-indazol-3-yl]piperidine-1-carbonitrile of Example 101 (15 g, 0.041 moles) and 25% $H_2SO_4$ (100 ml) was refluxed for 20 hours. The mixture was cooled, poured into $H_2O$, and basified with a 25% NaOH solution. The product was extracted (dichloromethane), dried ($MgSO_4$), and concentrated to yield 13 g (93%) of 1-[4-(trifluoromethyl)phenyl]-3-(4-piperidinyl)-1H-indazole as an oil. To a suspension of the indazole (4.3 g, 0.012 moles) and triethylamine (3.5 ml, 0.025 moles) in toluene (50 ml) was added dimethylcarbamyl chloride (1.26 ml, 0.014 moles). The reaction was stirred at ambient temperature for 21 hours. The mixture was then poured into $H_2O$, extracted ($CHCl_3$), dried ($MgSO_4$), and concentrated to yield 5.08 g of an oil. The product was purified by high pressure liquid chromatography (HPLC) [silica gel, 100% ethyl acetate] to yield 3.6 g of product as an oil which crystallized upon standing. The product was washed with hexane and dried to yield 3.2 g (62%) of N,N-dimethyl-4-[1-[4-(trifluoromethyl)phenyl]-1H-indazol-3-yl]piperidine-1-carboxamide, m.p. 117°–119° C.

ANALYSIS: Calculated for $C_{22}H_{23}F_3N_4O$ 63.45%C, 5.57%H, 13.45%N. Found 63.22%C, 5.72%H, 13.34%N.

EXAMPLE 89

1-Formyl-4-[1-[4-(trifluoromethyl)phenyl]-1H-indazol-3-yl]piperidine

A stirred mixture of 4-[1-(4-trifluoromethylphenyl)-1H-indazol-3-yl]piperidine-1-carbonitrile of Example 101 (15 g, 0.041 moles) and 25% $H_2SO_4$ (100 ml) was refluxed for 20 hours. The mixture was cooled, poured into $H_2O$, and basified with a 25% NaOH solution. The product was extracted (dichloromethane), dried ($MgSO_4$), and concentrated which yielded 13 g (93%) of 1-[4-(trifluoromethyl)phenyl]-3-(4-piperidinyl)-1H-indazole as an oil. A mixture of formic acid (1 ml, 0.027 moles) and acetic anhydride (2.4 ml, 0.025 moles) was warmed at 55° C. for 1.5 hours. The solution was cooled to 30° C. and a suspension of the indazole (4.0 g, 0.012 moles) in ether (10 ml) was added. The mixture was stirred at ambient temperature for 3.5 hours and then poured into $H_2O$ and basified with a 5% NaOH solution. The product was extracted ($CHCl_3$), dried ($MgSO_4$) and concentrated to yield 5.1 g of an oil. The oil was purified on the high pressure liquid chromatograph (silica gel, 100% ethyl acetate) to yield 3.1 g (72%) of 1-formyl-4-[1-[4-(trifluoromethyl)phenyl]-1H-indazol-3-yl]piperidine, m.p. 109°–111° C.

ANALYSIS: Calculated for $C_{20}H_{18}F_3N_3O$: 64.34%C, 4.86%H, 11.25%N. Found: 64.17%C, 4.86%H, 11.11%N.

EXAMPLE 90

1-Formyl-4-[1-(4-fluorophenyl)-1H-indazol-3-yl]piperidine

A stirred mixture of 4-[1-(4-fluorophenyl-1H-indazol-3-yl]piperidine-1-carbonitrile of Example 102 (30 g, 0.094 moles) and 25% $H_2SO_4$ (225 ml) was refluxed for 20 hours. The mixture was cooled, poured into $H_2O$, and basified with a 25% NaOH solution. The product was extracted (dichloromethane), dried ($MgSO_4$), and concentrated to yield 21 g (76%) of 1-(4-fluorophenyl)-3-(4-piperidinyl)-1H-indazole as an oil. A mixture of formic acid (1 ml, 0.027 moles) and acetic anhydride (2.4 ml, 0.025 moles) was warmed at 65° C. for 1.5 hours. The solution was cooled to 30° C. and a suspension of the indazole (2.9 g, 0.010 moles) in ether (10 ml) was added. The mixture was stirred at ambient temperature for 3 hours, and then poured into $H_2O$ and basified with a 5% NaOH solution. The product was extracted ($CHCl_3$), dried ($MgSO_4$), and concentrated to yield 3.6 g of an oil. The oil was purified on the high pressure liquid chromatograph (silica gel, 100% ethyl acetate) to yield 2.05 g (65%) of 1-formyl-4-[1-(4-fluorophenyl)-1H-indazol-3-yl]piperidine, m.p. 128°–130° C.

ANALYSIS: Calculated for $C_{19}H_{18}FN_3O$: 70.57%C, 5.61%H, 12.99%N. Found: 70.11%C, 5.64%H, 12.83%N.

EXAMPLE 91

1-Acetyl-4-[1-[4-(trifluoromethyl)phenyl]-1H-indazol-3-yl]piperidine

A stirred mixture of 4-[1-[4-(trifluoromethyl)phenyl]-1H-indazol-3-yl]piperidine-1-carbonitrile of Example 101 (15 g. 0.041 moles) and 25% $H_2SO_4$ (100 ml) was refluxed for 20 hours. The mixture was cooled, poured into $H_2O$, and basified with 25% NaOH solution. The product was extracted (dichloromethane), dried ($MgSO_4$), and concentrated to yield 13 g (93%) of 1-[4-(trifluoromethyl)phenyl]-3-(4-piperidinyl)-1H-indazole as an oil. To a stirred mixture of the indazole (4.15 g. 0.012 moles) and triethylamine (3.35 ml. 0.024 moles) in toluene (50 ml) was added acetyl chloride (0.93 ml, 0.013 moles). The reaction was stirred at ambient temperature for 2 hours and then poured into $H_2O$. The product was extracted ($CHCl_3$), dried ($MgSO_4$), and concentrated to yield 4.3 g of an oil. The product was triturated with hexane and then recrystallized from $CCl_4$-hexane twice to yield 2.80 g of product. The product was further purified using high pressure liquid chromatography (silica gel, ethyl acetate)) to yield 2.1 g (45%) of 1-acetyl-4-[1-[4-(trifluoromethyl)phenyl]-1H-indazol-3-yl]piperidine, m.p. 148°–150° C.

ANALYSIS: Calculated for $C_{21}H_{20}F_3N_3O$: 65.11%C, 6.20%H, 10.85%N. Found: 64.92%C, 5.22%H, 10.73%N.

EXAMPLE 92

(a) 1-Acetyl-4-(4-bromo-2-fluorobenzoyl)piperidine phenylhydrazone

A mixture of 1-acetyl-4-(4-bromo-2-fluorobenzoyl)piperidine (16.6 g, 0.051 mol), phenylhydrazine hydrochloride (16.6 g, 0.11 mol), sodium acetate, (22.2 g) and isopropanol (250 ml) was stirred and refluxed for 4 hours. The reaction stood at ambient temperature for 16 hours, and then was filtered. The filtercake was treated with water, and the insoluble hydrazone was collected and dried to yield 13.7 g. The isopropanol filtrate was concentrated in vacuo to a solid, which when triturated with ether yielded 6.1 g more of the hydrazone (total yield 19.8 g; 93%). The phenylhydrazone was a mixture of the two geometric isomers. A 3.5 g sample of the compound was recrystallized from isopropanol to yield 2.1 g of the phenylhydrazone; mp 174°–176° C.

ANALYSIS: Calculated for $C_{20}H_{21}BrFNO_3$: 57.42%C, 5.06%H, 10.04%N. Found: 57.14%C, 5.01%H, 9.91%N.

(b)

1-Acetyl-4-(6-bromo-1-phenyl-1H-indazol-3-yl)piperidine

To a stirred solution, under $N_2$, of potassium t-butoxide (2.7 g, 0.024 mol) in THF (30 ml) was added, dropwise, a solution of 1-acetyl-4-(4-bromo-2-fluorobenzoyl)piperidine phenylhydrazone (8.4 g, 0.02 mol) of Example 92 (a) in THF (60 ml). After the addition was complete, the reaction was stirred at ambient temperature for 2 hours. The reaction was poured into $H_2O$, and the aqueous mixture was extracted with ethyl acetate. The extract was washed ($H_2O$), dried ($MgSO_4$) and the solvent concentrated to yield a foam. The foam was triturated with $H_2O$ to yield 7.0 g of a solid, m.p. 86°–89° C. Subsequent trituration of this solid with refluxing isopropyl ether yielded 6.2 g of a solid; m.p. 132°–134° C. The solid was recrystallized twice from ethyl acetate to yield 2.4 g (30%) of 1-acetyl-4-(6-bromo-1-phenyl-1H-indazol-3-yl)piperidine, mp 136°–138°.

ANALYSIS: Calculated for $C_{20}H_{20}BrN_3O$: 60.31%C, 5.06%H, 10.55%N. Found: 60.22%C, 5.03%H, 10.47%N.

EXAMPLE 93

1-Acetyl-4-[1-(4-fluorophenyl)-1H-indazol-3-yl]piperidine

A stirred mixture of 4-[1-(4-fluorophenyl)-1H-indazol-3-yl]piperidine-1-carbonitrile of Example 102 (30 g, 0.094 moles) and 25% $H_2SO_4$ (225 ml) was refluxed for 20 hours. The mixture was cooled, poured into $H_2O$, and basified with a 25% NaOH solution. The product was extracted (dichloromethane), dried ($MgSO_4$), and concentrated which yielded 21 g (76%) of 1-(4-fluorophenyl)-3-(4-piperidinyl)-1H-indazole as an oil.

To a stirred suspension of the indazole (3.5 g, 0.012 moles) and triethylamine (3.3 ml, 0.024 moles) in toluene (50 ml) was added acetyl chloride (0.92 ml, 0.013 moles). The solution was stirred for 2 hours at ambient temperature and then poured into $H_2O$. The product was extracted (chloroform), dried ($MgSO_4$), and concentrated to yield 4.4 g of an oil. The product was purified by high pressure liquid chromatography (silica gel, 100% ethyl acetate) and then triturated with hexane to yield 3.0 g of the product as a solid. The product was recrystallized once from toluene-hexane which produced 2.5 g (66%) of 1-acetyl-4-[1-(4-fluorophenyl)-1H-indazol-3-yl]piperidine, m.p. 99°–101° C.

ANALYSIS: Calculated for $C_{20}H_{20}FN_3O$: 71.20%C, 5.97%H, 12.45%N. Found: 71.26%C, 6.15%H, 12.43%N.

EXAMPLE 94

1-Acetyl-4-(6-methylthio-1-phenyl-1H-indazol-3-yl)piperidine

A mixture of 1-acetyl-4-(6-fluoro-1-phenyl-1H-indazol-3-yl)piperidine (6.8 g, 0.02 mol) of Example 39 hexamethylphosphoric triamide (70 ml) and sodium methylthiolate (2.2 g, 0.030 mol) was stirred, under nitrogen at 120° C. for 2 hours. After cooling to ambient temperature, $CH_3I$ (0.3 ml) was added, and then the reaction was poured into $H_2O$. The aqueous reaction mixture was extracted with ethyl acetate, the extract washed ($H_2O$), dried ($MgSO_4$) and the solvent was concentrated to an oil, which solidified to give 6.8 g of a solid. The solid was chromatographed on a silica gel column utilizing flash chromatography (50 mm diameter; eluting with $CH_2Cl_2$/acetone, 6:4). Evaporation of the appropriate fractions yielded 4.2 g of a solid. Recrystallization of the solid from isopropyl alcohol gave 3.6 g (45%) of 1-acetyl-4-(6-methylthio-1-phenyl-1H-indazol-3-yl)piperidine, mp 120°–122° C.

ANALYSIS: Calculated for $C_{21}H_{23}N_3OS$: 69.02%C, 6.34%H, 11.50%N. Found: 69.12%C, 6.44%H, 11.56%N.

EXAMPLE 95

(a) 1-Acetyl-4-(2,4-dichlorobenzoyl)piperidine phenylhydrazone

A stirred mixture of 1-acetyl-4-(2,4-dichlorobenzoyl)piperidine (33.0 g., 0.11 mol.), phenylhydrazine hydrochloride (34.2 g) and anhydrous sodium acetate in isopropanol was refluxed for 2 hours. The reaction was stirred overnight (about 16 hours) at ambient temperature. The reaction was filtered and the filter cake was washed with ether and then dispersed into water. The water insoluble solid was collected and dried to yield 21.3 g of the product, mp 209°–211° C. Concentration of the filtrate afforded an oil which on standing one week partially solidified. The resultant mixture was triturated with $CH_3CN$ and an additional 7.5 g of the product 1-acetyl-4-(2,4-dichlorobenzoyl)piperidine phenylhydrazone was obtained.

(b)

1-Acetyl-4-(6-chloro-1-phenyl-1H-indazol-3-yl)piperidine

To a stirred solution, under nitrogen of potassium tert-butoxide (6.5 g, 0.06 mol) in THF (250 ml) was added, portionwise, 1-acetyl-4-(2,4-dichlorobenzoyl)piperidine phenylhydrazone (19.3 g, 0.049 mol) of Example 95 (a). The solution was refluxed for 5 hours and then poured into $H_2O$. The aqueous mixture was extracted with ethyl acetate, the ethyl acetate washed ($H_2O$), dried ($MgSO_4$) and the solvent concentrated to yield an oil. The oil, upon being scratched with a glass rod, solidified to yield 16.4 g (95%) of a solid. A 5.0 g sample of the solid was chromatographed utilizing flash chromatography on a silica gel column, and eluting with $CH_2Cl_2$-acetone (30%). Upon evaporation of the appropriate fractions, there remained 4.3 g of a solid mp 128°–130° C. Recrystallization of the solid from ethyl acetate-hexane yielded 3.4 g of 1-acetyl-4-(6-chloro-1-phenyl-1H-indazol-3-yl)piperidine, mp 130°–132° C.

ANALYSIS: Calculated for $C_{20}H_{20}ClNO_3$: 67.88%C, 5.70%H, 11.78%N. Found: 67.92%C, 6.00%H, 11.83%N.

EXAMPLE 96

3-(1-Benzoyl-4-piperidinyl)-6-fluoro-1-phenyl-1H-indazole

To a stirred mixture of 6-fluoro-1-phenyl-3-(4-piperidinyl)-1H-indazole of Example 98(b) (3.5 g, 0.012 mol), $K_2CO_3$ (2.0 g) in toluene (15 ml) —$CHCl_3$ (15 ml) was added, dropwise, benzoyl chloride (2.3 g, 0.016 mol). The reaction was stirred and refluxed for 2 hours, and then poured into $H_2O$. The organic layer was separated, the aqueous layer re-extracted with $CHCl_3$ and the combined organic phase dried ($MgSO_4$). Upon concentration of the organic phase, there remained an oil, which solidified upon standing. The solid was triturated with cyclohexane and filtered to yield 4.6 g of product.

Recrystallization from ethanol-H₂O yielded 3.2 g (67%) of 3-(1-benzoyl-4-piperidinyl)-6-fluoro-1-phenyl-1H-indazole, mp 149°-151° C.

ANALYSIS: Calculated for $C_{25}H_{22}FN_3O$: 75.14%C, 5.55%H, 10.52%N. Found: 75.08%C, 5.62%H, 10.48%N.

EXAMPLE 97

6-Bromo-1-phenyl-3-(4-piperidinyl)-1H-indazole Hydrochloride

A mixture of 1-acetyl-4-(6-bromo-1-phenyl-1H-indazol-3-yl)piperidine of Example 92(b) (8.5 g, 0.02 mol) and 6N HCl (40 ml) was stirred and refluxed for 5 hours. The reaction was then stirred at ambient temperature for 8 hours and a solid was precipitated from solution. The solid was collected, washed with water and acetone, and dried under vacuum to yield 7.5 g of product. An analytical sample was obtained by recrystallization of a 4.0 g sample twice from ethanol, and this afforded 2.3 g (57%) of 6-bromo-1-phenyl-3-(4-piperidinyl)-1H-indazole hydrochloride, mp 255°-257° C.

ANALYSIS: Calculated for $C_{18}H_{18}BrN_3 \cdot HCl$: 55.11%C, 4.88%H, 10.71%N. Found: 54.77%C, 4.75%H, 10.58%N.

EXAMPLE 98

6-Fluoro-1-phenyl-3-(4-piperidinyl)-1H-indazole Hydrochloride

A mixture of 1-acetyl-4-(6-fluoro-1-phenyl-1H-indazol-3-yl)piperidine of Example 39 (8.0 g, 0.024 mol) and 6N HCl (50 ml) was stirred and refluxed for 4 hours. After cooling to ambient temperature, the mixture was diluted with H₂O, cooled in an ice bath, stirred, and dilute, aqueous NaOH was added dropwise, until the mixture was basic. The mixture was extracted with ethyl acetate, the extract washed (H₂O), dried (MgSO₄) and the solvent was concentrated in vacuo to yield 7.5 g of an oil. The oil was dissolved in ethyl acetate, and HCl (g) was discharged into the solution to precipitate 5.9 g of a white hydrochloride salt. The salt was recrystallized from isopropanol-ether to yield 4.6 g (58%) of product. An analytical sample was obtained by recrystallizing a 3.0 g sample again from isopropyl alcohol to yield 2.5 g of 6-fluoro-1-phenyl-3-(4-piperidinyl)-1H-indazole hydrochloride, mp 213°-215° C.

ANALYSIS: Calculated for $C_{18}H_{18}FN_3 \cdot HCl$: 65.28%C, 5.78%H, 12.69%N. Found: 65.41%C, 5.79%H, 12.44%N.

EXAMPLE 99

4-(1-Phenyl-1H-indazol-3-yl)piperidine-1-carboximidic acid methyl ester

A mixture of 4-(1-phenyl-1H-indazol-3-yl)piperidine-1-carbonitrile of Example 73 (4.0 g, 0.013 moles) and sodium methoxide (3 ml of 25% sodium methoxide in methanol, 0.013 moles) in methanol (30 ml) was warmed to effect solution and then stirred at ambient temperature for 16 hours. The solvent was removed which left an oil (4.5 g). The oil was dissolved in ether, washed with H₂O, and dried (MgSO₄). Removal of the ether left an oil which began to crystallize upon standing. Crystallization was enhanced by triturating the oil with hexane which produced 3.5 g of product. The product was recrystallized twice from hexane yielding 2.31 g (52%) of 4-(1-phenyl-1H-indazol-3-yl)piperidine-1-carboximidic acid methyl ester, mp 80°-83° C.

ANALYSIS: Calculated for $C_{20}H_{22}N_4O$: 71.83%C, 6.63%H, 16.75%N. Found: 71.76%C, 6.77%H, 16.75%N.

EXAMPLE 100

N-Methyl-4-[1-(2-fluorophenyl)-1H-indazol-3-yl]-piperidine-1-carboxamide

A stirred mixture of 4-[1-(2-fluorophenyl)-1H-indazol-3-yl]piperidine-1-carbonitrile of Example 74 (32.7 g, 0.102 moles) and 25% H₂SO₄ (300 ml) was refluxed for 20 hours. The mixture was then cooled, poured into H₂O and basified with 25% NaOH solution. The product was extracted with dichloromethane, dried (MgSO₄), and concentrated which yielded 28 g of an oil. The oil was triturated with acetone to produce 14 g of the solid amine product (47%). To a suspension of the amine (8.0 g, 0.027 moles) in toluene (140 ml) was added dropwise a solution of methyl isocyanate (3.4 ml, 0.057 moles) in toluene (20 ml). The reaction was stirred at ambient temperature for 2 hours. A small amount of insoluble material was filtered off and the filtrate was concentrated to yield 7.2 g of an oil. The oil was chromatographed twice (silica gel, first with ethyl acetate and then with 5% methanol-CHCl₃), which yielded 3.5 g of a solid. The solid was recrystallized twice from acetone-hexane which yielded 2.2 g (23%) of N-methyl-4-[1-(2-fluorophenyl)-1H-indazol-3-yl]piperidine-1-carboxamide, m.p. 131°-133° C.

ANALYSIS: Calculated for $C_{20}H_{21}FN_4O$: 68.15%C, 6.01%H, 15.90%N. Found: 68.44%C, 6.06%H, 16.15%N.

EXAMPLE 101

4-[1-[4-(Trifluoromethyl)phenyl]-1H-indazol-3-yl]piperidine-1 carbonitrile

To a stirred mixture of cyanogen bromide (14.4 g, 0.136 moles) and potassium carbonate (22.1 g, 0.16 moles) in dimethylsulfoxide (270 ml) was added dropwise 3-(1-methyl-4-piperidinyl)-1-[4-(trifluoromethyl)phenyl]-1H-indazole (45.78 g, 0.127 moles), the free base of example 9, dissolved in hot dimethylsulfoxide (250 ml). The reaction was stirred at ambient temperature for 19 hours and was then poured into H₂O and extracted (CH₂Cl₂). The organic layer was dried (MgSO₄) and concentrated to yield 34.5 g of product. The product was recrystallized three times from isopropyl alcohol to yield 18.6 g (39%) of 4[1-[4-(trifluoromethyl)phenyl]-1H-indazol-3-yl]piperidine-1-carbonitrile, mp 135°-136° C.

ANALYSIS: Calculated for $C_{20}H_{17}F_3N_4$: 64.86%C, 4.63%H, 15.13%N. Found: 64.68%C, 4.57%H, 15.01%N.

EXAMPLE 102

4-[1-(4-Fluorophenyl)-1H-indazol-3-yl]piperidine-1-carbonitrile

To a stirred mixture of cyanogen bromide (21.67 g, 0.204 moles) and potassium carbonate (33.2 g, 0.24 moles) in dimethyl sulfoxide (400 ml) was added dropwise a solution of 1-(4-fluorophenyl)-3-(1-methyl-4-piperidinyl)-1H-indazole (59.45 g, 0.192 moles), the free base of example 67, in hot dimethyl sulfoxide (375 ml). The reaction was stirred at ambient temperature for 4 days and then poured into H₂O (500 ml). The product was extracted (dichloromethane), dried (MgSO$_4$), and concentrated to yield 64 g of a solid. The product was recrystallized twice from isopropyl alcohol yield 35.7 g (58%) of 4-[1-(4-fluorophenyl)-1H-indazol-3-yl]piperidine-1-carbonitrile, mp 108°–110° C.

ANALYSIS: Calculated for C$_{19}$H$_{17}$FN$_4$: 71.23%C, 5.35%H, 17.49%N. Found: 71.24%C, 5.34%H, 17.45%N.

EXAMPLE 103

4-[1-(2-Cyanophenyl)-1H-indazol-3-yl]-piperidine-1-carbonitrile

To a stirred mixture of cyanogen bromide (7.16 g, 0.068 moles) and potassium carbonate (10.96 g, 0.079 moles) in dimethylsulfoxide (130 ml) was added dropwise a solution of 1-(2-cyanophenyl)-3-(1-methyl-4-piperidinyl)-1H-indazole of Example 109 (20.0 g, 0.063 moles) in hot (120 ml). The reaction was stirred at ambient temperature for 3 hours and then poured into H$_2$O. The product was extracted (CHCl$_3$), dried (MgSO$_4$), and concentrated to yield 18 g of a solid. The product was recrystallized twice from CHCl$_3$-hexane and once from acetone-hexane to yield 12.0 g (58%) of 4-[1-(2-cyanophenyl)-1H-indazol-3-yl]piperidine-1-carbonitrile, m.p. 188°–190° C.

ANALYSIS: Calculated for C$_{20}$H$_{17}$N$_5$: 73.37%C, 5.23%H, 21.39%N. Found: 73.47%C, 5.49%H, 21.41%N.

EXAMPLE 104

6-Bromo-1-benzoyl-3-(1-methyl-4-piperidinyl)-1H-indazole Hydrochloride Sesquihydrate A mixture of 6-bromo-3-(1-methyl-4-piperidinyl)-1H-indazole of Example 106(b) (3.0 g, 0.01 mol) and benzoyl chloride (8 ml) was heated at 100° C. (steam bath) for 2 hours. After the reaction had cooled, ether was added and 4.3 g of a hydrochloride salt was collected. After two recrystallizations from methanol-ether failed to purify the compound adequately, the compound was converted to its free base (2.0 g), and combined with 1.7 g of a sample from another run. The combined sample was then dissolved in ether and the hydrochloride salt was formed by the addition of ethereal HCl. The resulting salt (3.7 g) was recrystallized from ethanol-ether to yield 2.2 g (28%) of 6-bromo-1-benzoyl-3-(1-methyl-4-piperidinyl)-1H-indazole hydrochloride sesquihydrate, mp 271°–273° C.

ANALYSIS: Calculated for C$_{20}$H$_{20}$BrN$_3$O.HCl.1.5-H$_2$O: 52.02%C, 5.24%H, 9.10%N. Found: 52.14%C, 4.89%H, 9.10%N.

EXAMPLE 105

3-(1-Methyl-4-piperidinyl)-5-nitro-1H-indazole

To a stirred, cooled (ca.5° C.) solution of 3-(1-methyl-4-piperidinyl)-1H-indazole (10.7, 0.05 mol) of Example 4 in 83% H$_2$SO$_4$ (60 ml) was added, dropwise, concentrated HNO$_3$ (29 ml, 0.46 mol, sp. gr. 1.42) at such a rate so that the temperature of the reaction did not rise above 35° C. After complete addition of the nitric acid, the cooling bath was removed and the reaction was allowed to proceed at ambient temperature for 16 hours. The resultant solution was poured onto ice, and almost immediately a solid formed. The solid was filtered and after drying in a vacuum oven there remained 10.3 g of a salt, mp 263°–265° C. The compound was partially dissolved in warm H$_2$O and NH$_4$OH was added until the mixture was basic. The resulting solid was collected and dried to yield 7.4 g of product, mp 235°–237° C. Recrystallization (twice) from ethanol-H$_2$O yielded 3.8 g (29%) of 3-(1-methyl-4-piperidinyl)-5-nitro-1H-indazole, mp 237°–239° C.

ANALYSIS: Calculated for C$_{13}$H$_{16}$N$_4$O$_2$: 59.98%C, 6.20%H, 21.53%N. Found: 60.27%C, 6.27%H, 21.35%N.

EXAMPLE 106

(a) 4-(6-Bromo-1H-indazol-3-yl)piperidine-1-carboxylic acid methyl ester

To a stirred mixture of the 6-bromo-3-(4-piperidinyl)-1H-indazole (23.3 g, 0.083 mol), NaHCO$_3$ (30.6 g, 0.36 mol) in CHCl$_3$ (125 ml)—THF (125 ml) was added methyl chloroformate (27.9 ml, 34.1 g, 0.36 mol) in a dropwise manner. The mixture was stirred at ambient temperature for 16 hours. The reaction was poured into H$_2$O, and the organic layer was separated. The organic phase was dried (K$_2$CO$_3$) and the solution concentrated in vacuo to yield 42.6 g of an oil. The crude oil was dissolved in 200 ml of methanol and 6 ml of a 25% sodium methoxide in methanol added. The resultant solution was stirred at ambient temperature for 2 hours and then most of the methanol was removed in vacuo to leave a gum. The gum was diluted in H$_2$O and extracted with CH$_2$Cl$_2$. After washing (brine) and drying (K$_2$CO$_3$) concentration of the organic layer gave 8.4 g of product.

(b) 6-Bromo-3-(1-methyl-4-piperidinyl)-1H-indazole

To a stirred suspension of LiAlH$_4$ (6.2 g, 0.083 mol of a 50–55% oil dispersion) in THF (175 ml), under nitrogen, was added, dropwise, 4-(6-bromo-1H-indazol-3-yl)piperidine-1-carboxylic acid methyl ester (28.1 g, 0.083 mol) of Example 106(a). The reaction was refluxed for 1 hour, cooled in an ice bath, and water was added. The reaction was filtered and the filtrate was concentrated to yield 13.5 g of a solid. The solid was recrystallized from toluene to yield 10.2 g (42%) of a solid, mp 203°–205° C. An analytical sample was obtained by chromatography of a 3.4 g sample on a preparative HPLC (silica gel column) utilizing CH$_2$Cl$_2$-CH$_3$OH-(C$_2$H$_5$)$_2$NH (95:4:1) as eluent. After evaporation of the appropriate fractions there remained 2.8 g of 6-bromo-3-(1-methyl-4-piperidinyl)-1H-indazole, mp 205°–207° C.

ANALYSIS: Calculated for C$_{13}$H$_{16}$BrN$_3$: 53.07%C, 5.48%H, 14.28%N. Found: 53.17%C, 5.97%H, 14.38%N.

EXAMPLE 107

1-(2-Methoxyphenyl)-3-(1-methyl-4-piperidinyl)-1H-indazole fumarate

A mixture of 4-(2-fluorobenzoyl)-1-methylpiperidine (14.6 g. 0.066 moles) of Example 1, 2-methoxyphenylhydrazine hydrochloride (14.5 g, 0.083 moles) and sodium acetate (16.0 g, 0.195 moles) in n-butanol (280 ml) was refluxed for 7 hours. The mixture was cooled, filtered, and then concentrated to yield 22 g (100%) of an oil. To a solution of the oil (21.6 g, 0.063 moles) in DMF (220 ml) was added NaH (6.7 g, 0.139 moles, 50% oil dispersion). The mixture was stirred at 80° C. for 3 hours and then cooled and poured into H$_2$O. The aqueous mixture was extracted with ethyl acetate, dried (MgSO$_4$) and concentrated to yield 22 g of an oil. A portion of the oil (9.5 g) was purified using HPLC (silica gel, 100% methanol) to yield 4.5 g of an oil. The oil was dissolved in ether and a solution of fumaric acid in ether was added to form a salt. The salt was recrystallized three times from ethanol-ether to yield 2.15 g (15%) of 1-(2-methoxyphenyl)-3-(1-methyl-4-piperidinyl)-1H-indazole fumarate, m.p. 177°-178° C.

ANALYSIS: Calculated for $C_{20}H_{23}N_3O \cdot C_4H_4O_4$: 65.94%C, 6.21%H, 9.59%N. Found: 65.87%C, 6.34%H, 9.57%N.

EXAMPLE 108

1-Benzoyl-3-(1-methyl-4-piperidinyl)-5-nitro-1H-indazole Hydrochloride

A mixture of 3-(1-methyl-4-piperidinyl)-5-nitro-1H-indazole (4.0 g, 0.015 mol) of Example 105 and benzoyl chloride (12 ml) was heated at 100° C. (steam bath) for 4 hours. After cooling to ambient temperature, ether was added, the mixture stirred for 1 hour and then 4.9 g of a solid was collected. The solid was recrystallized twice from DMF and once from methanol to yield 2.3 g (38%) of 1-benzoyl-3-(1-methyl-4-piperidinyl)-5-nitro-1H-indazole hydrochloride, mp 297°-299° C.

ANALYSIS: Calculated for $C_{20}H_{20}N_4O_3 \cdot HCl$: 59.91%C, 5.28%H, 13.97%N. Found: 59.96%C, 5.31%H, 14.11%N.

EXAMPLE 109

1-(2-Cyanophenyl)-3-(1-methyl-4-piperidinyl)-1H-indazole

To a stirred suspension of NaH (19.6 g, 0.41 moles, 50% oil dispersion) in DMF (150 ml) was added dropwise a solution of 3-(1-methyl-4-piperidinyl)-1H-indazole (40.0 g, 0.186 moles) of Example 4 in hot DMF (300 ml). The mixture was stirred for 1 hour at ambient temperature and then 2-fluorobenzonitrile (22.2 ml, 0.20 moles) was added. The mixture was stirred at ambient temperature for 4 hours and then poured into H₂O. The product was extracted (ethyl acetate), dried (MgSO₄), and concentrated to yield 46 g of a solid. The product was recrystallized twice from isopropyl alcohol which yielded 27.0 g (46%) of 1-(2-cyanophenyl)-3-(1-methyl-4-piperidinyl)-1H-indazole, mp 117°-119° C.

ANALYSIS: Calculated for $C_{20}H_{20}N_4$: 75.92%C, 6.37%H, 17.71%N. Found: 75.94%C, 6.29%H, 17.66%N.

EXAMPLE 110

2-[3-(1-Methyl-4-piperidinyl)-1H-indazol-1-yl]benzamide

To a stirred suspension of NaH (4.0 g, 0.083 mol of a 50% oil dispersion) in DMF (100 ml), under nitrogen, was added, dropwise, 3-(1-methyl-4-piperidinyl)-1H-indazole (15.0, 0.07 mol) of Example 4 dissolved in hot DMF (100 ml). The reaction was stirred at ambient temperature for 0.75 hour and then 2-fluorobenzamide (11.6 g, 0.083 mol) was added dissolved in DMF (50 ml). The temperature of the reaction was then raised to 80° C. and kept there for 16 hours. The reaction was poured into H₂O, and the resulting solid which formed was collected and dried to yield 17.7 g. Subsequent extractive workup of the aqueous filtrate with ethyl acetate yielded an additional 2.5 g of the compound. The samples were combined and recrystallized from ethyl acetate and then from ethanol-water to yield 14.1 g (60%) of product mp 185°-187° C. An analytical sample was obtained by an additional recrystallization of a 3.0 g sample from ethanol-water which resulted in 2.3 g of 2-[3-(1-methyl-4-piperidinyl)-1H-indazol-1-yl]benzamide.

ANALYSIS: Calculated for $C_{20}H_{22}N_4O$: 71.83%C, 6.63%H, 16.75%N. Found: 71.90%C, 6.73%H, 16.72%N.

EXAMPLE 111

(a) 4-(2,5-difluorobenzoyl)-1-methylpiperidine

To a stirred suspension of Mg (9.62 g, 0.40 moles) in tetrahydrofuran (THF) (45 ml) was added a few ml of bromoethane to initiate the reaction followed by dropwise addition of freshly distilled 4-chloro-N-methyl-piperidine (42.3 g, 6.32 moles) in THF (140 ml). The reaction was initiated with a high intensity heat gun and controlled by the rate of addition of the piperidine. After the addition was complete, the reaction was refluxed for 1 hour. Next 2,5-difluorobenzonitrile (48.2 g, 0.318 moles) in THF (20 ml) was added and the reaction was refluxed for an additional 3 hours. The reaction was allowed to stand for 65 hours and was then poured into a solution of NH₄Cl/H₂O (120 g/400 ml). The mixture was heated on a steam bath for 2 hours, cooled and extracted with ether (500 ml.). Concentration produced an oil (50.6 g) which the product was distilled from (112° C. @ 0.5 mm) to yield 30.4 g (40%) of the product.

(b) 5-fluoro-1-phenyl-3-(1-methyl-4-piperidinyl)-1H-indazole Hydrochloride

A stirred mixture of 4-(2,5-difluorobenzoyl)-1-methylpiperidine (23.4 g, 0.098 moles), phenyl hydrazine hydrochloride (28.2 g, 0.196 moles) and sodium acetate (32.1 g, 0.392 moles) in ethanol (180 ml) was refluxed for 5 hours. The mixture was stirred overnight (about 16 hours) at ambient temperature and then filtered. The solid which was collected was washed with H₂O and then ether to yield 10.4 g of the hydrazone. The filtrate was concentrated and washed with ether to yield an additional 12.9 g of the hydrazone giving a total of 23.3 g (72%) of hydrazone, m.p. 146°-150° C. To a solution of the hydrazone (23.0 g, 0.070 moles) in DMF (230 ml) was added NaH (7.4 g, 0.154 moles, 50% oil dispersion). The mixture was stirred at 80° C. for 2 hours and then cooled and poured into H₂O. The aqueous mixture was extracted (ethyl acetate), dried (MgSO₄) and concentrated to yield 15.2 g of an oil. The hydrochloride salt was formed by dissolving a portion (4.0 g) of the oil in ether and adding ethereal HCl. The salt was washed with ether and recrystallized once from ethanol-ether and then once from isopropyl alcohol-hexane to yield 2.3 g (36%) of 5-fluoro-1-phenyl-3-(1-methyl-4-piperidinyl)-1H-indazole hydrochloride, m.p. 270°-272° C.

ANALYSIS: Calculated for $C_{19}H_{20}FN_3 \cdot HCl$: 65.99%C, 6.12%H, 12.15%N. Found: 65.92%C, 6.04%H, 12.20%N.

EXAMPLE 112

3-(1-Methyl-4-piperidinyl)-1-(2,3,4,5,6-pentafluorophenyl)-1H-indazole Hydrochloride Hemihydrate To a solution of 4-(2-fluorobenzoyl)-1-methylpiperidine (27.7 g, 0.125 mol) free base of example 1 in diethyl phosphite (50 ml ) was added a solution of pentafluorophenylhydrazine (27.7 g, 0.14 mol) in diethyl phosphite (70 ml). The reaction was heated on a steam bath for 2 hours and then poured into H₂O. The aqueous solution was made basic with NH$_4$OH, and the phenylhydrazone was deposited as an oil. The supernatant aqueous was separated from the oil, and the oil was taken up in ether. The ether was washed twice with H$_2$O, dried (MgSO$_4$) and the solvent was concentrated to yield 48.2 g of the pentafluorophenylhydrazone as an oil. To a stirred solution, under nitrogen, of the obtained 4-(2-fluorobenzoyl)-1-methylpiperidine pentafluorophenylhydrazone (46.5 g, 0.12 mol), in THF (500 ml), was added dropwise a solution of potassium tert-butoxide (15.2 g, 0.14 mol) in THF (400 ml). After complete addition of the alkoxide, the reaction was stirred at ambient temperature for 16 hours, and then poured into H$_2$O. The aqueous mixture was extracted with ether, the ether washed (H$_2$O), dried (MgSO$_4$) and the solvent was concentrated to yield 45.1 g of an oil. The oil was chromatographed on a Waters Prep 500 utilizing silica gel columns and eluting with ethyl acetate-diethylamine (10%). Concentration of the appropriate fractions yielded 10.9 g of the desired indazole as an uncrystallizable oil. The compound was converted to a hydrochloride salt with ethereal HCL to yield 9.1 g (17%) of a solid. The solid was recrystallized twice from CH$_3$CN to yield 3.0 g of 3-(1-methyl-4-piperidinyl)-1-(2,3,4,5,6-pentafluorophenyl)-1H-indazole hydrochloride hemihydrate, mp 249°–251° C.

ANALYSIS: Calculated for C$_{19}$H$_{16}$F$_5$N$_3$.HCL.0.5H$_2$O: 53.46%C, 4.25%H, 9.85%N. Found: 53.33%C, 4.02%H, 9.85%N.

EXAMPLE 113

4-[1-(4-Fluorophenyl)-1H-indazol-3-yl]piperidine-1-carboxylic acid methyl ester

A stirred mixture of 4-[1-(4-fluorophenyl)-1H-indazol-3-yl]piperidine-1-carbonitrile of Example 102 (30 g, 0.094 moles) and 25% H$_2$SO$_4$ (225 ml) was refluxed for 20 hours. The mixture was cooled, poured into H$_2$O, and basified with a 25% NaOH solution. The product was extracted (dichloromethane), dried (MgSO$_4$), and concentrated to yield 21 g (76%) of 1-(4-fluorophenyl)-3-(4-piperidinyl)-1H-indazole as an oil. To a stirred suspension of the indazole (3.5 g, 0.012 moles) and triethylamine (3.3 ml, 0.024 moles) in toluene (50 ml) was added methyl chloroformate (1.0 ml, 0.013 moles). The mixture was stirred for 17 hours at ambient temperature and was then poured into H$_2$O. The product was extracted (ethyl acetate), dried (Mg SO$_4$), and concentrated to yield 4.6 g of an oil. The product was purified on the HPLC (silica gel:ethyl acetate-hexane, 1:2) which produced 3.0 g (72%) of 4-[1-(4-fluorophenyl)-1H-indazol-3-yl]piperidine-1-carboxylic acid methyl ester, m.p. 95°–97° C.

ANALYSIS: Calculated for C$_{20}$H$_{20}$F$_1$N$_3$O$_2$: 67.97%C, 5.70%H, 11.89%N. Found: 67.71%C, 6.02%H, 11.93%N.

EXAMPLE 114

3-[1-[4,4-bis(4-fluorophenyl)butyl]-4-piperidinyl]-6-fluoro-1-phenyl-1H-indazole A stirred mixture, under nitrogen, of 6-fluoro-1-phenyl-3-(4-piperidinyl)-1H-indazole (1.5 g, 0.005 mol), the free base of Example 98, 4-chloro-1,1-bis-(4-fluorophenyl)butane (1.6 g, 0.0056 mol), Na$_2$CO$_3$ (0.6 g), a few crystals of KI and 4-methyl-2-pentanone (70 ml) was refluxed for 16 hours. The reaction was poured into H$_2$O, and the aqueous mixture extracted with ethyl acetate. The ethyl acetate was washed (H$_2$O), dried (MgSO$_4$) and the solvent was concentrated to a liquid. The liquid was dissolved in anhydrous ether and HCl (g) was added to precipitate a gum. The supernatant ether was decanted, H$_2$O was added to the gum, and the mixture was made basic with NH$_4$OH. The basic suspension was extracted with ether, the extract washed (H$_2$O), dried (MgSO$_4$), and the solvent was concentrated to yield 0.64 g (24%) of a solid. This material was combined with 2.9 g of a compound from another run and recrystallized from isopropyl ether to yield 2.1 g of 3-[1-[4,4-bis(4-fluorophenyl)butyl]-4-piperidinyl]-6-fluoro-1-phenyl-1H-indazole, mp 113°–115° C.

ANALYSIS: Calculated for C$_{34}$H$_{32}$F$_3$N$_3$: 75.67%C, 5.98%H, 7.79%N. Found: 75.99%C, 6.20%H, 7.76%N.

EXAMPLE 115

1-[4-(Trifluoromethyl)phenyl]-3-[1-(dimethylphosphinylmethyl)-4-piperidinyl]-1H-indazole A stirred mixture of 4-[1-[4-(trifluoromethyl)phenyl]-1H-indazol-3-yl]piperidine-1-carbonitrile of Example 101 (15 g, 0.041 moles) and 25% H$_2$SO$_4$ (100 ml) was refluxed for 20 hours. The mixture was cooled, poured into H$_2$O, and basified with a 25% NaOH solution. The product was extracted (dichloromethane), dried (MgSO$_4$), and concentrated to yield 13 g (93%) of 1-[4-(trifluoromethyl)phenyl]-3-(4-piperidinyl)-1H-indazole as an oil. A stirred mixture of the indazole (4.0 g, 0.012 moles), potassium carbonate (3.6 g, 0.026 moles) and chloromethyldimethyl phosphine oxide (3.96 g, 0.031 moles) in DMF (30 ml) was heated at 80° C. for 40 hours. The mixture was cooled, poured into H$_2$O, extracted (CHCl$_3$), dried (MgSO$_4$) and concentrated to yield 4.8 g of an oil. The product was purified on the HPLC (silica gel, 5% methanol-CHCl$_3$) and then recrystallized once from acetone-hexane to yield 2.2 g (35%) of 1-[4-(trifluoromethyl)phenyl]-3-[1-(dimethylphosphinyl methyl)-4-piperidinyl]-1H-indazole, m.p. 158°–160° C.

ANALYSIS: Calculated for C$_{22}$H$_{25}$F$_3$N$_3$OP: 60.69%C, 5.79%H, 9.65%N. Found 60.59%C, 5.87%H, 9.68%N.

EXAMPLE 116

4-(5-Fluoro-1-phenyl-1H-indazol-3-yl)piperidine-1-carbonitrile

To a stirred mixture of cyanogen bromide (4.05 g, 0.038 moles) and potassium carbonate (6.2 g, 0.045 moles) in dimethylsulfoxide (75 ml) was added dropwise a solution of 5-fluoro-1-phenyl-3-(1-methyl-4-piperidinyl)-1H-indazole (11.0 g, 0.036 moles) free base of Example 111(b) in hot dimethylsulfoxide (75 ml). The reaction was stirred at ambient temperature for 28 hours and then poured into water. The product was extracted (dichloromethane), dried (MgSO$_4$) and concentrated to yield 10.8 g of a oil which crystallized upon standing. The product was recrystallized twice from isopropyl alcohol-ether and once from isopropyl alcohol which yielded 3.8 g (33%) of the 4-(5-fluoro-1-phenyl-1H-indazol-3-yl)piperidine-1-carbonitrile, m.p. 137°–139°.

ANALYSIS: Calculated for C$_{19}$H$_{17}$FN$_4$: 71.23%C, 5.35%H, 17.49%N. Found: 71.08%C, 5.52%H, 17.57%N.

EXAMPLE 117

4-[1-[2-(Aminocarbonyl)phenyl-1H-indazol-3-yl]piperidine-1-carboximidic acid methyl ester A mixture of 2-[3-(1-cyano-4-piperidinyl)-1H-indazol-1-yl]benzamide (9.7 g, 0.024 mol) methanol (150 ml) and 25% sodium methoxide (5.5 ml) was heated to reflux until solution was effected. The reaction was then stirred at ambient temperature for 16 hours. The solvent was concentrated and the residue was treated with water. The resulting gum was scratched with a glass rod to induce crystallization, and 9.8 g of a solid were collected. The compound was recrystallized from ethanol-water to yield 5.7 g (52.6) of product. An analytical sample was obtained by recrystallization of a 3.0 g sample again from ethanol-water to yield 2.2 g of 4-[1-[2-(aminocarbonyl)phenyl-1H-indazol-3-yl]piperidine-1-carboximidic acid methyl ester, mp 192°–194°.

ANALYSIS: Calculated for $C_{21}H_{23}N_5O_2$: 66.80%C, 6.14%H, 18.56%N. Found: 66.93%C, 6.30%H, 18.49%N.

EXAMPLE 118

1-(4-Aminophenyl)-3-(1-methyl-4-piperidinyl)-1H-indazole

A solution of 1-(4-nitrophenyl)-3-(1-methyl-4-piperidinyl)-1H-indazole (20.0 g, 0.060 moles) in dimethylformamide (300 ml) was added to a 5% palladium on carbon catalyst (1 g). The reduction was carried out on Parr hydrogenation apparatus using an initial pressure of 50 psi of $H_2$, until the uptake of $H_2$ ceased. The catalyst was filtered from the solution and the solvent was removed which produced 20 g of an oil. The product was purified using high pressure liquid chromatography (silica gel, 5% diethylamine-ethyl acetate to yield 10.65 g of a solid. The solid was recrystallized twice from acetone-hexane to yield 6.6 g (36%) of 1-(4-aminophenyl)-3-(1-methyl-4-piperidinyl)-1H-indazole, m.p. 116°–118°.

ANALYSIS: Calculated for $C_{19}H_{22}N_4$: 74.48%C, 7.24%H, 18.28%N. Found: 74.53%C, 7.46%H, 18.39%N.

EXAMPLE 119

1-Formyl-4-[6-fluoro-1-[4-(trifluoromethyl)phenyl]-1H-indazol-3-yl]piperidine

To a stirred suspension, under $N_2$, of NaH (5.8 g, 0.12 mol, of a 50% oil dispersion) in dimethylformamide (DMF) (100 ml) was added, dropwise, 1-formyl-4-(6-fluoro-1H-indazoyl-3-yl)piperidine (25.3 g, 0.094 mol) dissolved in DMF (175 ml). After stirring at ambient temperature for 45 minutes, p-fluorobenzotrifluoride (192 g, 0.12 mol) was added dissolved in DMF (175 ml). After stirring at ambient temperature for 45 minutes, p-fluorobenzotrifluoride (192 g, 0.12 mol) was added dissolved in DMF (20 ml). The temperature was then raised to 83°–85° and stirring was continued at this temperature for 16 hours. The reaction was poured into $H_2O$, and the aqueous mixture was extracted with ethyl acetate. The organic layer was washed ($H_2O$), dried (MgSO$_4$) and the solvent was concentrated to yield 38.4 of an oil. The oil was combined with a 3.8 g sample from another run and chromatographed on a Water's Prep 500 HPLC utilizing silica gel columns and eluting with $CH_2Cl_2$/methanol (2%). Concentration of the appropriate fractions yielded 25 g (61%) of the indazole. Recrystallization of 4.0 g from isopropanol-$H_2O$ yielded 3.4 g of 1-formyl-4-[6-fluoro-1-[4-(trifluoromethyl)phenyl]-1H-indazol-3-yl]piperidine, mp 142°–144°.

ANALYSIS: Calculated for $C_{20}H_{17}F_4N_3O$: 61.38%C, 4.38%H, 10.74%N. Found: 61.15%C, 4.45%H, 10.68%N.

EXAMPLE 120

4-[6-Fluoro-1-[4-(trifluoromethyl)phenyl]-1H-indazol-3-yl]piperidine-1-carboxamide To a solution of 6-fluoro-1-[4-(trifluoromethyl)phenyl]-3-(4-piperidinyl)-1H-indazole (4.0 g, 0.11 mol) in DMF was added nitrourea (2.6 g, 0.04 mol). Almost immediately, a solid precipitated from solution, and the reaction was then heated on a steam bath to effect solution (gas evolution). After standing for 1 hour at ambient temperature, the reaction was poured into $H_2O$, and the aqueous mixture was extracted with ethyl acetate. The ethyl acetate extract was washed ($H_2O$), dried (MgSO$_4$) and the solvent concentrated to yield 4.2 g of a solid. This material was combined with another sample (1.2 g) and the combined sample chromatographed with a Water's Prep 500 on silica gel columns. The desired product was eluted with $CH_2Cl_2$-methanol (4%), and after concentration of the appropriate fractions, the product was isolated as a solid. The solid was triturated with ether and 3.5 g of the ureas was collected. Recrystallization from methyl acetate-hexane yielded 2.7 g (48%) of 4-[6-fluoro-1-[4-(trifluoromethyl)phenyl]-1H-indazol-3-yl]piperidine-1-carboxamide, m.p. 148°–150°.

ANALYSIS: Calculated for $C_{20}H_{18}F_4N_4O$: 59.09%C, 4.46%H, 13.78%N. Found: 59.09%C, 4.64%H, 13.76%N.

EXAMPLE 121

5-Fluoro-3-(1-methyl-4-piperidinyl)-1H-indazole

A mixture of 4-(2,5-difluorobenzoyl)-1-methylpiperidine of Example 111 (38.5 g, 0.16 moles) and hydrazine monohydrate (79.5 g, 1.59 moles) was heated in an autoclave at 150° for 22 hours. The autoclave was cooled in an ice bath and then opened. The reaction mixture was poured into $H_2O$, causing the product to crystallize. The product was collected and then recrystallized twice from toluene to yield 8.2 g (22%) of 5-fluoro-3-(1-methyl-4-piperidinyl)-1H-indazole, m.p. 202°–204°.

ANALYSIS: Calculated for $C_{13}H_{16}FN_3$: 66.93%C, 6.91%H, 18.01%N. Found: 66.82%C, 6.88%H, 18.07%N.

EXAMPLE 122

5-Fluoro-1-[4-(trifluoromethyl)phenyl]-3-(1-methyl-4-piperidinyl)-1H-indazole

To a suspension of NaH (4.1 g, 0.085 moles, 50% oil dispersion) in DMF (110 ml) was added a solution of 5-fluoro-3-(1-methyl-4-piperidinyl)-1H-indazole (16.5 g, 0.071 moles) in hot DMF (110 ml). The mixture was stirred at ambient temperature for 1 hour and then 4-fluorobenzotrifluoride (10.6 ml, 0.084 moles) was added. The reaction was heated at 90° for 20 hours and then cooled and poured into $H_2O$. The product was extracted (ethyl acetate), dried (MgSO$_4$), and concentrated to yield 21.5 g of an oil. The product was purified by high pressure liquid chromatography (silica gel, 3% diethylamine-ethyl acetate) to yield 17.8 g of product. The product was triturated with hexane to yield 15.5 g (58%) of 5-fluoro-1-[4-(trifluoromethyl)phenyl]-3-(1-methyl-4-piperidineyl)-1H-indazole, m.p. 126°–128°.

ANALYSIS: Calculated for $C_{20}H_{19}F_4N_3$: 63.65%C, 5.07%H, 11.13%N. Found: 63.43%C, 5.03%H, 11.26%N.

EXAMPLE 123

6-Fluoro-3-(4-piperidinyl)-1-[4-(trifluoromethyl)-phenyl]-1H-indazole Hydrochloride A mixture of 6-fluoro-3-(1-formyl-4-piperidinyl)-1-[4-(trifluoromethyl)phenyl]-1H-indazole (9.5 g, 0.024 mol), 3N HCl (90 ml) and ethanol (90 ml) was stirred and refluxed for 3 hours. After stirring at ambient temperature for 11 hours, the reaction mixture was diluted with $H_2O$, cooled in an ice bath, and was made basic by the dropwise addition of 25% aqueous NaOH. The basic mixture was extracted with ethyl acetate, the extract washed ($H_2O$), dried ($MgSO_4$) and the solvent was concentrated to yield 7.0 g (80%) of a solid. A 2.4 g sample was removed, dissolved in ethanol-ether and an ethereal solution of HCl was added to precipitate 2.4 g of a hydrochloride salt. Recrystallization from isopropyl alcohol-ether yielded 1.5 g of 6-fluoro-3-(4-piperidinyl)-1-[4-(trifluoromethyl)phenyl]-1H-indazole hydrochloride, mp 231°–233°.

ANALYSIS: Calculated for $C_{19}H_{17}F_4N_3 \cdot HCl$: 57.13%C, 4.52%H, 10.52%N. Found: 56.86%C, 4.54%H, 10.57%N.

EXAMPLE 124

5-Fluoro-1-[4-(trifluoromethyl)phenyl]-3-(4-piperidinyl)-1H-indazole Hydrochloride To a solution of 5-fluoro-1-[4-(trifluoromethyl)-phenyl]-3-(1-methyl-4-piperidinyl)-1H-indazole (13.2 g, 0.035 moles) in 1,2-dichloroethane (35 ml) at 0° C. was added 1-chloroethylchloroformate (3.9 ml, 0.035 moles). The reaction was stirred for 15 minutes at 0° and then for 4 hours at ambient temperature. The solvent was removed and then methanol (90 ml) was added. The mixture was refluxed for 1 hour and then the methanol was removed which left 17.8 g of a solid. The product was recrystallized twice from isopropyl alcohol to yield 6.3 g (45%) of 5-fluoro-1-[4-(trifluoromethyl)phenyl]-3-(4-piperidinyl)-1H-indazole hydrochloride, mp 276°–278°.

ANALYSIS: Calculated for $C_{19}H_{17}F_4N_3 \cdot HCl$: 57.08%C, 4.54%H, 10.51%N. Found: 57.15%C, 4.44%H, 10.59%N.

EXAMPLE 125

4-[6-Fluoro-1-[4-(trifluoromethyl)phenyl]-1H-indazol-3-yl]piperidine-1-acetamide A mixture of 6-fluoro-3-(4-piperidinyl)-1-[4-(trifluoromethyl)phenyl]-1H-indazole free base of Example 123 (6.2 g, 0.017 mol), 2-chloroacetamide (1.7 g, heated at 90° C. for 0.75 hours. The reaction was poured into $H_2O$, and after standing at ambient temperature for 2 hours, 5.1 g of a solid was collected. The solid was flash chromatographed [silica gel: $CH_2Cl_2$/methanol (5%)] to yield an oil which upon trituration with ether gave 3.8 g of a solid. Recrystallization from isopropyl alcohol-$H_2O$ yielded 3.6 g (50%) of 4[6-fluoro-1-[4-(trifluoromethyl)phenyl]-1H-indazol-3-yl]piperidine-1-acetamide, mp 174°–176°.

ANALYSIS: Calculated for $C_{21}H_{20}F_4N_4O$: 59.99%C, 4.80%H, 13.22%N. Found: 59.76%C, 4.86%H, 13.25%N.

EXAMPLE 126

4-[5-Fluoro-1-[4-(trifluoromethyl)phenyl]-1H-indazol-3-yl]piperidine-1-carboxamide To a solution of 5-fluoro-1-[4-(trifluoromethyl)-phenyl]-3-(4-piperidinyl)-1H-indazole free base of Example 124 (6.3 g, 0.017 moles) in DMF (100 ml) was added nitrourea (2.2 g, 0.021 moles). The mixture was warmed on a steam bath until gas began to evolve and was then stirred at ambient temperature for 4 hours. The mixture was then poured into $H_2O$ and the product extracted (dichloromethane), dried ($MgSO_4$), and concentrated to yield 6.9 g of an oil. The oil was triturated with water to produce 6.9 g of a solid. The product was purified by high pressure liquid chromatography (silica gel 100% ethyl acetate) followed by recrystallization from isopropyl alcohol to yield 2.75 g (39%) of 4-[5-fluoro-1-[4-(trifluoromethyl)phenyl]-1H-indazol-3-yl]piperidine-1-carboxamide, mp 172°–174°.

ANALYSIS: Calculated for $C_{20}H_{18}F_4N_4O$: 59.11%C, 4.46%H, 13.79%N. Found: 58.83%C, 4.46%H, 13.55%N.

I claim:
1. A compound having the formula

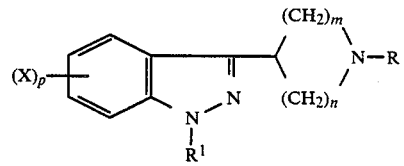

wherein R is hydrogen, loweralkyl, loweralkenyl, lowercycloalkylloweralkyl,

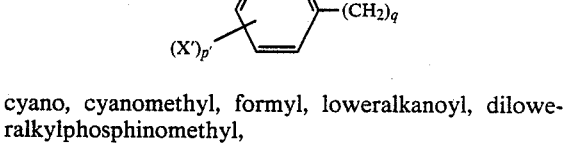

cyano, cyanomethyl, formyl, loweralkanoyl, diloweralkylphosphinomethyl,

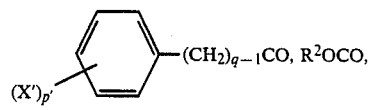

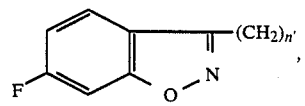

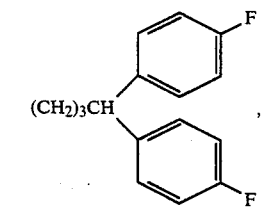

-continued

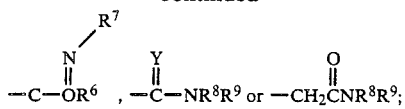

R¹ is hydrogen, loweralkyl, loweralkenyl, lowercycloalkyloweralkyl,

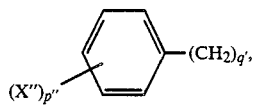

diloweralkylaminoloweralkyl, cyano, cyanomethyl, formyl, loweralkanoyl, hydroxymethyl, hydroxyloweralkyl, lowercycloalkylloweralkanoyl, loweralkoxycarbonylloweralkyl,

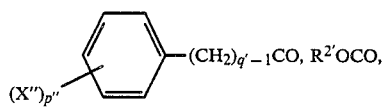

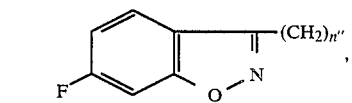

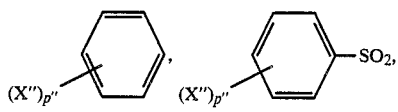

2- or 4-pyridinyl or 2-pyrimidinyl; R² and R²' are independently loweralkyl, 2,2,2-trichloroethyl, phenyl or

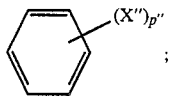

X, X' and X" are independently hydrogen, halogen, loweralkyl, loweralkoxy, loweralkanoyl, loweralkylthio, cyano, carbamoyl, hydroxy, nitro, amino or trifluoromethyl; Y is oxygen or sulfur, m is 2 or 3, n is 1 or 2, and the sum of m and n is 3 or 4; n' and n" are independently 2 or 3; p, p' and p" are independently 1 or 2 except when X" is halogen, p" is 1 through 5; q and q' are independently 1,2, 3, or 4; R⁶ is loweralkyl,

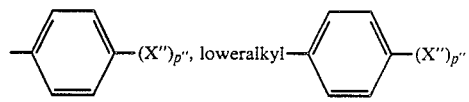

cycloalkylloweralkyl, where the cycloalkyl group contains 3 to 10 carbon atoms, a lower alkyl substituted with an amino, loweralkylamino, diloweralkylamino; R⁷, R⁸, and R⁹ are independently hydrogen, loweralkyl or

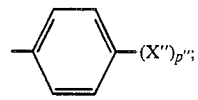

with the proviso that at least one of R and R¹ is a heterocyclic group as specified above; the optical antipode thereof; or the pharmaceutically acceptable salt thereof.

2. A compound according to claim 1 wherein R is

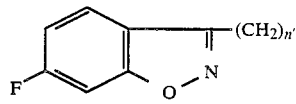

3. A compound according to claim 1 wherein R¹ is

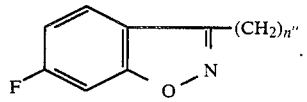

4. The compound of claim 3 which is 1-(6-fluoro-1,2-benzisoxazole-3-propyl)-3-(1-methyl-4-piperidinyl)-1H-indazole.

5. A compound according to claim 1 wherein R¹ is 2- or 4-pyridinyl or 2-pyrimidinyl.

6. The compound of claim 5 which is 1-(4-pyridinyl)-3-(1-methyl-4-piperidinyl)-1H-indazole.

7. The compound of claim 5 which is 1-(2-pyridinyl)-3-(1-methyl-4-piperidinyl)-1H-indazole.

* * * * *